US006441177B1

(12) United States Patent
Aebi et al.

(10) Patent No.: US 6,441,177 B1
(45) Date of Patent: *Aug. 27, 2002

(54) TERTIARY AMINES

(75) Inventors: Johannes Aebi, Basel (CH); Henrietta Dehmlow, Grenzach-Wyhlen (DE); Jacques Himber, Guebwiller (FR); Synèse Jolidon, Blauen (CH); Hans Lengsfeld, Basel (CH); Olivier Morand, Hegenheim (FR); Gérard Schmid, Kienberg (CH); Yu-Hua Ji, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/464,435

(22) Filed: Dec. 16, 1999

Related U.S. Application Data

(62) Division of application No. 08/762,827, filed on Dec. 6, 1996, now Pat. No. 6,034,275.

(30) Foreign Application Priority Data

Dec. 8, 1995 (CH) ................................. 3479/95

(51) Int. Cl.[7] ..................... C07D 401/00; C07D 211/26; C07D 333/32; C07D 233/00; C07C 213/00
(52) U.S. Cl. .................. 546/193; 546/194; 546/207; 546/209; 546/210; 546/212; 546/229; 546/232; 546/236; 546/237; 546/242; 546/246; 546/248; 546/314; 546/329; 546/334; 546/335; 546/336; 546/337; 548/265.8; 548/267.2; 548/252; 548/253; 548/254; 548/300.1; 548/560; 548/561; 548/562; 548/564; 548/570; 548/571; 549/62; 549/64; 549/65; 558/415; 504/323; 504/324; 504/337; 504/353
(58) Field of Search .................... 564/353, 323, 564/324, 337; 558/415; 546/193, 194, 207, 209, 210, 212, 242, 246, 248, 329, 334, 335, 336, 229, 232, 236, 237, 337, 314; 548/265.8, 767.2, 300.1, 252, 253, 254, 560, 561, 562, 564, 570, 571; 549/12, 64, 65

(56) References Cited

U.S. PATENT DOCUMENTS

| 5,106,878 A | 4/1992 | Guerry et al. ............... 514/651 |
| 5,137,920 A | 8/1992 | Guerry et al. ............... 514/648 |
| 5,177,067 A | 1/1993 | Guerry et al. ............... 514/183 |
| 5,495,048 A | 2/1996 | Aebi et al. .................. 564/353 |

FOREIGN PATENT DOCUMENTS

| EP | 410 359 | 1/1931 |
| EP | 114 410 | 8/1984 |
| EP | 359 547 | 3/1990 |
| EP | 464 465 | 1/1992 |
| EP | 636 367 | 2/1995 |

OTHER PUBLICATIONS

Gamble et al., J. Lipid Res., 19:1068–2071 (1978).
Gotto et al., Circulation, 81:1721–1733 (1990).
Stein et al., Nutr. Metab. Cardiovasc. Dis., 2:113–156 (1992).
Hennes et al., Science Tools, 36:10–12 (1992).
Abstract for Document B2.
Abstract For Document B3.
Abstract for B4.
Abstract for B5.

*Primary Examiner*—Alan L. Rotman
*Assistant Examiner*—Raymond Covington
(74) *Attorney, Agent, or Firm*—Geoge W. Johnston; John P. Parise

(57) ABSTRACT

Tertiary amines of the formula

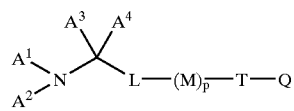

wherein
$A^1$, $A^2$, $A^3$, $A^4$, M, p, T and Q are as defined herein, and acid addition salts thereof, have antimycotic and cholesterol-lowering activity.

48 Claims, No Drawings

TERTIARY AMINES

CROSS REFERENCE TO RELATED APPLICATIONS

This is a divisional of application Ser. No. 08/762,827, filed Dec. 6, 1996, now U.S. Pat. No. 6,034,275.

BACKGROUND OF THE INVENTION

1. Field

The present invention is concerned with novel tertiary amines, a process for their manufacture, pharmaceutical preparations which contain such compounds and the use of these compounds in the production of pharmaceutical preparations.

2. Description

There has been a long felt need in the medical community for antimycoticly active agents and cholesterol-lowering agent. The subject invention addresses this need.

SUMMARY OF THE INVENTION

The subject invention provides compounds of the formula:

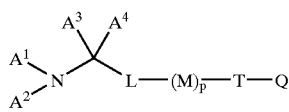

I wherein $A^1$ is $C_1$–$C_{20}$ alkyl or $C_3$–$C_{20}$ alkenyl, $A^2$ is $C_3$–$C_6$ cycloalkyl, $C_3$–$C_6$ cycloalkyl-$C_1$–$C_{20}$-alkyl, unsubstituted $C_1$–$C_{20}$ alkyl, unsubstituted $C_3$–$C_{20}$ alkenyl, $C_1$–$C_{20}$ alkyl substituted by $R^1$, $CONH_2$ or CN, or $C_3$–$C_{20}$ alkenyl substituted by $R^1$, $CONH_2$ or CN, and when $A^1$ is $C_1$–$C_{20}$ alkyl, $A^2$ can also be OH, and $A^3$ and $A^4$ are each independently hydrogen or $C_1$–$C_{20}$ alkyl; or $A^1$ and $A^2$ together form a $C_2$–$C_8$ alkylene, $C_4$–$C_8$ alkenylene, $C_6$–$C_8$ alkadienylene, $R^1$ substituted $C_2$–$C_8$ alkylene, $R^1$ substituted $C_4$–$C_8$ alkenylene, or $R^1$ substituted $C_6$–$C_8$ alkadienylene group $A^1$-$A^2$, and in group $A^1$-$A^2$ one or two C atoms can be replaced by one or two groups selected from the group consisting of N atoms and $N(C_1$–$C_{20}$ alkyl), or $A^1$ and $A^3$ together form a $C_2$–$C_8$ alkylene, $C_4$–$C_8$ alkenylene, $C_6$–$C_8$ alkadienylene, $R^1$ substituted $C_2$–$C_8$ alkylene, $R^1$ substituted $C_4$–$C_8$ alkenylene, or $R^1$ substituted $C_6$–$C_8$ alkadienylene group $A^1$-$A^3$, and in group $A^1$-$A^3$ one or two C atoms can be replaced by one or two groups selected from the group consisting of N atoms and $N(C_1$–$C_{20}$ alkyl);

$R^1$ is OH, oxo, $C_1$–$C_{20}$ alkyl(O), $C_1$–$C_{20}$ alkyl(S) or di($C_1$–$C_{20}$ alkyl)amino bonded to a saturated C atom of $A^2$, $A^1$-$A^2$ or $A^1$-$A^3$, provided that a C atom substituted by $R^1$ or an unsaturated C atom present in $A^1$, $A^2$, $A^1$-$A^2$ or $A^1$-$A^3$ must be bonded in a position other than the α-position to $N(A^1 A^2)$;

p=1 and L is phenylene, $C_4$–$C_{11}$ alkylene which has at least 4 C atoms between the two free valencies or $C_3$–$C_{11}$ alkenylene which has at least 3 C atoms between the two free valencies, and which is bonded to M directly or via O, NH or $N(C_1$–$C_{20}$ alkyl) or $N(C_1$–$C_{20}$ alkanoyl), or L is $C_3$–$C_6$ cycloalkylene-$C_1$–$C_{20}$-alkylene, or p=0 and L is $C_6$–$C_{11}$-alkenylene or $C_6$–$C_{11}$-alkadienylene, bonded to T;

M is thienylene, pyridylene, 1,4-phenylene, 1,4-phenylene substituted by at least one substituent selected from the group consisting of $C_1$–$C_{20}$ alkyl, halogen, $N(R^2,R^{21})$, $CONH_2$, CN, $NO_2$, $CF_3$, OH, $C_1$–$C_{20}$ alkyl(O), $C_1$–$C_{20}$ alkyl(S), 1,2,4-triazol-1-yl and tetrazol-1-yl, or a group of the formula:

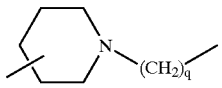

($M^1$)

q is 1 or 0;

$R^2$ and $R^{21}$ are independently H, $C_1$–$C_{20}$ alkyl, $C_2$–$C_{20}$ alkenyl, $C_1$–$C_{20}$ alkanoyl or $SO_2$—($C_1$–$C_{20}$ alkyl);

T is CO, $CH(R^3)$, $C(R^4,R^5)$ or $C$=$NOR^6$ and, when M is a group $M^1$ and q=0, T can also be $SO_2$;

$R^3$ is OH, F, $C_1$–$C_{20}$ alkoxy or $C_1$–$C_{20}$ alkanoyloxy;

$R^4$ is OH and $R^5$ is $C_1$–$C_{20}$ alkyl, $C_2$–$C_{20}$ alkenyl, $C_2$–$C_{20}$ alkinyl, cycloalkyl or $CF_3$, or $R^4$ and $R^5$ together are the group $CH_2$, $CH_2O$ or $CH_2CH_2$;

$R^6$ is H, $C_1$–$C_{20}$ alkyl or $C_2$–$C_{20}$ alkenyl;

Q is $C_3$–$C_6$ cycloalkyl, $C(R^7,R^8)$, phenyl substituted by at least one substituent selected from the group consisting of $C_1$–$C_{20}$ alkyl, halogen, $N(R^9,R^{10})$, $CONH_2$, CN, $NO_2$, $CF_3$, 1,2,4-triazol-1-yl and tetrazol-1-yl, or a straight-chain $C_6$–$C_{13}$ alkyl, $C_6$–$C_{13}$ alkenyl, $C_6$–$C_{13}$ alkadienyl or $C_6$–$C_{13}$ alkatrienyl group Q' with 0 to 3 methyl substituents, and a group Q' can be substituted by at least one substituent selected from the group consisting of OH and $N(R^9,R^{10})$, $R^7$ and $R^8$ are $C_5$–$C_{11}$-alkyl, $C_5$–$C_{11}$-alkenyl or $C_5$–$C_{11}$-alkadienyl, and $R^9$ and $R^{10}$ are H, $C_1$–$C_{20}$ alkyl, $C_2$–$C_{20}$ alkenyl or $C_1$–$C_{20}$ alkanoyl, provided that (a) $A^2$ must not be $C_1$–$C_{20}$ alkyl or $C_3$–$C_{20}$ alkenyl, or $A^1$ and $A^2$ together must not be $C_2$–$C_8$ alkylene in a compound of formula I in which T is a group CO or CHOH, L is phenylene or an $C_4$–$C_{11}$ alkylene or $C_3$–$C_{11}$ alkenylene group bonded to M directly or via O or $N(C_1$–$C_{20}$ alkyl), M is 1,4-phenylene or 1,4-phenylene monosubstituted by $C_1$–$C_{20}$ alkyl, $C_1$–$C_{20}$ alkyl(O), halogen, CN, $NO_2$ or $CF_3$, and Q is substituted phenyl, $C_6$–$C_{13}$ alkenyl, $C_6$–$C_{13}$ alkyl or $C_6$–$C_{13}$ alkyl substituted by OH, (b) M must not be pyridylene in a compound of formula I in which $A^1$ and $A^2$ together are $C_2$–$C_8$ alkylene or $C_2$–$C_8$ alkylene substituted by $R^1$, $A^2$ is $C_1$–$C_{20}$ hydroxyalkyl or $A^1$ and $A^2$ are each $C_1$–$C_{20}$ alkyl, and (c) in a compound of formula I in which T is a group $C(OH, R^{51})$, wherein $R^{51}$ is $C_1$–$C_{20}$ alkyl, $C_2$–$C_{20}$ alkenyl, $C_2$–$C_{20}$ alkynyl or $C_3$–$C_6$ cycloalkyl, M is 1,4-phenylene or substituted 1,4-phenylene and L is an alkylene group bonded to M via a O atom, the alkylene must be a $C_5$–$C_{11}$ alkylene containing at least 5 C atoms between the 2 free valencies, and pharmaceutically usable acid addition salts thereof.

Of particular importance are compounds of the formula:

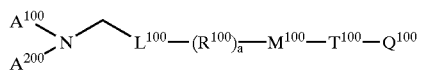

wherein

A$^{100}$ is C$_1$–C$_6$ alkyl;

A$^{200}$ is C$_3$–C$_6$ cycloalkyl, C$_3$–C$_6$ alkenyl, C$_1$–C$_6$ alkyl, C$_3$–C$_6$ cycloalkyl-C$_{13}$-alkyl;

L$^{100}$ is C$_4$–C$_6$ alkylene, C$_3$–C$_6$ alkenylene, or C$_3$–C$_6$ cycloalkylene-C$_1$–C$_{13}$-alkylene;

a is 1;

R$^{100}$ is O;

M$^{100}$ is 1,4-phenylene, 1,4-phenylene substituted with at least one substituent selected from the group consisting of halogens, T$^{100}$ is C=O, C=N—O—(C$_1$–C$_6$ alkyl), C=CH$_2$, C(C$_1$–C$_6$ alkyl, OH); and Q$^{100}$ is phenyl substituted with at least one substituent selected from the group consisting of the halogens, and pharmaceutically salts acid addition salts thereof.

Especially preferred are compounds wherein

A$^{100}$ is C$_1$–C$_3$ alkyl;

A$^{200}$ is C$_3$–C$_6$ cycloalkyl, C$_3$–C$_6$ alkenyl;

L$^{100}$ is C$_3$–C$_5$ alkenylene or C$_3$–C$_6$ cycloalkylene-C$_1$–C$_3$-alkylene;

a is 1;

R$^{100}$ is O;

M$^{100}$ is 1,4, phenylene, 1,4 phenylene substituted with at least one fluorine;

T$^{100}$ is C=O, C=N—O—(C$_1$–C$_3$ alkyl), C=CH$_2$, C(C$_1$–C$_3$ alkyl, OH); and Q$^{100}$ is phenyl substituted with at least one halogen atom, and pharmaceutically usable acid addition salts thereof.

And more preferred compounds are wherein

A$^{100}$ is methyl;

A$^{200}$ is cyclopropyl or allyl;

L$^{100}$ is cyclopropylene-methylene or propenylene;

R$^{100}$ is O;

M$^{100}$ is 1,4-phenylene or 3 fluoro-1,4-phenylene;

T$^{100}$ is C=O or C(CH$_3$)OH; and

Q$^{100}$ is bromophenyl, and pharmaceutically usable acid addition salts thereof.

Compounds of the structures:

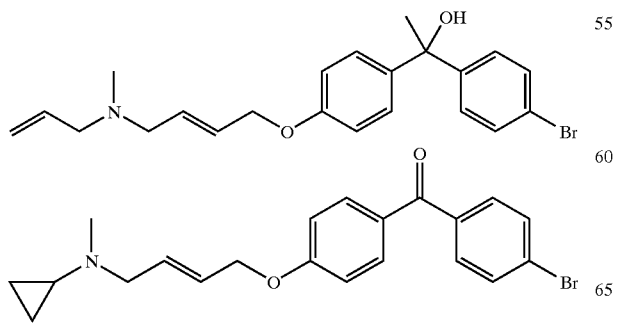

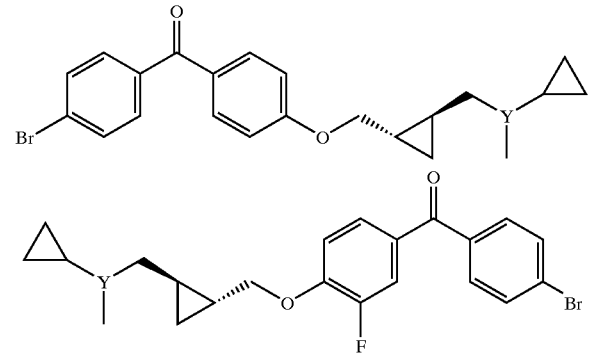

and pharmaceutically usuable acid addition salts thereof are favored.

DETAILED DESCRIPTION OF THE INVENTION

The subject invention will now be described in terms of its preferred embodiments. These embodiments are set forth to aid in understanding the invention, but are not to be construed as limiting.

The invention is concerned with tertiary amines of the formula

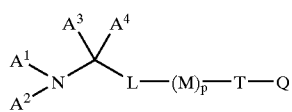

I wherein

A$^1$ is alkyl or alkenyl and

A$^2$ is cycloalkyl, cycloalkyl-alkyl or an alkyl or alkenyl group optionally substituted by a group R$^1$, CONH$_2$ or CN and, where A$^1$ is alkyl, A$^2$ can also be OH, A$^3$ and A$^4$ are hydrogen or alkyl or A$^1$ and A$^2$ or A$^3$ together form an alkylene, alkenylene or alkadienylene group A$^1$-A$^2$ or A$^1$-A$^3$ with up to 5 C atoms optionally substituted by R$^1$, and in a group A$^1$-A$^2$ or A$^1$-A$^3$ up to 2 C atoms can be replaced by one (or two) N atom(s) and/or by a N-alkyl group, R$^1$ is OH, oxo, alkyl(O or S) or dialkylamino bonded to a saturated C atom of A$^2$, A$^1$-A$^2$ or A$^1$-A$^3$, provided that a C atom substituted by R$^1$ or an unsaturated C atom present in A$^1$, A$^2$, A$^1$-A$^2$ or A$^1$-A$^3$ must be bonded in a position other than the α-position to N(A$^1$A$^2$), p=1 and L is phenylene, or alkylene or alkenylene which has a total of up to 11 C atoms and at least 4 or, respectively, 3 C atoms between the two free valencies and which is bonded to M directly or via O, NH or N(alkyl or alkanoyl) or L is cycloalkylene-alkylene or p=0 and L is C$_{6-11}$-alkenylene or C$_{6-11}$-alkadienylene bonded to T, M is thienylene, pyridylene, 1,4-phenylene, 1,4-phenylene substituted by one or more substituents from the group of alkyl, halogen, N(R$^2$,R$^{21}$), CONH$_2$, CN, NO$_2$, CF$_3$, OH, alkyl(O or S), 1,2,4-triazol-1-yl or tetrazol-1-yl or a group of the formula

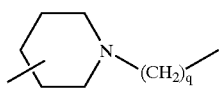

Q is 1 or 0,

R² and R²¹ are H, alkyl, alkenyl, alkanoyl or SO₂-alkyl,

T is CO, CH(R³), C(R⁴,R⁵) or C=NOR⁶ and, where M is a group M¹ and q=0, T can also be SO₂, R³ is OH, F, alkoxy or alkanoyloxy, R⁴ is OH and R⁵ is alkyl, alkenyl, alkynyl, cycloalkyl or CF₃ or R⁴ and R⁵ together are the group CH₂, CH₂O or CH₂CH₂, R⁶ is H, alkyl or alkenyl, Q is cycloalkyl, C(R⁷,R⁸), phenyl substituted by one or more substituents from the group of alkyl, halogen, N(R⁹,R¹⁰), CONH₂, CN, NO₂, CF₃, 1,2,4-triazol-1-yl and tetrazol-1-yl or a straight-chain alkyl, alkenyl, alkadienyl or alkatrienyl group Q' with 0 to 3 methyl substituents and a total of 6 to 13 C atoms, and a group Q' can be substituted by OH and/or by N(R⁹,R¹⁰), R⁷ and R⁸ are $C_{5-11}$-alkyl, $C_{5-11}$-alkenyl or $C_{5-11}$-alkadienyl and R⁹ and R¹⁰ are H, alkyl, alkenyl or alkanoyl, with the provisos that a) A² must not be alkyl or alkenyl or A¹ and A² together must not be alkylene in a compound of formula I in which T is a group CO or CHOH, L is phenylene or an alkylene or alkenylene group bonded to M directly or via O or N-alkyl, M is 1,4-phenylene or 1,4-phenylene monosubstituted by alkyl, alkoxy, halogen, CN, NO₂ or CF₃ and Q is substituted phenyl, an alkenyl group or an alkyl group optionally substituted by OH, b) M must not be pyridylene in a compound of formula I in which A¹ and A² together signify alkylene or alkylene substituted by R¹, A² is hydroxyalkyl or A¹ and A² are each an alkyl group and c) in a compound of formula I in which T is a group C(OH, R⁵¹), wherein R⁵¹ is alkyl, alkenyl, alkynyl or cycloalkyl, M is 1,4-phenylene or substituted 1,4-phenylene and L is an alkylene group bonded to M via a O atom, the alkylene group must contain at least 5 C atoms between the 2 free valencies and a total of up to 11 C atoms, and acid addition salts thereof.

In the scope of the present invention terms such as "alkyl", "alkenyl", "alkadienyl" and "alkatrienyl" alone or in combination such as in cycloalkyl-alkyl denote monovalent and, unless specified otherwise, straight-chain or branched groups with up to 20, especially up to 13, C atoms; further in the case of alkyl, alkenyl and alkadienyl up to 8 C atoms, in the case of alkyl and alkenyl up to 6, especially up to 4, C atoms. Examples for alkyl are methyl, ethyl, propyl, isopropyl, n-, s- and t-butyl, pentyl, hexyl, decyl and dodecyl, for alkanoyl: formyl and acetyl, for alkenyl: vinyl, allyl, propenyl, butenyl, 3-methyl-2-butenyl, 4-methyl-3-pentenyl and undodecenyl, for alkynyl: ethynyl, for alkadienyl: 4-methyl-1,3-pentadienyl; 3,7-dimethyl-2,6-octadienyl and 4,8-dimethyl-3,7-nonadienyl, for alkatrienyl: 4,8-dimethyl-1,3,7-nonatrienyl. "Alkylene", "alkenylene" and "alkadienylene" denote the divalent groups corresponding to the monovalent alkyl, alkenyl and, respectively, alkadienyl groups defined above, such as pentylene and 3-methyl-pentylene; propenylene and 2,6-dimethyl-1-hexenylene; 1,5-dimethyl-1,5-hexadienylene; 2,6-dimethyl-1,5-hexadienylene; 2,6-dimethyl-1,5-octadienylene and 3,7-dimethyl-3,7-octadienylene. "Cycloalkyl" and "cycloalkylene" alone or in combination preferably contain 3 to 6 C atoms such as e.g. cyclopropyl and cyclohexyl and, respectively, cyclopropylene. Examples of "thienylene" and "pyridylene" groups are 2,5-thienylene and, respectively, 2,5- or 3,6-pyridylene.

Preferably, A¹ stands for methyl, ethyl or allyl; A² stands for methyl, ethyl, allyl, hydroxy, hydroxypropyl, 2-methoxyethyl, 2-methylsulphanyl-ethyl, carbamoylmethyl, 2-oxo-1-propyl, 2-cyanoethyl, cyclopropyl, cyclopropylmethyl; N(A¹,A²) stands for imidazolyl, 4-hydroxy-piperidin-1-yl or 4-dimethylamino-piperidin-1-yl; A³ and A⁴ stand for hydrogen or methyl; (A¹,A²)N—C(A³,A⁴)-stands for 1-methylpyrrolidin-2-yl; L stands for (CH₂)₅O, CH=CHCH₂O, 1,4-phenylene, cyclopropylene-methyleneoxy, (CH₂)₅—NH, CH=CHCH₂NH, (CH₂)₅N(acetyl), CH=CHCH₂N (acetyl), CH=C(CH₃)CH₂CH₂CH₂CH(CH₃), CH=C (CH₃)CH₂CH₂CH=C(CH₃), C(CH₃)=CHCH₂CH₂C (CH₃)=CH, CH=C(CH₃)CH₂CH₂CH=C(CH₃)CH₂CH₂ or CH₂CH₂C(CH₃)=CHCH₂CH₂C(CH₃)=CH; M stands for 1,4-phenylene which can be monosubstituted by fluorine, OH, NH₂, NHCH₃, N(CH₃)₂, NH(CHO), NH(SO₂CH₃), SCH₃ or 1,2,4-triazol-1-yl, substituted by fluorine and methyl or di- or tetrasubstituted by fluorine; T stands for CO, CHOH, SO₂, C=CH₂, C(CH₂CH₂), C(OH, vinyl), CHF, C(OH, CH₃), C(OH, CF₃), C(OH, cyclopropyl), C=NOH, C=NOCH₃, C=NO-tert.butyl or C=NO-allyl; Q stands for bromophenyl, cyanophenyl, carbamoylphenyl, difluorophenyl, phenyl substituted by F and N(CH₃)₂, cyclohexyl, 4-methylpentyl, 3-butenyl, 4-methyl-3-pentenyl, 4-methyl-1,3-pentadienyl, 4,8-dimethyl-1,3,7-nonatrienyl, 10-aminodecyl, 10-acetaminodecyl, 2-hydroxy-1,2-(allyl-methyl-amino)dodecyl, 1,2-(allyl-methyl-amino)-1-dodecenyl, 2-hydroxy-4-methyl-3-pentenyl; 4,8-dimethyl-2-hydroxy-3,7-nonadienyl, CH[CH₂CH=C(CH₃)₂]₂ or CH[CH₂CH=C(CH₃) CH₂CH₂CH=C(CH₃)₂]₂.

As pharmaceutically acceptable acid addition salts there come into consideration salts of compounds I with inorganic and organic acids such as HCl, HBr, H₂SO₄, HNO₃, citric acid, acetic acid, succinic acid, fumaric acid, tartaric acid, methanesulphonic acid and p-toluenesulphonic acid.

The compounds of formula I which contain one or more asymmetric C atoms can be present as enantiomers, as diastereomers or as mixtures thereof, for example, as racemates.

Preferred compounds of formula I are

A) those in which A² is cycloalkyl or cycloalkyl-alkyl and T is CO, especially the compounds of the formula

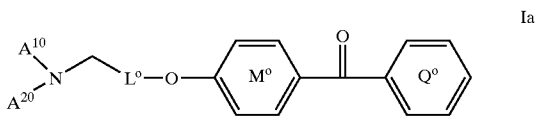

Ia wherein A¹⁰ is alkyl, A²⁰ is cycloalkyl or cycloalkyl-alkyl, L⁰ is alkylene or alkenylene with a total of up to 11 C atoms and at least 4 or, respectively, 3 C atoms between the two free valencies or cycloalkylene-alkylene, M⁰ is optionally halogenated 1,4-phenylene and Q⁰ is phenyl substituted by halogen or CN, especially wherein A¹⁰ is methyl, A²⁰ is cyclopropyl or cyclopropylmethyl, L⁰ is n-pentylene, n-propenylene or cyclopropylenemethylene, M⁰ is unsubstituted or fluorinated 1,4-phenylene and Q⁰ is phenyl substituted by Br or CN, especially:
  (4-bromo-phenyl)-[4-[6-(cyclopropyl-methyl-amino)-hexyloxy]-2-fluoro-phenyl]-methanone,
  (E)-(4-bromo-phenyl)-[4-[4-(cyclopropyl-methyl-amino)-but-2-enyloxy]-phenyl]-methanone,
  [6-[6-(cyclopropyl-methyl-amino)-hexyloxy]-phenyl]-( 4-bromo-phenyl)-methanone,
  (E)4-[4-[4-(cyclopropyl-methyl-amino)-but-2-enyloxy]-3-fluoro-benzoyl]-benzonitrile,
  (4-bromo-phenyl)-[4-[6-(cyclopropylmethyl-methyl-amino)-hexyloxy]-phenyl]-methanone,
  (1RS,2RS)-(4-bromo-phenyl)-[4-[2-[(cyclopropyl-methyl-amino)-methyl]-cyclopropylmethoxy]-phenyl]-methanone,
  (1RS,2RS)-(4-bromo-phenyl)-[4-[2-[(cyclopropyl-methyl-amino)-methyl]-cyclopropylmethoxy]-3-fluoro-phenyl]-methanone
as well as the following compounds:
  1-[4-[6-(cyclopropylmethyl-methyl-amino)-hexyloxy]-2-fluoro-phenyl]-5-methyl-hex-4-en-1-one,
  1-[4-[6-(cyclopropyl-methyl-amino)-hexyloxy]-2-fluoro-phenyl]-5-methyl-hex-4-en-1-one,
  (E)-(4-bromo-phenyl)-[4-[4-(cyclopropylmethyl-methyl-amino)-but-2-enyloxy]-phenyl]-methanone,
  (E)-4-[4-[4-(cyclopropyl-methyl-amino)-but-2-enyloxy]-3-fluoro-benzoyl]-benzamide
  (1RS,2RS)4-[4-[2-[(cyclopropyl-methyl-amino)-methyl]-cyclopropyl-methoxy]-3-fluoro-benzoyl]-benzonitrile,
  (1RS,2RS)-(4-bromo-phenyl)-[4-[2-[(cyclopropylmethyl-methyl-amino)-methyl]-cyclopropylmethoxy]-phenyl]-methanone,
  (1RS,2RS)-(4-bromo-phenyl)-[4-[2-[(cyclopropyl-methyl-amino)-methyl]-cyclopropylmethoxy]-2-fluoro-phenyl]-methanone,
  (1RS,2RS)-[4-[2-[(allyl-cyclopropyl-amino)-methyl]-cyclopropylmethoxy]-phenyl]-(4-bromo-phenyl)-methanone,
  (1RS,2RS)-1-[4-[2-[(cyclopropyl-methyl-amino)-methyl]-cyclopropyl-methoxy]-phenyl]-5-methyl-hexan-1-one,
B) those in which T is a group CHOH, CHF, C(R⁴,R⁵) or C=NOR⁶ and R⁴, R⁵ and R⁶ have the same significance as given above, especially in which T is a group C(OH, alkyl), C(OH, alkenyl), C=CH₂ or C=NO-alkyl, especially the compounds of the formula

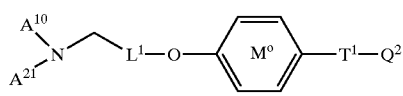

Ib wherein A¹⁰ is alkyl, A²¹ is alkenyl, L¹ is alkylene or alkenylene with a total of up to 11 C atoms and at least 4 or, respectively, 3 C atoms between the two free valencies, M⁰ is optionally halogenated 1,4-phenylene, T¹ is a group C(OH, alkyl), C(OH, alkenyl), C=CH₂ or C=NO-alkyl and Q² is halophenyl or alkenyl with 0 to 3 methyl substituents and a total of 6 to 13 C atoms, especially wherein A¹⁰ is methyl, A²¹ is allyl, L¹ is n-pentylene or n-propenylene, M⁰ is unsubstituted or fluorinated 1,4-phenylene and Q² is bromophenyl or 4-methylpent-3-enyl, especially:
  (E)-(RS)-1-[4-[4-(allyl-methyl-amino)-but-2-enyloxy]-phenyl]-(4-bromo-phenyl)-ethanol,
  (E)-(RS)-1-[4-[4-(allyl-methyl-amino)-but-2-enyloxy]-phenyl]-1-(4-bromo-phenyl)-prop-2-en-1-ol,
  (E)-allyl-[4-[4-[1-(4-bromo-phenyl)-vinyl]-phenoxy]-but-2-enyl]-methyl-amine,
  (RS)-1-[4-[6-(allyl-methyl-amino)-hexyloxy]-2-fluoro-phenyl]-1-(4-bromo-phenyl)-ethanol,
  (E)-(RS)-2-[4-[4-(allyl-methyl-amino)-but-2-enyloxy]-phenyl]-6-methyl-hept-5-en-2-ol
as well as the following compounds:
  (E)-(RS)-[4-[4-(allyl-methyl-amino)-but-2-enyloxy]-phenyl]-(4-bromo-phenyl)-cyclopropyl-methanol,
  (E)-(RS)-1-[4-[4-(allyl-methyl-amino)-but-2-enyloxy]-phenyl]-1-(4-bromo-phenyl)-2,2,2-trifluoro-ethanol,
  (RS)-1-[4-[6-(allyl-methyl-amino)-hexyloxy]-phenyl]-1-(4-bromo-phenyl)-2,2,2-trifluoro-ethanol,
  (E)-allyl-[4-[4-[1-(4-bromo-phenyl)-cyclopropyl]-phenoxy]-but-2-enyl]-methyl-amine,
  (E)-(R or S)-1-[4-[4-(allyl-methyl-amino)-but-2-enyloxy]-phenyl]-(4-bromo-phenyl)-ethanol,
  (E)-(S or R)-1-[4-[4-(allyl-methyl-amino)-but-2-enyloxy]-phenyl]-(4-bromo-phenyl)-ethanol,
  allyl-[6-[4-[1-(4-bromo-phenyl)-vinyl]-3-fluoro-phenoxy]-hexyl]-methyl-amine,
  (E)-(RS)-1-[4-[4-(allyl-methyl-amino)-but-2-enyloxy]-3-fluoro-phenyl]-(4-bromo-phenyl)-prop-2-en-1-ol,
  (RS)-1-[4-[(allyl-methyl-amino)-methyl]-biphenyl-4-yl]-1-(4-bromo-phenyl)-ethanol,
  (RS)-5-[6-(allyl-methyl-amino)-hexyloxy]-2-[1-(4-bromo-phenyl)-1-hydroxy-allyl]-phenol,
  (RS)-1-[4-[6-(allyl-methyl-amino)-hexyloxy]-2-amino-phenyl]-1-(4-bromo-phenyl)-prop-2-en-1-ol,
  (RS)-allyl-[4'-[(4-bromo-phenyl)-fluoro-methyl]-biphenyl-4-ylmethyl]-methyl-amine,
  (E)- and/or (Z)-[4-[(E)-4-(allyl-methyl-amino)-but-2-enyloxy]-phenyl]-(4-bromo-phenyl)-methanone O-methyl oxime,
  (E)- and/or (Z)-[4-[(E)-4-(allyl-methyl-amino)-but-2-enyloxy]-phenyl]-(4-bromo-phenyl)-methanone oxime,
  (E)- and/or (Z)-[4-[(E)-4-allyl-methyl-amino)-but-2-enyloxy]-phenyl-(4-bromo-phenyl)-methanone O-tert-butyl oxime,
  (E)- and/or (Z)-[4-[(E)-4-(allyl-methyl-amino)-but-2-enyloxy]-phenyl]-(4-bromo-phenyl)-methanone O-allyl oxime,
  (E)- and/or (Z)-[4-[6-(allyl-methyl-amino)-hexyloxy]-2-fluoro-phenyl]-(4-bromo-phenyl)-methanone oxime,
C) those in which M is 1,4-phenylene optionally substituted by alkyl, halogen, NH₂, mono- or di-alkylated amino, alkanoylamino, OH, alkyl(O or S) or 1,2,4-triazol-1-yl, especially in which M is 1,4-phenylene substituted by NH₂, mono- or di-alkylated amino, OH, S-alkyl or two halogen atoms, especially the compounds of the formula

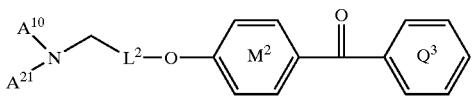

wherein $A^{10}$ is alkyl, $A^{21}$ is alkenyl, $L^2$ is alkylene with up to 11 C atoms and at least 4 C atoms between the two free valencies, $M^2$ is 1,4-phenylene substituted by $NH_2$, mono- or dialkylated amino, OH, S-alkyl or two halogen atoms and $Q^3$ is halogenated phenyl, especially wherein $A^{10}$ is methyl, $A^{21}$ is allyl, $L^2$ is n-pentylene, $M^2$ is 1,4-phenylene substituted by $NH_2$, $NHCH_3$, $N(CH_3)_2$, OH, $SCH_3$ or by two F atoms and $Q^3$ is bromophenyl, especially:

(E)-[4-[4-(allyl-methyl-amino)-but-2-enyloxy]-2,5-difluoro-phenyl]-(4-bromo-phenyl)-methanone,

[4-[6-(allyl-methyl-amino)-hexyloxy]-2-methylsulphanyl-phenyl]-(4-bromo-phenyl)-methanone,

[4-[6-(allyl-methyl-amino)-hexyloxy]-2-methylamino-phenyl]-(4-bromo-phenyl)-methanone,

[4-[6-(allyl-methyl-amino)-hexyloxy]-2-dimethylamino-phenyl]-(4-bromo-phenyl)-methanone,

[4-[6-(allyl-methyl-amino)-hexyloxy]-2-hydroxy-phenyl]-(4-bromo-phenyl)-methanone,

[2-amino-4-[6-(allyl-methyl-amino)-hexyloxy]-phenyl]-(4-bromo-phenyl)-methanone as well as the following compounds:

(E)-(4-bromo-phenyl)-[2,5-difluoro-4-(4-dimethylamino-but-2-enyloxy]-methanone,

[4-[6-(allyl-methyl-amino)-hexyloxy]-2,5-difluoro-phenyl]-(4-bromo-phenyl)-methanone, (E)-[4-[4-(allyl-methyl-amino)-but-2-enyloxy]-2,5-difluoro-phenyl]-(2,4-difluoro-phenyl)-methanone, (E)-[2,5-difluoro-4-(4-dimethylamino-but-2-enyloxy)-phenyl]-(2,4-difluoro-phenyl)-methanone,

[4-[6-(allyl-methyl-amino)-hexyloxy]-2,5-difluoro-phenyl]-(2,4-difluoro-phenyl)-methanone, (2,4-difluoro-phenyl)-[4-(6-dimethylamino-hexyloxy)-2,5-difluoro-phenyl]methanone, (E)-[4-[4-(allyl-methyl-amino)-but-2-enyloxy]-2,3,5,6-tetrafluoro-phenyl]-(4-bromo-phenyl]-methanone, (E)-[4-[4-(allyl-methyl-amino)-but-2-enyloxy]-3-fluoro-2-methyl-phenyl]-(4-bromo-phenyl)-methanone, (E)-[4-[4-(allyl-methyl-amino)-but-2-enyloxy]-2-methylsulphanyl-phenyl]-(4-bromo-phenyl)-methanone, (E)-N-[11-[4-[4-(allyl-methyl-amino)-but-2-enyloxy]-3-fluoro-phenyl]-1-oxo-undecyl]-acetamide, (E)-[4-(4-allyl-methyl-amino-but-2-enyloxy)-2-hydroxy-phenyl]-(4-bromo-phenyl)-methanone, (E)-1-[4-[4-(allyl-methyl-amino)-but-2-enyloxy]-3-fluoro-phenyl]-11-amino-undecan-1-one, (E)-1-[4-[(E)-4-(allyl-methyl-amino)-but-2-enyloxy]-3-fluoro-phenyl]-2-[(E)-3,7-dimethyl-octa-2,6-dienyl]-5,9-dimethyl-deca-4,8-dien-1-one, (E)-1-[4-[4-(allyl-methyl-amino)-but-2-enyloxy]-3-fluoro-phenyl]-5-methyl-2-(3-methyl-but-2-enyl)-hex-4-en-1-one, (E)-(RS)-1-[4-[4-(allyl-methyl-amino)-but-2-enyloxy]-3-fluoro-phenyl]-3-hydroxy-5-methyl-hex-4-en-1-one, (E)-(RS)-1-[4-[4-(allyl-methyl-amino)-but-2-enyloxy]-2-fluoro-phenyl]-3-hydroxy-5-methyl-hex-4-en-1-one, (E)-(RS)-1-[4-[4-(allyl-methyl-amino)-but-2-enyloxy]-phenyl]-3-hydroxy-5-methyl-hex-4-en-1-one, (E)-(RS)-1-[4-[(E)-4-(allyl-methyl-amino)-but-2-enyloxy]-3-fluoro-phenyl]-3-hydroxy-5,9-dimethyl-deca-4,8-dien-1-one, (E)-(RS)-13-(allyl-methyl-amino)-1-[4-[4-(allyl-methyl-amino)-but-2-enyloxy]-3-fluoro-phenyl]-3-hydroxy-tridecan-1-one, (E)-1-[4-[(E)-4-(allyl-methyl-amino)-but-2-enyloxy]-3-fluoro-phenyl]-5-methyl-hexa-2,4-dien-1-one, (E)-13-(allyl-methyl-amino)-1-[4-[(E)-4-(allyl-methyl-amino)-but-2-enyloxy]-3-fluoro-phenyl]-tridec-2-en-1-one, (E)-1-[4-[(E)-4-(allyl-methyl-amino)-but-2-enyloxy]-2-fluoro-phenyl]-5-methyl-hexa-2,4-dien-1-one, (E)-1-[4-[(E)-4-(allyl-methyl-amino)-but-2-enyloxy]-phenyl]-5-methyl-hexa-2,4-dien-1-one, (2E,4E)-1-[4-[(E)-4-(allyl-methyl-amino)-but-2-enyloxy]-3-fluoro-phenyl]-5,9-dimethyl-deca-2,4,8-trien-1-one,

[4-[6-(allyl-methyl-amino)-hexyloxy]-2-1H-[1,2,4]triazol-1-yl-phenyl]-(4-bromo-phenyl)-methanone, 1-[4-[6-(allyl-methyl-amino)-hexyloxy]-2-methylamino-pheny]- 4-methyl-hex-5-en-1-one, (E)-1-[4-[4-(allyl-methyl-amino)-but-2-enyloxy]-2-methylsulphanyl-phenyl]-5-methyl-hex-4-en-1-one, N-[5-[6-(allyl-methyl-amino)-hexyloxy]-2-(4-bromo-benzoyl)-phenyl]-methanesulphonamide, (4-bromo-phenyl)-(4'-dimethylaminomethyl-3-hydroxy-biphenyl-4-yl)-methanone, N-[5-[6-(allyl-methyl-amino)-hexyloxy]-2-(4-bromo-benzoyl)-phenyl]-formamide, D) those in which L is an alkylene or alkenylene group which has a total of up to 11 C atoms and at least 4 or, respectively, 3 C atoms between the two free valencies and which is bonded to M via MH or N-alkanoyl, especially the compounds of the formula

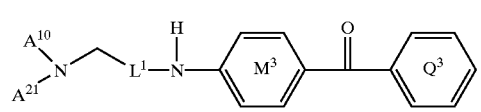

wherein $A^{10}$ is alkyl, $A^{21}$ is alkenyl, $L^1$ is alkylene or alkenylene with a total of up to 11 C atoms and at least 4 or, respectively, 3 C atoms between the two free valencies, $M^3$ is halogenated 1,4-phenylene and $Q^3$ is halogenated phenyl, especially wherein $A^{10}$ is methyl, $A^{21}$ is allyl, $L^1$ is n-pentylene or n-propenylene, $M^3$ is fluorophenylene and $Q^3$ is bromophenyl, especially:

(E)-[4-[4-(allyl-methyl-amino)-but-2-enylamino]-3-fluoro-phenyl]-(4-bromo-phenyl)-methanone,

[4-[6-(allyl-methyl-amino)-hexylamino]-3-fluoro-phenyl]-(4-bromo-phenyl)-methanone as well as the following compounds:

(E)-N-[4-(allyl-methyl-amino)-but-2-enyl]-N-[4-(4-bromo-benzoyl)-2-fluoro-phenyl]-acetamide, N-[6-(allyl-methyl-amino)-hexyl]-N-[4-(4-bromobenzoyl)-2-fluoro-phenyl]-acetamide, E) those in which M is a group of the formula

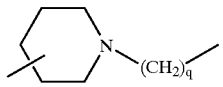
(M¹)

and q is 1 or 0, especially in which M and T together form the piperidin-1-ylsulphonyl group, especially the compounds of the formula

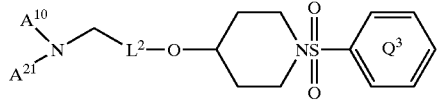
Ie wherein $A^{10}$ is alkyl, $A^{21}$ is alkenyl, $L^2$ is alkylene with up to 11 C atoms and at least 4 C atoms between the two free valencies and $Q^3$ is halogenated phenyl, especially wherein $A^{10}$ is methyl, $A^{21}$ is allyl, $L^2$ is n-pentylene and $Q^3$ is bromophenyl, especially
  allyl-[6-[1-(4-bromo-phenylsulphonyl)-piperidin-4-yloxy]-hexyl]-methyl-amine
and the compounds:
  [4-[6-(allyl-methyl-amino)-hexyloxy]-piperidin-1-yl]-1-(4-bromo-phenyl)methanone,
  2-[4-[6-(allyl-methyl-amino)-hexyloxy]-piperidin-1-yl]-1-(4-bromo-phenyl)-ethanone,
F) those in which $A^1$ is alkyl and $A^2$ is OH or alkyl optionally substituted by a group $R^1$, $CONH_2$ or CN or
  $A^1$ and $A^2$ or $A^3$ together form an alkylene, alkenylene or alkadienylene group
  $A^1$-$A^2$ or $A^1$-$A^3$ which has up to 5 C atoms and which is optionally substituted by $R^1$,
  and a C atom in a group $A^1$-$A^2$ or $A^1$-$A^3$ can be replaced by a N atom and $R^1$ is OH, oxo, alkyl(O or S) or dialkylamino bonded to a saturated C atom of $A^2$, $A^1$-$A^2$ or $A^1$-$A^3$,
  provided that a C atom substituted by $R^1$ or an unsaturated C atom present in $A^2$, $A^1$-$A^2$ or $A^1$-$A^3$ must be bonded in a position other than the α-position to $N(A^1A^2)$,
especially the compounds in which $A^1$ and $A^2$ together signify alkylene which has up to 5 C atoms and which is substituted by OH as well as the compounds of the formula

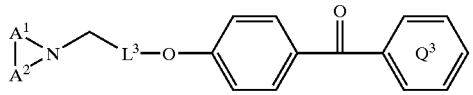
If wherein $A^1$ and $A^2$ together signify an alkylene group which has up to 5 C atoms and which is substituted by OH, $L^3$ is alkenylene with a total of up to 11 C atoms and at least 3 C atoms between the two free valencies and $Q^3$ is halogenated phenyl, especially wherein $A^1$ and $A^2$ together are 4-hydroxy-piperidin-1-yl, $L^3$ is n-propenylene and $Q^3$ is bromophenyl, especially:
  (E)-(4-bromo-phenyl)-[4-[4-(4-hydroxy-piperidin-1-yl)-but-2-enyloxy]-phenyl]-methanone
as well as the following compounds:
  cyclohexyl p-[[(E)-4-(dimethylamino)-2-butenyl]oxy]phenyl ketone, (E)-[[4-[4-(4-bromo-benzoyl)-phenoxy]-but-2-enyl]-methyl-amino]-acetonitrile,
  (E)-3-[[4-[4-(4-bromo-benzoyl)-phenoxy]-but-2-enyl]-methyl-amino]-propionitrile,
  (E)-(4-bromo-phenyl)-[4-[4-(4-dimethylamino-piperidin-1-yl)-but-2-enyloxy]-phenyl]-methanone,
  (4-bromo-phenyl)-[4-[6-(hydroxy-methyl-amino)-hexyloxy]-phenyl]-methanone,
  (E)-(4-bromo-phenyl)-[4-[4-(hydroxy-methyl-amino)-but-2-enyloxy]-phenyl]-methanone,
  (E)-(4-bromo-phenyl)-[4-[4-[(2-methoxy-ethyl)-methyl-amino]-but-2-enyloxy]-phenyl]-methanone,
  (E)-(4-bromo-phenyl)-[4-[4-[methyl-(2-methylsulphanyl-ethyl)-amino]-but-2-enyloxy]-phenyl]-methanone,
  (E)-(4-bromo-phenyl)-[4-(4-imidazol-1-yl-but-2-enyloxy)-phenyl]-methanone,
  (4-bromo-phenyl)-[4-(6-imidazol-1-yl-hexyloxy)-phenyl]-methanone,
  (4-bromo-phenyl)-[4-[6-[(3-hydroxy-propyl)-methyl-amino]-hexyloxy]-phenyl]-methanone,
  1-[[6-[4-(4-bromo-benzoyl)-phenoxy]-hexyl]-methyl-amino]-propan-2-one,
  (E)-2-[[4-[4-(4-bromo-benzoyl)-phenoxy]-but-2-enyl]-methyl-amino]-acetamide,
  (±)(4-bromo-phenyl)-[4'-(1-methylpyrrolidin-2-yl)-biphenyl-4-yl]-methanone,
G) those in which p=0 and L is $C_{6-11}$-alkenylene or $C_{6-11}$-alkadienylene bonded to T, especially the compounds of the formula

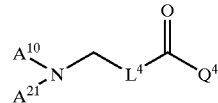
Ig wherein $A^{10}$ is alkyl, $A^{21}$ is alkenyl, $L^4$ is $C_{6-11}$-alkadienylene and $Q^4$ is an alkenyl group with 0 to 3 methyl substituents and a total of 6 to 13 C atoms, especially wherein $A^{10}$ is methyl, $A^{21}$ is allyl, $L^4$ is dimethylocta-dienylene and $Q^4$ is 4-methyl-3-pentenyl, especially:
  (9E,13E)-15-(allyl-methyl-amino)-2,9,13-trimethyl-pentadeca-2,9,13-trien-6-one
as well as the following compounds:
  (4E,8E)-10-(allyl-methyl-amino)-1-(4-bromo-phenyl)-4,8-dimethyl-deca-4,8-dien-1-one,
  (4E,8E)-1-(4-bromo-phenyl)-10-dimethylamino-4,8-dimethyl-deca-4,8-dien-1-one,
  (7E,11E)-13-(allyl-methyl-amino)-2,7,11-trimethyl-trideca-2,7,11-trien-6-one,
  (7E,11E)- and (7Z,11E)-13-(allyl-methyl-amino)-2,7,11-trimethyl-trideca-2,7,11-trien-6-one,
  (2E,6E)-8-(allyl-methyl-amino)-1-(4-bromo-phenyl)-2,6-dimethyl-octa-2,6-dien-1-one,
  (7E,11E)-13-(allyl-methyl-amino)-7,11-dimethyl-trideca-1,7,11-trien-6-one,
  (2E,6E)-(RS)-8-(allyl-methyl-amino)-1-(4-bromo-phenyl)-2,6-dimethyl-octa-2,6-dien-1-ol,
  (E)-(RS)-8-(allyl-methyl-amino)-1-(4-bromo-phenyl)-2,6-dimethyl-oct-6-en-1-one,
  (2E,6E)-(RS)-10-(allyl-methyl-amino)-1-(4-bromo-phenyl)-3,7-dimethyl-deca-2,6-dien-1-ol, (2E,6E)-(RS)-8-(allyl-methyl-amino)-1-(4-bromo-phenyl)-3,7-dimethyl-octa-2,6-dien-1-ol, (2E,6E)-10-(allyl-methyl-amino)-1-(4-bromo-phenyl)-3,7-dimethyl-deca-2,6-dien-1-one, (2E,6E)-8-(allyl-methyl-amino)-1-(4-bromo-phenyl)-3,7-dimethyl-octa-2,6-dien-1-one, H) those in which M is thienylene or pyridylene, especially the following:

(E)-1-[6-[6-(allyl-methyl-amino)-hexyloxy]-pyridin-3-yl]-5-methyl-hexa-2,4-dien-1-one, 6-[6-(allyl-methyl-amino)-hexyloxy]-pyridin-3-yl]-(4-bromo-phenyl)-methanone, (E)-[6-[4-(allyl-methyl-amino)-but-2-enyloxy]-pyridin-3-yl]-(4-bromo-phenyl)-methanone,

[5-[6-(allyl-methyl-amino)-hexyloxy]-pyridin-2-yl]-(4-bromo-phenyl)-methanone, 5-(4-[(allyl-methylamino)-methyl]-phenyl)-thiophen-2-yl)-(4-bromophenyl)-methanone, 5-(4-[dimethylamino)-methyl]-phenyl)-thiophen-2-yl)-(4-bromophenyl)-methanone, 5-(4-[(allyl-methylamino)-methyl]-phenyl)-thiophen-2-yl)-(4-(2,4-difluorophenyl))-methanone, (2-dimethylamino-4-fluoro-phenyl)-[5-(4-dimethylaminomethyl-phenyl)-thiophen-2-yl]-methanone, I) those in which L is cycloalkylene-alkylene bonded to M via an O atom, especially (1RS,2RS)-(4-bromo-phenyl)-[4-[2-[(ethyl-methyl-amino)-methyl]-cyclopropylmethoxy]-phenyl]-methanone, (1RS,2RS)-[4-[2-[(allyl-methyl-amino)-methyl]-cyclopropylmethoxy]-phenyl]-(4-bromo-phenyl)-methanone.

The invention is also concerned with a process for the manufacture of the compounds of formula I. This process comprises a) reacting a bromide of the formula

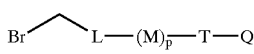

with an amine $HN(A^1,A^2)$, b) methylating an amine of the formula

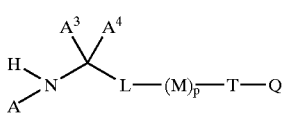

wherein A has the same significance as $A^2$, c) reacting an amine of formula III, wherein A has the same significance as $A^1$, with a halide of the formula Hal-$A^0$, wherein Hal is halogen and $A^0$ is cycloalkyl-alkyl or alkyl or alkenyl substituted by a group $R^1$, $CONH_2$ or CN, d) reacting an ethanone of the formula

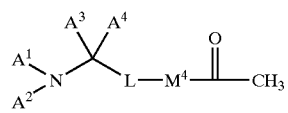

wherein $M^4$ stands for 1,4-phenylene, which can be substituted as given above for a 1,4-phenylene group M, or for thienylene or pyridylene, with a halide of the formula

Hal-$R^7$ to give a ketone of formula I in which T and Q together are a group $C(O)C(R^7)_2$ and $R^7$ has the same significance as in formula I, e) reacting an ethanone of formula IV with an aldehyde of the formula

HC(O)Q"

wherein Q" is a straight-chain alkyl, alkenyl or alkadienyl group with 0 to 3 methyl substituents and a total of 4 to 11 C atoms, f) reacting a β-hydroxyketone of the formula

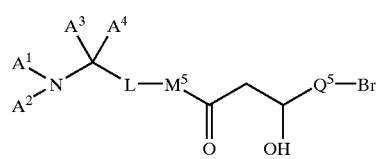

wherein $M^5$ stands for 1,4-phenylene, which can be substituted as given above for a 1,4-phenylene group M, and $Q^5$ is a divalent group corresponding to one of the above monovalent groups Q", with an amine $HN(R^9,R^{10})$, g) reacting an aminoalcohol of the formula

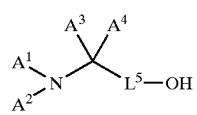

wherein $L^5$ is alkylene or alkenylene with a total of up to 11 C atoms and at least 4 or, respectively, 3 C atoms between the two free valencies or cycloalkylene-alkylene, with a compound of the formula

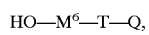

HO—$M^6$—T—Q, wherein $M^6$ stands for 1,4-phenylene, which can be substituted as given above, or for thienylene, h) reacting an aminoalcohol of formula VI with a chloride of the formula

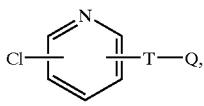
VII i) reacting an acid addition salt of an amine of the formula

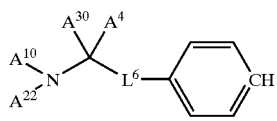
VIII wherein $A^{10}$ is alkyl, $A^{22}$ is cycloalkyl, cycloalkyl-alkyl or an alkyl group optionally substituted by a group $R^{10}$ or CN, $A^{30}$ and $A^4$ are hydrogen or alkyl or $A^{10}$ and $A^{22}$ or $A^{30}$ together form an alkylene group optionally substituted by $R^{11}$, and a C atom in such an alkylene group can be replaced by N-alkyl, $R^{11}$ is oxo, alkyl (O or S) or dialkylamino and $L^6$ is phenylene or alkylene which has a total of up to 11 C atoms and at least 4 C atoms between the two free valencies and which is bonded to the phenyl ring directly or via O or N-alkyl, with an acid chloride of the formula ClC(O)—$Q^6$ wherein $Q^6$ is cycloalkyl, $C(R^{70},R^{80})$, phenyl substituted by one or more substituents from the group of alkyl, halogen, dialkylamino, CN, $NO_2$, $CF_3$, 1,2,4-triazol-1-yl and tetrazol-1-yl or a straight-chain alkyl group with 0 to 3 methyl substituents and a total of 6 to 13 C atoms and $R^{70}$ and $R^{80}$ stand for $C_{5-11}$-alkyl, j) reacting a diamine of the formula

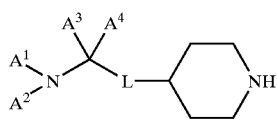
IX with a halide of the formula

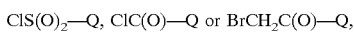
ClS(O)$_2$—Q, ClC(O)—Q or BrCH$_2$C(O)—Q, k) reacting an aldehyde of the formula

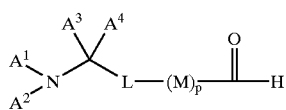
X with an agent which introduces the group Q, and Q is cycloalkyl, $C(R^7,R^8)$, phenyl substituted by one or more substituents from the group of alkyl, halogen, $N(R^{90},R^{100})$, CN, $NO_2$, $CF_3$, 1,2,4-triazol-1-yl and tetrazol-1-yl or a straight-chain alkyl, alkenyl, alkadienyl or alkatrienyl group $Q^{10}$ with 0 to 3 methyl substituents and a total of 6 to 13 C atoms, and a group $Q^{10}$ can be substituted by $N(R^{90},R^{100})$ and $R^{90}$ and $R^{100}$ are alkyl or alkenyl, l) if desired, functionally modifying reactive groups present in a compound of formula I and m) if desired, converting an amine of formula I into a physiologically compatible acid addition salt or converting an acid addition salt of a compound of formula I into the amine of formula I.

This process can be carried out in a manner known per se. Thus, reaction a) of a bromide 11 with an amine $HN(A^1,A^2)$ can be performed 1. in a solvent such as an alcohol, e.g. ethanol, or in acetone, in the presence of a base, e.g. potassium carbonate, at an elevated temperature,
2. in dimethylacetamide (DMA) at room temperature or while cooling or
3. in the presence of NaH in a solvent such as DMF while heating.

The methylation of an amine III in which A has the same significance as $A^2$ in formula I can be carried out in the presence of $NaHPO_4$ in a solvent such as an ether, e.g. dioxan, using formaldehyde while heating.

The reaction of an amine III in which A has the same significance as $A^1$ in formula I with a cycloalkyl-alkyl halide Hal-$A^0$, e.g. a bromide, can be performed in the presence of a base such as diisopropylethylamine in a solvent such as DMA while heating.

The reaction of an ethanone IV with a halide Hal-$R^7$ and/or Hal-$R^8$ leads to the corresponding aminoketone I in which T stands for CO and Q stands for the group $C(R^7,R^7)$, $C(R^8,R^8)$ and/or $C(R^7,R^8)$. The ethanone IV can be reacted firstly with a solution of lithium hexamethyldisilazide (prepared from hexamethyl-disilazane and butyllithium) in THF and then with a solution of the halide, e.g. the bromide, of the formula Hal-$R^7$ and/or Hal-$R^8$ in a solvent such as an ether, e.g. THF, at a low temperature.

Depending on whether $M^4$ in an ethanone IV stands for thienylene or optionally substituted phenylene or for pyridylene, the reaction e) of the ethanone IV with an aldehyde HC(O)Q" leads to a ketone I in which T—Q stands for C(O)CH=CH—Q" or to a O-hydroxyketone I in which T—Q stands for C(O)CH$_2$CH(OH)Q". The ethanone IV can be reacted firstly with a solution of lithium diisopropylamide (prepared from diisopropylamine and butyl-lithium) in THF and then with a solution of the aldehyde HC(O)Q" in THF at a low temperature.

Process variant f) leads to a β-hydroxyketone I in which T—Q is a group

C(O)CH$_2$CH(OH)Q$^5$—N(R$^9$,R$^{10}$).

This variant can be carried out by reacting a solution of a bromide in DMA with an amine HN(R$^9$,R$^{10}$) while cooling.

Reaction g) of an aminoalcohol VI with a compound of the formula HO—M$^6$—T—Q leads to an aminoether I in which L—M is a group L$^5$—O—M$^6$ in which L$^5$ and M$^6$ are as defined above. It can be performed by treating triphenylphosphine, the compound HO—M$^6$—T—Q and the aminoalcohol VI with diethyl azodicarboxylate in a solvent such as an ether, e.g. THF.

Reaction h) of an aminoalcohol VI with a chloride VII leads to an ether I in which L—M is a group L$^5$—O-pyridylene. It can be carried out in the presence of a base such as KOH and $K_2CO_3$ in the presence of a crown ether such as dicyclohexano-[18]-crown-6 in a solvent such as toluene while heating.

Reaction i) of an acid addition salt of the amine VII with an acid chloride ClC(O)—$Q^6$ leads to the corresponding aminoketone I in which T—Q stands for C(O)—$Q^6$. It can be performed in the presence of aluminium chloride in carbon disulphide while heating.

Reaction j) of a diamine IX with a halide ClS(O)$_2$—Q, ClC(O)—Q or BrCH$_2$C(O)—Q leads to the corresponding amine I in which T—Q stands for S(O)$_2$—Q, C(O)—Q or, respectively, CH$_2$C(O)—Q. It can be carried out in a solvent such as methylene chloride in the presence of di-isopropylethylamine (Hünig base).

Process variant k) can be a Grignard reaction between an aldehyde X and a halide such as Q—MgBr. Where Q is optionally substituted phenyl, a halide such as Q—Br in THF can firstly be reacted with butyllithium in hexane and the resulting compound Li—Q can be reacted with an aldehyde X at a low temperature such as about −78° C. to give the corresponding ketone I.

The following can be mentioned as functional transformations of reactive groups present in a compound I:

a) The transformation of a cyano group which is present as a substituent on an alkyl group A$^2$ and/or a phenyl group Q into the carbamoyl group can be carried out using a hydrogen peroxide solution in the presence of potassium carbonate in DMSO at about 0° C.

b) The hydrolysis of an alkanoylamino group which is present as a substituent on a group Q' to the amino group can be effected using hydrochloric acid in ethanol.

c) The dehydration of a β-hydroxyketone I in which T stands for C(O) and Q is a hydroxylated group Q' in the β-position to C(O) to the corresponding ketone I in which Q is an unsaturated group Q' in the α-position to C(O) can be carried out using p-toluenesulphonic acid in toluene.

d) An amide I in which L is bonded to M via N(alkanoyl) can be converted into the corresponding amine I in which L is bonded to M via NH using a solution of KOH in ethanol.

e) A group CH═CH which is present in L and which is in the α-position to the carbonyl group T in a ketone I in which p=0, the group T—Q is substituted benzoyl and L is alkenylene or alkadienylene can be selectively hydrogenated to CH$_2$CH$_2$. The hydrogenation can be carried out in benzene with a phase transfer catalyst such as tricaprylmethylammonium chloride in the presence of an aqueous solution of sodium hydrogen carbonate and sodium dithionite.

f) A fluorine atom in a benzophenone I in which Q is substituted phenyl and the phenylene group M in the o-position to the carbonyl group T is substituted by fluorine can be 1) converted into the amino group by reaction with methoxybenzylamine in the presence of a base such as potassium carbonate in toluene and subsequent reaction with trifluoroacetic acid, 2) converted into an alkylated or alkenylated amino group or into a 1,2,4-triazol-1-yl or tetrazol-1-yl group by reaction in DMA with an appropriate amine in ethanol or 3) converted into the corresponding alkoxy group or alkylthio group by reaction with a sodium alkanolate or a sodium thioalkanolate in methanol or in tetrahydrofuran.

g) An alkoxy substituent in group M can be converted into the hydroxy group by ether cleavage using aqueous acetic acid/HBr solution.

h) The amino group in a compound I in which M is aminophenylene can be converted into the alkylsulphonylamino group by reaction in methylene chloride with an alkylsulphonyl chloride. The amino group can be converted into the formylamino group using formic acid and formamide.

i) A ketone I in which T is carbonyl can be converted in a manner known per se into the corresponding alcohol in which T is a group [alkyl, alkenyl, alkynyl or cycloalkyl]—C(OH). Thus, in order to convert the carbonyl group into the C(CH$_3$)OH group, the ketone I can be reacted with LiCH$_3$/CeCl$_3$ in THF at about −78° C. and in order to convert the carbonyl group into an alkenyl-C(OH) group the ketone I can be reacted with a solution of an alkenylmagnesium halide at about 0° C. in THF/ether.

j) An oxime I in which T stands for C═N(OR$^6$) can be obtained from an acid addition salt of a ketone I in which T is carbonyl by reaction with H$_2$N(OR$_6$) in the presence of sodium acetate in ethanol while heating.

k) An alcohol I in which T is the CH(OH) group can be fluorinated to the fluoride I in which T is the CHF group using diethylamino-sulphur trifluoride in methylene chloride at about −78° C. or can be oxidized to the ketone in which T is C(O) using manganese(IV) oxide in the presence of sodium carbonate.

The starting materials II to X used in the above process and the educts required for their preparation are known or can be prepared in analogy to structurally related compounds or in a manner known per se as described in the following Examples.

Thus, a bromide II in which T stands for C(O) and L is bonded to an optionally substituted phenyl group M via a O atom is prepared starting from an ether H$_3$C—O—M and an acid chloride ClC(O)—Q via the ether H$_3$C—O—M—C(O)—Q and the corresponding phenol HO—M—C(O)—Q and reaction of this phenol with a dibromide BrCH$_2$—L—Br. Bromides II in which T stands for C(OH, alkyl), C═CH$_2$ or C(CH$_2$CH$_2$) can be prepared analogously via the corresponding phenols HO—M—T—Q.

A bromide II in which T stands for C(O) and L is bonded to an optionally substituted phenyl group M via a N(alkanoyl) group can be prepared starting from a bromide of the formula alkanoyl-NH—M—Br and from a compound of the formula N(CH$_3$, OCH$_3$)C(O)—Q via the compound of the formula alkanoyl-NH—M—C(O)—Q and reaction of this compound with a dibromide BrCH$_2$—L—Br.

A compound II in which L is phenylene bonded to a thienylene group M is obtained from bromotoluene and bromothiophene via tolyl-thiophene and tolyl-thienylene-C(O)—Q.

In general, a bromide II can be prepared from the corresponding tetrahydropyranyl ether by reaction with triphenylphosphine dibromide in methylene chloride at about −50° C. while cooling, preferably −50 to 0° C.

For the preparation of a starting amine III in which A$^3$ and A$^4$ stand for H, a corresponding bromide II can be converted with a trifluoroacetamide F$_3$C—C(O)—NH—A into F$_3$C—C(O)—N(A)—CH$_2$—L—(M)$_p$—T—Q and the trifluoroacetyl group can be cleaved off hydrolytically from the latter.

An amine starting material III for process variant c) is obtained from the corresponding bromide II via the corresponding azide and the compounds F$_3$C—C(O)—NH—CH$_2$—L—(M)$_p$—T—Q and F$_3$C—C(O)—N(A)—CH$_2$—L—(M)$_p$—T—Q.

Ethanones IV in which A$^3$ and A$^4$ stand for H are obtained by reacting a bromide BrCH$_2$—L—M$^4$—C(O)—CH$_3$ with an amine (A$^1$,A$^2$)NH in DMA.

A β-hydroxyketone V can be prepared from the corresponding ethanone IV and an aldehyde HC(O)—Q$^5$—Br.

An aminoalcohol VI in which A$^3$ and A$^4$ stand for H and L$^5$ stands for cycloalkylene-alkylene can be obtained from a diester of the formula alkyl-O—C(O)-cycloalkylene-C(O)O-alkyl via A$^2$—NH—C(O)-cycloalkylene-C(O)O-alkyl and via (A$^1$,A$^2$)—N—C(O)-cycloalkylene-COO-alkyl and reduction of this amidoester to the aminoalcohol VI: (A$^1$, A$^2$)N—CH$_2$-cycloalkylene-CH$_2$OH.

A chloride VII in which T stands for C(O) is obtained from the corresponding chloropyridinecarboxylic acid via chloro-N-methoxy-N-methylpyridinecarboxamide.

An amine VIII in which $A^{10}$ and $A^{22}$ together form an alkylene group can be prepared starting from a bromide Br—$L^6$–$C_6H_5$. This can be converted e.g. with 5-methoxy-2H-3,4-dihydropyrrole into the 2H-3,4-dihydropyrrole which is substituted by —$L^6$–$C_6H_5$ in the 5-position, the latter can be hydrogenated to the pyrrolidine which is correspondingly substituted in the 2-position and this can be methylated to the compound VIII in which $(A^{10},A^{22})$NC $(A^{30},A^4)$ is N-methyl-2-pyrrolidinyl.

A diamine of formula IX in which $A^3$ and $A^4$ stand for H and L is alkenylene bonded to the piperidine ring via O is obtained from tert-butyl 4-hydroxy-piperidine-1-carboxylate via the piperidine which is substituted by a group Br-alkylene-O— in the 4-position.

An aldehyde X in which $A^3$ and $A^4$ stand for H is obtained starting from an aldehyde H—C(O)—L—$(M)_p$—$CH_2$—O—THP via the amide of the formula $(A^1,A^2)$NC(O)—L—$(M)_p$—$CH_2$—O-THP and the aminoalcohol of the formula $(A^1,A^2)$NCH$_2$—L—$(M)_p$—$CH_2$OH by oxidation of the latter.

The preparation of some of the starting materials and intermediates referred to above is described in Examples A to G hereinafter.

A) Starting Materials of the Formula HO—M—C(O)—Q

Aa) A solution of 5.6 ml of 2-fluoroanisole in 60 ml of absolute THF is cooled to −78° C. and treated within 15 min. with 31.3 ml of 1.6M butyllithium in hexane. After 15 min. 8.7 g of 1,1,4,7,7-pentamethyldiethylenetriamine are added dropwise and, after a further 2 hrs. at −78° C., 9.4 ml of methyl iodide are added dropwise. The mixture is stirred at −78° C. overnight, then evaporated and taken up in ether/1N hydrochloric acid. The aqueous phase is extracted with ether and the organic phase is dried over sodium sulphate and evaporated in order to give crude 2-fluoro-3-methyl-anisole. 30 ml of nitrobenzene are cooled in an ice bath and then treated in succession with 8.1 g of aluminium chloride and 11.9 g of 4-bromobenzoyl chloride in 9 ml of nitrobenzene at a maximum 6° C. The mixture is stirred and then the 2-fluoro-3-methyl-anisole is added in such a manner that the temperature does not rise above 6° C. The solution is left to warm to room temperature overnight, poured into ice-water/ethyl acetate and washed with 10% aqueous sodium chloride solution, dried and concentrated. After chromatography over silica gel with hexane/ether (95/5) as the eluent and crystallization from hexane there are obtained 4.0 g of (4-bromo-phenyl)-(3-fluoro-4-methoxy-2-methyl-phenyl)-methanone, m.p. 93–95° C.

Ab) 0.5 ml of oxalyl chloride is added to a solution of 1.2 g of 11-acetylamino-undecanoic acid and 5 drops of DMF in 15 ml of methylene chloride at 0° C. and the mixture is stirred at RT for 3 hrs. The solution of the 11-acetylamino-undecanoyl chloride is treated under argon with 0.6 g of 2-fluoroanisole, cooled to −15° C. and treated with 1.4 g of aluminium chloride. After 2 hrs. at −15° C. the mixture is left to warm to room temperature overnight. The solution is treated with 15 ml of 1M hydrochloric acid at 0° C. and then with 20 ml of water. The organic phase is separated and washed with 1M hydrochloric acid, with water and with saturated sodium bicarbonate solution, dried and concentrated. 1.8 g of N-[11-(3-fluoro-4-methoxy-phenyl)-11-oxo-undecyl]acetamide are obtained.

A suspension of 21.1 g of this product in 120 ml of glacial acetic acid and 80 ml of 62% aqueous HBr solution is boiled under reflux, then concentrated and evaporated with toluene. The mixture is dissolved in 240 ml of methylene chloride and 7.3 ml of N-methylmorpholine and peracetylated at 0° C. with 6.9 ml of acetic acid and 24.2 g of N-(3-dimethylaminopropyl)-N'-ethylcarbodiimide hydrochloride. After working up with methylene chloride/0% potassium hydrogen sulphate solution drying of the organic phase and evaporation the residue is dissolved in 150 ml of methanol and stirred at room temperature with 11.1 ml of 5.4M sodium methanolate. The solution is concentrated, taken up in methylene chloride and washed with 8% phosphoric acid solution, saturated sodium bicarbonate solution and 10% sodium chloride solution. After drying there are obtained 17.0 g of N-[11-(3-fluoro-4-hydroxy-phenyl)-11-oxo-undecyl]-acetamide, MS: m/e 337 (M).

B) Starting Material $H_3C$—O—M—C(O)—Q

A solution of 5.4 g of 2,3,5,6-tetrafluoro-anisole in 80 ml of absolute THF is cooled to −78° C. and treated with 20.6 ml of 1.6M butyllithium in hexane within 15 min. After 20 min. 7.4 g of 4-bromo-N-methoxy-N-methylbenzamide (prepared from 4-bromo-benzoyl chloride and N,O-dimethylhydoxylamine, hydrochloride with N-methylmorpholine as the base) in 10 ml of THF are added dropwise and the mixture is stirred at −78° C. for 2 hrs. The reaction solution is poured into cold 10% potassium hydrogen sulphate solution/ethyl acetate and the organic phase is washed with water and 10% sodium chloride solution and dried. After crystallization from cyclohexane there are obtained 5.8 g of (4-bromo-phenyl)-(2,3,5,6-tetrafluoro-4-methoxy-phenyl)-methanone, m.p. 80–82° C.

C) Starting Material $H_3C$—O—M—C(O)—Q 1.45 g of NaSCH$_3$ (95%) are suspended in 80 ml of THF and treated with a solution of 5.51 g of (4-bromo-phenyl)-(2-fluoro-4-methoxy-phenyl)-methanone in 100 ml of THF over a period of 1.5 h. The solution is stirred at RT, again treated with 264 mg of NaSCH$_3$ and stirred for 18 h. The mixture is treated with 50 ml of sat. NH$_4$Cl solution and then 100 ml of sat. NaHCO$_3$ solution. The phases are separated, the inorganic phase is extracted with CH$_2$Cl$_2$ and the organic phase is washed with sat. NaHCO$_3$ solution and with saturated sodium chloride solution and dried. The crude product is purified on silica gel with ethyl acetate:hexane 1:2 as the eluent. 5.88 g of (4-bromo-phenyl)-(4-methoxy-2-methylsulphanyl-phenyl)-methanone are obtained as a yellow oil.

D) Starting Material HO—M—C(O)—Q

A solution of 52.0 ml of diisopropylamine in 600 ml of THF is treated dropwise at 0° C. with 230 ml of 1.6M butyllithium in hexane. After 1.5 hrs. at 0° C. the mixture is cooled to −78° C. and 26.8 g of 2-fluoro-4-hydroxyacetophenone in 120 ml of THF are added dropwise. After 1 hr. at −78° C. 23.7 ml of 3,3-dimethyl-allyl bromide in 24 ml of THF are added dropwise. The mixture is left to warm to room temperature, whereupon 34 ml of acetic acid in 100 ml of ether are sprayed in at −78° C. The solution is poured into saturated ammonium chloride solution/ether and washed with 10% sodium chloride solution. After drying and evaporation of the organic phase 33.8 g of 1-(2-fluoro-4-hydroxy-phenyl)-5-methyl-hex-4-en-1-one, m.p. 100–101° C., are obtained from ether/pentane.

E) Starting Materials of the Formula HO—M—T—Q

Ea) A mixture of 2.77 g of 4-hydroxyphenyl-(4-bromo-phenyl)-methanone and 50 ml of hexamethyldisilazane is heated under reflux for 4 h., then concentrated and dried. The resulting 4-trimethylsilyloxyphenyl-(4-bromo-phenyl)-methanone is dissolved in 60 ml of toluene and treated at room temperature under argon with 11 ml of methylmagnesium chloride solution (22% in THF). The mixture is boiled under reflux. After cooling the mixture is treated with saturated aqueous ammonium chloride solution and extracted with ethyl acetate. The organic phases are washed with saturated sodium chloride solution and dried. After evaporation of the ethyl acetate extracts there are obtained 3.36 g of (RS)-4-[1-(4-bromo-phenyl)-1-hydroxy-ethyl]-phenol, MS: m/e 293 (M+H$^+$, 1Br).

Eb) 30.2 ml of 15% vinylmagnesium chloride solution in THF are added dropwise at 0° C. to a solution of 5.58 g of 4-trimethylsilyloxyphenyl-(4-bromo-phenyl)-methanone in 80 ml of toluene. The mixture is stirred at 0° C. for 2 h., then at room temperature for 2 h., subsequently hydrolyzed with 40 ml of ammonium chloride solution and extracted with methylene chloride. The extracts are dried, evaporated and purified over silica gel with toluene-acetone as the eluent. There are obtained 2.8 g of (RS)-4-[1-(4-bromo-phenyl)-1-hydroxy-allyl]-phenol, MS: m/e 304 (M+H$^+$, 1Br).

Ec) (RS)4-[1-(4-Bromo-phenyl)-1-hydroxy-cyclopropyl-methyl]-phenol, MS: m/e 300 (M-H$_2$O, 1Br), is obtained analogously to Eb) from a solution of 4-trimethylsilyloxyphenyl-(4-bromo-phenyl)-methanone and cyclopropylmagnesium bromide, which has previously been prepared from bromocyclopropane and magnesium in ether.

Ed) 4 ml of trifluoromethyltrimethylsilane are added to a a solution of 3.1 g of 4-trimethylsilyloxyphenyl-(4-bromo-phenyl)-methanone in 60 ml of THF at 0° C. under argon. After stirring at 0° C. for 30 min. 69.3 ml of 1M tetrabutylammonium fluoride solution in THF are added dropwise. The reaction mixture is warmed to room temperature and stirred, subsequently treated with 40 ml of water, again stirred and then extracted with methylene chloride. The extracts are washed with saturated sodium chloride solution, dried and evaporated. The crude product is purified over silica gel with toluene/acetone (98:2) as the eluent. 3.0 g of (RS)4-[1-(4-bromo-phenyl)-2,2,2-trifluoro-1-hydroxyl-ethyl]-phenol, MS: m/e 290 (M-CO, 1Br), are obtained.

Ef) 6.6 g of (RS)-4-[1-(4-bromo-phenyl)-1-hydroxy-ethyl]-phenol (Ex. Ea) are dissolved in 50 ml of ethanol, boiled under reflux with 0.34 g of p-toluenesulphonic acid and then evaporated at 30° C. The residue is treated with 150 ml of saturated sodium carbonate solution and extracted with ethyl acetate. The organic phases are washed with saturated sodium chloride solution, dried and evaporated. Purification on silica gel with ethyl acetate-hexane (20:80) as the eluent gives 4.1 g of 4-[1-(4-bromo-phenyl)-vinyl]-phenol MS: m/e 274 (M+H$^+$, 1Br).

Eg) A mixture of 457 mg of zinc dust and 692 mg of CuCl in 15 ml of ether is heated under reflux under argon. Subsequently, a solution of 934 mg of [4-[1-(4-bromo-phenyl)-vinyl]-phenoxy]-trimethyl-silane in 15 ml of ether, prepared from 748 mg of 4-[1-(4-bromo-phenyl)-vinyl]-phenol (Ex. Ef) and 14 ml of hexamethyldisilazane under reflux, is added dropwise and thereafter 0.56 ml of methylene iodide is added. The reaction mixture is heated under reflux and diluted with ether. The residue is washed with ether and the filtrate is washed with water, dried and concentrated. The crude product is purified over silica gel with ethyl acetate-hexane as the eluent. 4-(1-(4-Bromo-phenyl)-cyclopropyl)-phenol is obtained as a brown oil, MS: m/e 288 (M+H$^+$, 1Br).

F) The following intermediates are obtained analogously to Example 3 hereinafter:

a) from 3-fluoro-4-hydroxy-acetophenone, (E)-1,4-dibromo-2-butene and N-allyl-methyl-amine there is obtained (E)-1-[4-[4-(allyl-methyl-amino)-but-2-enyloxy]-3-fluoro-phenyl]-ethanone, MS: m/e 278 (M+H$^+$)

b) from 2-fluoro-4-hydroxy-acetophenone, (E)-1,4-dibromo-2-butene and N-allyl-methyl-amine there is obtained (E)-1-[4-[4-(allyl-methyl-amino)-but-2-enyloxy]-2-fluoro-phenyl]-ethanone, MS: m/e 278 (M+H$^+$).

c) from 4-hydroxy-acetophenone, (E)-1,4-dibromo-2-butene and N-allyl-methyl-amine there is obtained (E)-1-[4-[4-(allyl-methyl-amino)-but-2-enyloxy]-phenyl]-ethanone, MS: m/e 260 (M+H$^+$)

d) from 1-(2-fluoro-4-hydroxy-phenyl)-5-methyl-hex-4-en-1-one (Ex. D), (E)-1,4-dibromo-2-butene and N-allyl-methyl-amine there is obtained (E)-1-[4-[(E)-4-(allyl-methyl-amino)-but-2-enyloxy]-2-fluoro-phenyl]-5-methyl-4-hexen-1-one, which is converted into the fumarate (1:1), MS: m/e 345 (M)

e) from 1-(2-fluoro-4-hydroxy-phenyl)-5-methyl-hex-4-en-1-one (Ex. D), 1,6-dibromohexane and N-allyl-methyl-amine there is obtained 1-[4-[6-(allyl-methyl-amino)-hexyloxy]-2-fluoro-pheny]-5-methyl-hex-5-en-1-one, which is converted into the fumarate (1:1), MS: m/e 375 (M), f) From [4-(6-bromo-hexyloxy)-phenyl]-(4-bromo-phenyl)-methanone and 3-aminopropanol there is obtained (4-bromo-phenyl)-[4-[6-[(3-hydroxy-propyl)-amino]-hexyloxy]-phenyl]-methanone, MS: m/e 434 (M+H$^+$, 1Br).

G) 490 mg of 6-(allyl-methyl-amino)-hexan-1-ol (Ex. 42.B) in 5 ml of THF are treated over a period of 1.5 h. with 240 mg of NaH (55–60% dispersion in mineral oil) and with 410 mg of 1-(6-chloro-pyridin-3-yl)-ethanone (Ex. 42.D.a) in 4 ml of THF. The solution is stirred at RT, treated with water and filtered and the residue is washed with methylene chloride. The phases are separated and the inorganic phase is extracted with methylene chloride and then with ethyl acetate. The organic phases are concentrated, taken up in methylene chloride and extracted with 1M HCl. The acidic-aqueous phase is washed with methylene chloride, made basic with NaOH and extracted with methylene chloride. The organic phase is washed with NaHCO$_3$ solution and saturated sodium chloride solution and dried. The crude product is purified on silica gel with methylene chloride:methanol (9:1). 177.8 mg of 1-[6-[6-(allyl-methyl-amino)-hexyloxy]-pyridin-3-yl]-ethanone are obtained as an oil. 176.4 mg of this are converted with 70 mg of fumaric acid into 1-[6-[6-(allyl-methyl-amino)-hexyloxy]pyridin-3-yl]-ethanone-fumarate (1:1), MS: m/e 291 (M+H$^+$).

The invention is also concerned with the compounds of formula I and their salts for use as therapeutically active substances, antimycotically-active and cholesterol-lowering medicaments containing a compound of formula I or a salt thereof as the active ingredient, if desired together with a therapeutically inert carrier, as well as the use of the compounds of formula I and the salts thereof for the production of the aforementioned medicaments.

Cholesterol is a major component of atherosclerotic plaques. The connection between coronary heart disease (CHD) and high LDL cholesterol concentrations in plasma (LDL=low density lipoproteins) and the therapeutic advantage of lowering elevated LDL concentrations are today generally recognized (Gotto et al., Circulation 81, 1990, 1721–1733; Stein et al., Nutr. Metab. Cardiovasc. Dis. 2, 1992, 113–156). Atherosclerotic plaques can grow and lead to occlusion of blood vessels resulting in an ischaemia or an infarct. Studies with respect to primary prophylaxis have shown that a lowering of the LDL concentrations in plasma reduces the frequency of non-fatal incidences of CHD, while the overall morbidity remains unchanged. The lowering of the LDL cholesterol level in plasma of patients with clinically confirmed CHD (secondary intervention) reduces the CHD-mediated mortality and morbidity; the metaanalysis of different studies shows that this decrease is proportional to the reduction of the LDL cholesterol.

The clinical advantage of cholesterol lowering is even greater for patients with confirmed CHD than for asymptomatic persons with hypercholesterolemia. For the majority of patients who had survived a myocardial infarct as well as for patients suffering from angina pectoris or another atherosclerotic disease treatment with a lipid lowering agent is advisable, in which case a LDL cholesterol concentration of 2.6 mmol/l should be striven for.

Preparations such as cholanic acid sequestrating preparations, fibrate, nicotinic acid, probucol as well as the statins (HMG-Co-A reductase inhibitors) such as lovastatin and simvastatin are used for usual standard therapies. A new cholesterol-lowering medicament would be of considerable benefit for CHD patients having a high LDL cholesterol level and in which the striven-for value of 2.5 to 3.0 mmol/l can not be achieved with statins.

Further, the statins have undesired side effects. They inhibit cholesterol production in an early phase of the synthesis cascade, with the formation of non-sterolic isoprenoids also being inhibited. The latter are indispensable for cell functions. The regulation of the cell cycle, the modification of albumins and the transport of electrons in the carbon dioxide chain can therefore be influenced by statins.

For this reason a number of experiments have been undertaken to find plasma-cholesterol lowering medicaments which inhibit the cholesterol synthesis on the one hand after the farnesyl-pyrophosphate stage in order not to inhibit the formation of non-sterolic isoprenoids and on the other hand prior to lanosterol in order to avoid an accumulation of sterol intermediates. The compounds described in European Patent Application No. 636 367, which inhibit 2,3oxidosqualene-lanosterol cyclase (OSC) and which lower the total cholesterol in plasma, belong to these substances.

The present compounds of formula I inhibit cholesterol synthesis and reduce the total cholesterol in plasma. They can therefore be used in the therapy and prophylaxis of hypercholesterolemia, hyperlipemia and arteriosclerosis. In contrast to known compounds they are tolerated better and are more active. Further, they can be used in the therapy of mycoses and hyperproliferative disorders. The following tests were carried out in order to verify the activity of the compounds of formula I and their salts.

Inhibition of Human Liver Microsomal 2,3-Oxidosqualene-lanosterol Cyclase (OSC)

Liver microsomes from a healthy volunteer were prepared in sodium phosphate buffer (pH 7.4). The OSC activity was measured in the same buffer which also contained 1 mM EDTA and 1 mM dithiothreitol. The microsomes were diluted to 0.8 mg/ml protein in cold phosphate buffer. Dry [$^{14}$C]R,S-monooxidosqualene (MOS; 12.8 mCi/mmol) was diluted to 20 nCi/µl with ethanol and mixed with phosphate buffer-1% BSA (Bovine Serum Albumin). A stock solution of 1 mM test substance in DMSO was diluted to the desired concentration with phosphate buffer-1% BSA. 40 µl of microsomes were mixed with 20 µl of the solution of the test substance and the reaction was subsequently started with 20 µl of the [$^{14}$C]R,S-MOS solution. The final conditions were: 0.4 mg/ml of microsomal proteins and 30 µl of [$^{14}$C]R,S-MOS in phosphate buffer, pH 7.4, containing 0.5% albumin, DMSO <0.1% and ethanol <2%, in a total volume of 80 µl.

After 1 hour at 37° C. the reaction was stopped by the addition of 0.6 ml of 10% KOH-methanol, 0.7 ml of water and 0.1 ml of hexane:ether (1:1, v/v) which contained 25 µg of non-radioactive MOS and 25 µg of lanosterol as the carrier. After shaking 1 ml of hexane:ether (1:1, v/v) was added to each test tube, these were again shaken and then centrifuged. The upper phase was transferred into a glass test tube, the lower phase was again extracted with hexane:ether and combined with the first extract. The entire extract was evaporated to dryness with nitrogen and the residue was suspended in 50 µl of hexane:ether and applied to a silica gel plate. Chromatographic separation was effected in hexane:ether (1:1, v/v) as the eluent. The Rf values for the MOS substrate and the lanosterol product were 0.91 and, respectively, 0.54. After drying radioactive MOS and lanosterol were observed on the silica gel plate. The ratio of MOS to lanosterol was determined from the radioactive bands in order to determine the OSC inhibition.

The test was carried out on the one hand with a constant test substance concentration of 100 nM and the percentage OSC inhibition against controls was calculated. In addition, the test was carried out with different test substance concentrations and subsequently the IC$_{50}$ value was calculated, i.e. the concentration required to reduce the conversion of MOS into lanosterol to 50% of the control value. The results are given in the following Table:

| Product of Example No. | 1 | 21 | 2p | 3 | 8a | 8b | 8f |
|---|---|---|---|---|---|---|---|
| Inhibition of OSC (%) | 90 | 81 | 66 | 92 | 82 | 78 | 90 |
| IC$_{50}$ (nM) |  | 2.4 |  | 4.9 | 18 | 23.7 | 13.5 |
| 12 | 13a | 13b | 15 | 29 | 30 | 31 | 32a | 33 | 34a |
| 84 | 82 | 93.5 | 83 | 91 | 93 | 85 | 85 | 98 | 98 |
| 19 |  | 7.9 | 32 | 4.5 | 3.2 | 22 | 3.6 | 2.3 | 7.1 |
| 35 | 36 | 38 | 39a | 49 | 51 | 54b |
| 97 | 92 | 82 | 87 | 94 | 87.5 | 73 |
|  | 8.9 | 21 | 12.3 | 5.5 | 12.8 |  |

Cholesterol Lowering in Fat-fed Hamsters.

Male golden hamsters kept individually were pre-treated for 7 days with a diet containing grated coconut (40 cal. % fat). The animals were then divided into groups each comprising 5 animals. During the treatment the animals were maintained on the same diet. Each test substance was firstly homogenized in 9 ml of water and subsequently mixed with the milled diet. The controls received only feed converted into a paste with water. The animals were treated for 10 days with a test substance dosage of 200 µmol (about 70–120 mg/kg/ay). Blood samples (200 µl) were removed via the jugular vein under light anaesthesia on the last day of the pre-treatment and one day after the last administration of test substance. The plasma cholesterol concentration was determined using a calorimetric enzyme method. The plasma lipoproteins were separated by exclusion chromatography (Hennes et al., Science Tools, 36, 1992, 10–12). The total cholesterol was determined in each fraction using a fluorometric enzyme method (Gamble et al., J. Lipid Res., 19, 1978, 1068–1071) in order to calculate the amount of cholesterol in the LDL and HDL fractions. The activity on plasma cholesterol and LDL and HDL cholesterol, expressed in percent of the control animals, for the products of Examples 8a and 12 is reproduced in the following Table:

| Example | 8a | 12 |
| --- | --- | --- |
| Total cholesterol | −30% | −25% |
| LDL cholesterol | −51% | −54% |
| HDL cholesterol | −18% | −23% |

As already mentioned, the compounds of formula I and their pharmaceutically acceptable acid addition salts have, moreover, valuable antifungal properties. They are active against a large number of pathogenic fungi which cause topical and systemic infections, such as *Candida albicans, Cryptococcus neoformans* and *Aspergillus fumigatus*.

Antifungal Activity In Vitro

The compounds were tested for antifungal activity against *Candida albicans, Cryptococcus neoformans* and *Aspergillus fumigatus* using a microdilution method on microtitre plates (96 wells per plate). Yeast supplemented with 1% glucose and 0.25% di-potassium phosphate was used for the three fungal strains. The fungal cells were inoculated at $3 \times 10^4$ CFU (Colony Forming Unit) in 1 ml of medium per well. The medium contained increasing concentrations of test substance. After incubation at 27° C. for 24 or 48 hours the turbidity in each well was measured by a microtitre plate reader. The growth inhibition was calculated in comparison to a control (without test substance). The $IC_{50}$ value given in the following Table is the concentration of test substance at which the growth is inhibited by 50%.

| Compound of | $IC_{50}$ (mg/ml) for: | | C. neoformans | A. fumigatus |
| --- | --- | --- | --- | --- |
| | C. albicans | | | |
| Example No. | after: 24 hrs. | 48 hrs. | 48 hours | 48 hours |
| 25 | 0.32 | <0.32 | 1.00 | 0.82 |
| 26c | 0.49 | 5.70 | 2.70 | 8.40 |
| 29 | 0.71 | 21.00 | <0.32 | 0.71 |
| 36 | <0.32 | 1.10 | <0.32 | 2.40 |
| 43b | <0.32 | 5.00 | <0.32 | 6.40 |
| 48 | <0.32 | <0.32 | 0.47 | 18.00 |
| 54b | <0.32 | 6.50 | 0.69 | 6.10 |

The compounds of formula I and their pharmaceutically acceptable acid addition salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable acid addition salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants, masking agents and antioxidants come into consideration as pharmaceutical adjuvants.

The dosage of the compounds of formula I can vary within wide limits depending on the pathogenic fungi to be controlled, the age and the individual condition of the patient and the mode of administration, and will, of course, be fitted to the individual requirements in each particular case. For adult patients a daily dosage of about 0.01 g to about 4 g, especially about 0.05 g to about 2 g, comes into consideration for the prevention and control of topical and systemic infections by pathogenic fungi. For cholesterol lowering the daily dosage conveniently amounts to between 1 and 1200 mg, preferably 5 to 100 mg, for adult patients. Depending on the dosage it is convenient to administer the daily dosage in several dosage units.

The pharmaceutical preparations conveniently contain about 1–500 mg, preferably 2–200 mg, of a compound of formula I.

The following Examples illustrate the present invention in more detail. They are, however, not intended to limit its scope in any manner. All temperatures are given in degrees Celsius.

EXAMPLE 1 a) 75 ml of nitrobenzene are cooled in an ice bath and treated in succession 25 with 17.3 g of aluminium chloride and 4-bromobenzoyl chloride in 25 ml of nitrobenzene at a maximum 6° C. The mixture is stirred for 10 min., whereupon 15.7 g of 2,5-difluoroanisole are added in such a manner that the temperature does not exceed 6° C. The solution is left to warm to room temperature overnight, then poured on to ice-water and extracted with methylene chloride. The organic phase is washed with water and 10% sodium chloride solution, dried over sodium sulphate and concentrated. After crystallization from cyclohexane there are obtained 28.4 g of (4-bromo-phenyl)-(2,5-difluoro-4-methoxy-phenyl)-methanone.

b) A solution of 22.9 g of (4-bromo-phenyl)-(2,5-difluoro-4-methoxy-phenyl)-methanone in 140 ml of acetic acid and 100 ml of 62% aqueous HBr solution is boiled under reflux for 13 hrs., subsequently evaporated, re-evaporated with toluene and taken up in ethyl acetate. The inorganic phase is washed with saturated sodium hydrogen carbonate solution and 10% sodium chloride solution and dried. After crystallization from methylene chloride/ether/pentane there are obtained 20.8 g of (4-bromo-phenyl)-(2,5-difluoro-4-hydroxy-phenyl)-methanone.

c) 150 ml of 10% sodium hydroxide solution are added to a solution of 45.8 g of (E)-1,4-dibromo-2-butene, 20.8 g of (4-bromo-phenyl)-(2,5-difluoro-4-hydroxy-phenyl)-methanone and 1.2 g of tetrabutylammonium bromide in 150 ml of methylene chloride. The mixture is stirred at room temperature for 4 hrs., poured into water and extracted with ethyl acetate. The organic phase is washed with 10% sodium chloride solution, dried, filtered and evaporated. The crystal mass is purified over silica gel with methylene chloride as the eluent, with 15.3 g of (E)-[4-(4-bromo-but-2-enyloxy)-2,5-difluoro-phenyl]-(4-bromo-phenyl)-methanone being obtained.

d) The (E)-[4-(4-bromo-but-2-enyloxy)-2,5-difluoro-phenyl]-(4-bromo-phenyl)-methanone obtained above is dissolved in 170 ml of ethanol and boiled for 3 hrs. with 17.2 ml of N-allyl-methyl-amine and 12 g of potassium carbonate and concentrated, the residue is treated with water, extracted with methylene chloride, washed with 10% sodium chloride solution, dried, filtered and concentrated. The residue is dissolved in methylene chloride, cooled to 0° C. and treated with 7.2 ml of 4.8M hydrochloric acid solution in ether. Crystallization from methylene chloride/ethyl acetate gives 8.9 g of (E)-[4-[4-(allyl-methyl-amino)-but-2-enyloxy]-2,5-difluoro-phenyl]-(4-bromo-phenyl)-methanone•hydrochloride (1:1), m.p. 150° C.

EXAMPLE 2

Analogously to Example 1, a) from (E)-[4-(4-bromo-but-2-enyloxy)-2,5-difluoro-phenyl]-(4-bromo-phenyl)-methanone (Ex. 1c) and a 33% solution of dimethylamine in ethanol there is obtained (E)-(4-bromo-phenyl)-[2,5-difluoro-4-(4-dimethylamino-but-2-enyloxy]-methanone•hydrochloride (1;1), m.p. 172° C., b) from (4-bromo-phenyl)-(2,5-difluoro-4-hydroxy-phenyl)-methanone (Ex. 1b) and 1,6-dibromohexane via 4-(6-bromo-hexyloxy)-2,5-difluoro-phenyl]-(4-bromo-phenyl)-methanone, which is reacted with N-allyl-methyl-amine, there is obtained [4-[6-(allyl-methyl-amino)-hexyloxy]-2,5-difluoro-phenyl]-(4-bromo-phenyl)-methanone•hydrochloride (1:1), m.p. 134° C., c) from 2,4-difluorobenzoyl chloride and 2,5-difluoroanisole via (2,4-difluoro-phenyl)-(2,5-difluoro-4-methoxy-phenyl)-methanone, which is deprotected with hydrogen bromide and reacted with (E)-1,4-dibromo-2-butene and N-allyl-methyl-amine, there is obtained (E)-[4-[4-(allyl-methyl-amino)-but-2-enyloxy]-2,5-difluoro-phenyl]-(2,4-difluoro-phenyl)-methanone•hydrochloride (1:1), m.p. 141° C., d) from 2,4-difluorobenzoyl chloride and 2,5-difluoroanisole via (2,4-difluoro-phenyl)-(2,5-difluoro-4-methoxy-phenyl)-methanone, which is deprotected with hydrogen bromide and reacted with (E)-1,4-dibromo-2-butene and a 33% solution of dimethylamine in ethanol, there is obtained (E)-[2,5-difluoro-4-(4-dimethylamino-but-2-enyloxy)-phenyl]-(2,4-difluoro-phenyl)-methanone•hydrochloride (1:1), m.p. 159° C., e) from 2,4-difluorobenzoyl chloride and 2,5-difluoroanisole via (2,4-difluoro-phenyl)-(2,5-difluoro-4-methoxy-phenyl)-methanone, which is deprotected with hydrogen bromide and reacted with 1,6-dibromohexane and N-allyl-methyl-amine, there is obtained [4-[6-(allyl-methyl-amino)-hexyloxy]-2,5-difluoro-phenyl]-(2,4-difluoro-phenyl)-methanone•hydrochloride (1:1), MS: m/e 423 (M), f) from 2,4-difluorobenzoyl chloride and 2,5-difluoroanisole via (2,4-difluoro-phenyl)-(2,5-difluoro-4-methoxy-phenyl)-methanone, which is deprotected with hydrogen bromide and reacted with 1,6-dibromohexane and a 33% solution of dimethylamine in ethanol, there is obtained (2,4-difluoro-phenyl)-[4-(6-dimethylamino-hexyloxy)-2,5-difluoro-phenyl]methanone•hydrochloride (1:1), MS: m/e 396 (M), g) from cyclohexyl-4-hydroxyphenyl-methanone with (E)-1,4-dibromo-2-butene and a 33% solution of dimethylamine in ethanol there is obtained cyclohexyl-p-[[(E)-4-(dimethylamino)-2-butenyl]oxy]phenyl-methanone, MS: m/e 382 (M), h) from (4-bromo-phenyl)-(2,3,5,6-tetrafluoro-4-methoxy-phenyl)-methanone (Ex. B), which is deprotected with hydrogen bromide and reacted with (E)-1,4-dibromo-2-butene and N-allyl-methyl-amine, there is obtained (E)-[4-[4-(allyl-methyl-amino)-but-2-enyloxy]-2,3,5,6-tetrafluoro-phenyl]-(4-bromo-phenyl)-methanone•hydrochloride (1:1), MS: m/e 444 (M-$C_2H_5$, 1Br).

i) from (4-bromo-phenyl)-(3-fluoro-4-methoxy-2-methyl-phenyl)-methanone (Ex. Aa), which is deprotected with hydrogen bromide and reacted with (E)-1,4-dibrom-2-butene and N-allyl-methyl-amine, there is obtained (E)-[4-[4-(allyl-methyl-amino)-but-2-enyloxy]-3-fluoro-2-methyl-phenyl]-(4-bromo-phenyl)-methanone•hydrochloride (1:1), MS: m/e 432 (M+H$^+$, 1Br), j) from (E)-[4-(4-bromo-but-2-enyloxy)-phenyl]-(4-bromo-phenyl)-methanone and methylaminoacetonitrile•hydrochloride with triethylamine in ethanol there is obtained (E)-[[4-[4-(4-bromo-benzoyl)-phenoxy]-but-2-enyl]-methyl-amino]-acetonitrile which is converted into the hydrochloride, MS: m/e 399 (M+H$^+$, 1Br), k) from (E)-[4-(4-bromo-but-2-enyloxy)-phenyl]-(4-bromo-phenyl)-methanone and 3-methylaminopropionitrile there is obtained (E)-3-[[4-[4-(4-bromo-benzoyl)-phenoxy]-but-2-enyl]-methyl-amino]-propionitrile which is converted into the fumarate, MS: m/e 413 (M+H$^+$, 1Br), l) from (E)-[4-(4-bromo-but-2-enyloxy)-phenyl]-(4-bromo-phenyl)-methanone and 4-hydroxypiperidine in ethanol there is obtained (E)-(4-bromo-phenyl)-[4-[4-(4-hydroxy-piperidin-1-yl)-but-2-enyloxy]-phenyl]-methanone which is converted into the fumarate, MS: m/e 429 (M+H$^+$, 1Br), m) from (E)-[4-(4-bromo-but-2-enyloxy)-phenyl]-(4-bromo-phenyl)-methanone and 4-dimethylamino-piperidine in $CH_2Cl_2$ there is obtained (E)-(4-bromo-phenyl)-[4-[4-(4-dimethylamino-piperidin-1-yl)-but-2-enyloxy]-phenyl]-methanone, which is converted into (E)-(4-bromo-phenyl)-[4-[4-(4-dimethylamino-piperidin-1-yl)-but-2-enyloxy]-phenyl]-methanone•hydrochloride, MS: m/e 457 (M+H$^+$), n) from [4-(4-bromo-hexyloxy)-phenyl]-(4-bromo-phenyl)-methanone and N-methylhydroxylamine•hydrochloride there is obtained (4-bromo-phenyl)-[4-[6-(hydroxy-methyl-amino)-hexyloxy]-phenyl]-methanone, MS: m/e 406 (M+H$^+$, 1Br), o) from (E)-[4-(4-bromo-but-2-enyloxy)-phenyl]-(4-bromo-phenyl)-methanone and N-methylhydroxylamine•hydrochloride there is obtained (E)-(4-bromo-phenyl)-[4-[4-(hydroxy-methyl-amino)-but-2-enyloxy]-phenyl]-methanone, MS: m/e 376 (M+H$^+$, 1Br), p) from [4-(6-bromo-hexyloxy)-2-fluoro-phenyl]-(4-bromo-phenyl)-methanone and N-methylcyclopropylamine•hydrochloride there is obtained (4-bromo-phenyl)-[4-[6-(cyclopropyl-methyl-amino)-hexyloxy]-2-fluoro-phenyl]-methanone which is converted into the hydrochloride, MS: m/e 447 (M, 1Br).

EXAMPLE 3 a) 1.0 g of 4-bromo-phenyl)-(4-methoxy-2-methylsulphanyl-phenyl)-methanone (Ex. C) are suspended in 6 ml of acetic acid and 3.5 ml of 62% HBr and stirred at 125° C. overnight. The suspension is added to sat. NaHCO₃ solution, the phases are separated and the inorganic phase is extracted with ethyl acetate. The organic phases are washed with sat. NaHCO₃ solution and with saturated sodium chloride solution and dried. 920 mg of (4-bromo-phenyl)-(4-hydroxy-2-methylsulphanyl-phenyl)-methanone are obtained as brown crystals.

b) 450 mg of (4-bromo-phenyl)-(4-hydroxy-2-methylsulphanyl-phenyl)-methanone are taken up in 7 ml of acetone and treated with 1.24 g of K₂CO₃ and 530 μl of 1,6-dibromohexane. The suspension is heated under reflux overnight, cooled, filtered and concentrated. After removing the excess 1,6-dibromohexane there are obtained 710 mg of [4-[6-(bromo)-hexyloxy]-2-methyl-sulphanyl-phenyl]-(4-bromo-phenyl)-methanone as a brown oil.

c) The product from b) is taken up in 7 ml of DMA and stirred at RT overnight with 420 μl of N-allyl-methyl-amine. The mixture is concentrated and the residual oil is taken up in CH₂Cl₂, washed with sat. NaHCO₃ solution and sat. sodium chloride solution and dried. The yellow oil (506 mg), [4-[6-(allyl-methyl-amino)-hexyloxy]-2-methylsulphanyl-phenyl]-(4-bromo-phenyl)-methanone, obtained after removal and purification on silica gel with CH₂Cl₂:methanol 95:5, is taken up in ethanol and treated with 111.6 mg of fumaric acid. After stirring the solution is concentrated and the residue is taken up in ethyl acetate, concentrated and subsequently lyophilized. 695 mg of [4-[6-(allyl-methyl-amino)-hexyloxy]-2-methylsulphanyl-phenyl]-(4-bromo-phenyl)-methanone•fumarate (1:1) are obtained as a viscous oil, MS: m/e 476 (M+H⁺, 1Br).

EXAMPLE 4

Analogously to Example 3, a) from (4-bromo-phenyl)-(4-methoxy-2-methylsulphanyl-phenyl)-methanone (Ex. C) via (E)-[4-[4-(bromo)-but-2-enyloxy]-2-methylsulphanyl-phenyl]-(4-bromo-phenyl)-methanone there is obtained (E)-[4-[4-(allyl-methyl-amino)-but-2-enyloxy-2-methylsulphanyl-phenyl]-(4-bromo-phenyl)-methanone•fumarate (1:1), MS: m/e 446 (M+H⁺, 1Br), b) from (E)-[4-(4-bromo-but-2-enyloxy)-phenyl]-(4-bromo-phenyl)-methanone and (2-methoxy-ethyl)-methyl-amine there is obtained (E)-(4-bromo-phenyl)-[4-[4-[(2-methoxy-ethyl)-methyl-amino]-but-2-enyloxy]-phenyl]-methanone•fumarate (1:1), m.p. 92–98° C., c) from N-[11-(3-fluoro-4-hydroxy)-11-oxo-undecyl] acetamide (Ex. Ab), (E)-1,4-dibromo-2-butene and N-allyl-methyl-amine there is obtained (E)-N-[11-[4-[4-(allyl-methyl-amino)-but-2-enyloxy]-3-fluoro-phenyl]-11-oxo-undecyl]-acetamide•fumarate (1:1), m.p. 69–71° C., d) from 1-(2-fluoro-4-hydroxy-phenyl)-5-methyl-hex-4-en-1-one (Ex. D), 1,6-dibromohexane and cyclopropylmethyl-methylamine there is obtained 1-[4-[6-(cyclopropylmethyl-methyl-amino)-hexyloxy]-2-fluoro-phenyl]-5-methyl-hex-4-en-1-one, MS: m/e 390 (M+H⁺), e) from 1-(2-fluoro-4-hydroxy-phenyl)-5-methyl-hex-4-en-1-one (Ex. D), 1,6-dibromohexane and cyclopropyl-methylamine•hydrochloride there is obtained 1-[4-[6-(cyclopropyl-methyl-amino)-hexyloxy]-2-fluoro-phenyl]-5-methyl-hex-4-en-1-one, MS: m/e 376 (M+H⁺), f) from (4-bromo-phenyl)-(4-hydroxy-phenyl)-methanone, (E)-1,4-dibromo-2-butene and 1-methylamino-2-methylthio-ethane there is obtained (E)-(4-bromo-phenyl)-[4-[4-[methyl-(2-methylsulphanyl-ethyl)-amino]-but-2-enyloxy]-phenyl]-methanone•fumarate (1:1), MS: m/e 434 (M+H⁺, 1Br).

EXAMPLE 5

A solution of 0.88 g of (4-bromo-phenyl)-(2,4-dihydroxy-phenyl)-methanone and (E)-1,4-dibromo-2-butene in 7.5 ml of DMF and 0.56 g of lithium carbonate is stirred at 40° C. for 48 hrs. After working up with methylene chloride/0.5M hydrochloric acid and purification over silica gel with hexane/ethyl acetate (9:1) there is obtained 0.14 g of (E)-[4-(4-bromo-but-2-enyloxy)-2-hydroxy-phenyl]-(4-bromo-phenyl)-methanone which, with N-allyl-methyl-amine analogously to Example 3c), gives (E)-[4-(4-allyl-methyl-amino-but-2-enyloxy)-2-hydroxy-phenyl]-(4-bromo-phenyl)-methanone which is converted into the hydrochloride, MS: m/e 416 (M+H⁺, 1Br).

EXAMPLE 6

A solution of 68 mg of imidazole in 4 ml of DMF is added dropwise to a suspension of 44 mg of 55% sodium hydride in 4 ml of DMF. After heating the mixture to 70° C. a solution of 441 mg of (E)-[4-(4-bromo-but-2-enyloxy)-phenyl]-(4-bromo-phenyl)-methanone in 12 ml of DMF is added dropwise. Then, the mixture is stirred at 70° C. for a further 1 h. and, after cooling, poured into 5 ml of water and concentrated. The residue is treated with water and extracted with methylene chloride. The organic phases are washed with saturated sodium chloride solution, dried and evaporated. The residue is purified on silica gel with toluene/acetone/triethylamine (70:29:1). The (E)-(4-bromo-phenyl)-[4-(4-imidazol-1-yl-but-2-enyloxy)-phenyl]-methanone (140 mg) is obtained as the beige solid base which is converted into the hydrochloride, MS: m/e 397 (M, 1Br).

EXAMPLE 7

Analogously to Example 6, from 4-(6-bromohexyloxy)-phenyl]-(4-bromo-phenyl)-methanone and imidazole there is obtained (4-bromo-phenyl)-[4-(6-imidazol-1-yl-hexyloxy)-phenyl]-methanone as the white solid base which is converted into the hydrochloride, MS: m/e 427 (M+H⁺, 1Br).

EXAMPLE 8

Analogously to Example 3:

a) from (RS)-4-(1-(4-bromo-phenyl)-1-hydroxy-ethyl)-phenol (Ex. Ea), (E)-1,4-dibromo-2-butene and N-allyl-methyl-amine there is obtained (E)-(RS)-1-[4-[4-(allyl-methyl-amino)-but-2-enyloxy]-phenyl]-(4-bromo-phenyl)-ethanol which is converted into the fumarate, MS: m/e 416 (M+H⁺, 1Br).

b) from (RS)-4-(1-(4-bromo-phenyl)-1-hydroxy-allyl)-phenol (Ex. Eb), (E)-1,4-dibromo-2-butene and N-allyl-methyl-amine there is obtained (E)-(RS)-1-[4-[4-(allyl-methyl-amino)-but-2-enyloxy]-phenyl]-1-(4-bromo-phenyl)-prop-2-en-1-ol which is converted into the fumarate, MS: m/e 428 (M+H⁺, 1Br), c) from (RS)-4-(1-(4-bromo-phenyl)-1-hydroxy-cyclopropyl-methyl)-phenol (Ex. Ec), (E)-1,4-dibromo-2-butene and N-allyl-methyl-amine there is obtained (E)-(RS)-[4-[4-(allyl-methyl-amino)-but-2-enyloxy]-phenyl]-(4-bromo-phenyl)-cyclopropyl-methanol as the hydrobromide, m.p 143–144° C., d) from (RS)-4-(1-(4-bromo-phenyl)-2,2,2-trifluoro-1-hydroxyl-ethyl)-phenol (Ex. Ed), (E)-1,4-dibromo-2-butene and N-allyl-methyl-amine there is obtained (E)-

(RS)-1-[4-[4-(allyl-methyl-amino)-but-2-enyloxy]-phenyl]-1-(4-bromo-phenyl)-2,2,2-trifluoro-ethanol which is converted into the fumarate, MS: m/e 470 (M+H$^+$, 1Br), e) from (RS)-4-(1-(4-bromo-phenyl)-2,2,2-trifluoro-1-hydroxyl-ethyl)-phenol (Ex. Ed), 1,6-dibromohexane and N-allyl-methyl-amine there is obtained (RS)-1-[4-[6-(allyl-methyl-amino)-hexyloxy]-phenyl]-1-(4-bromo-phenyl)-2,2,2-trifluoro-ethanol which is converted into the fumarate, MS: m/e 500 (M+H$^+$, 1Br)., f) from (RS)4-(1-(4-bromo-phenyl)-vinyl)-phenol (Ex. Ef), (E)-1,4-dibromo-2-butene and N-allyl-methyl amine there is obtained (E)-allyl-[4-[4-[1-(4-bromo-phenyl)-vinyl]-phenoxy]-but-2-enyl]-methyl-amine which is converted into the fumarate, MS: m/e 398 (M+H$^+$, 1Br).

g) from 4-(1-(4-bromo-phenyl)-cyclopropyl)-phenol (Ex. Eg) and (E)-1,4-dibromo-2-butene via (E)-1-[4-(4-bromo-but-2-enyloxy)-phenyl]-1-(4-bromo-phenyl)-cyclopropane and reaction with N-allyl-methyl-amine there is obtained (E)-allyl-[4-[4-[1-(4-bromo-phenyl)-cyclopropyl]-phenoxy]-but-2-enyl]-methyl-amine which is converted into the fumarate, MS: m/e 412 (M+H$^+$, 1Br).

EXAMPLE 9

The two enantiomers of (E)-(RS)-1-[4-[4-(allyl-methyl-amino)-but-2-enyloxy]-phenyl]-(4-bromo-phenyl)-ethanol (Ex. 8a) are separated by supercritical fluid chromatography over silica gel coated with an amylose derivative using 30% methanol and 0.5% butylamine in $CO_2$ as the eluent. There are obtained a) (E)-(R or S)-1-[4-[4-(allyl-methyl-amino)-but-2-enyloxy]-phenyl]-(4-bromo-phenyl)-ethanol and
b) (E)-(S or R)-1-[4-[4-(allyl-methyl-amino)-but-2-enyloxy]-phenyl]-(4-bromo-phenyl)-ethanol, MS: m/e 416 (M+H$^+$, 1Br).

EXAMPLE 10

Analogously to Example 3 there is obtained allyl-[6-[4-[1-(4-bromo-phenyl)-vinyl]-3-fluoro-phenoxy]-hexyl]-methyl-amine which is converted into the fumarate, MS: m/e 423 (M, 1Br).

EXAMPLE 11

A solution of 1.84 g of (E)-N-[11-[4-[4-(allyl-methyl-amino)-but-2-enyloxy]-3-fluoro-phenyl]-11-oxo-undecyl]-acetamide (Ex. 4c) in 30 ml of ethanol/5 ml of 18% aqueous hydrochloric acid is boiled for 7 hrs. and, after the addition of 4 ml of concentrated hydrochloric acid, boiled for 24 hrs. and, after the addition of a further 4 ml of concentrated hydrochloric acid, boiled for 30 hrs. After concentration the residue is taken up in 10% potassium hydrogen sulphate solution/methylene chloride and the aqueous phase is made basic with 10% sodium hydroxide solution and extracted with methylene chloride. The organic phase is dried and concentrated. There are obtained 1.48 g of (E)-1-[4-[4-(allyl-methyl-amino)-but-2-enyloxy]-3-fluoro-phenyl]-11-amino-undecan-1-one which is converted into the fumarate, MS: m/e 419 (M+H$^+$).

EXAMPLE 12 a) A suspension of 10 g of (E)-[4-(4-bromo-but-2-enyloxy)-phenyl]-(4-bromo-phenyl)-methanone, 7.47 g of N-cyclopropyl-2,2,2-trifluoro-acetamide, 6.7 g of potassium carbonate and 0.55 g of benzyltriethylammonium bromide in 200 ml of acetonitrile is heated to boiling while stirring for 7 h. After cooling to room temperature the suspension is filtered. The filtrate is concentrated and the residue is dissolved in a mixture of 500 ml of melthylene chloride and 50 ml of methanol and stirred with 50 g of a strongly acidic and strongly basic ion exchanger, subsequently filtered and washed with methylene chloride to give two phases. The organic phase is dried and concentrated. 11.5 g of N-[4-[4-(4-bromo-benzoyl)-phenoxy]-but-2-enyl]-N-cyclopropyl-2,2,2-trifluoroacetamide are obtained as a yellowish solid, MS: m/e 412 (M$^+$-CF$_3$, 1Br).

b) A solution of 11.5 g of N-[4-[4-(4-bromo-benzoyl)-phenoxy]-but-2-enyl]-N-cyclopropyl-2,2,2-trifluoroacetamide in 150 ml of methanol and 50 ml of tetrahydrofuran is treated with 5 ml of 20% aqueous potassium hydroxide solution while cooling with ice. The mixture is brought to room temperature and stirred for one hour, concentrated under reduced pressure and the residue is treated with 100 ml of water. The phases are separated and the inorganic phase is extracted with methylene chloride. The organic extracts are washed with saturated sodium chloride solution, dried and evaporated. After purification of the residue over silica gel with ethyl acetate-hexane-triethylamine (50/49/1) there are obtained 7.0 g of (4-bromo-phenyl)-[4-(4-cyclopropylamino-but-2-enyloxy)-phenyl]-methanone, MS: m/e 386 (M+H$^+$, 1Br), c) The product from b) is taken up in 100 ml of a 1N NaH$_2$PO$_4$ solution and treated with 100 ml of dioxan. After the addition of 10 ml of a 37% aqueous formaldehyde solution the mixture is heated to 65° C. for 3 hours. For the working up the mixture is adjusted to pH>11 with 10% aqueous sodium hydroxide solution and extracted with ether. After evaporation of the ethereal extracts and chromatography of the residue on silica gel with ethyl acetate-hexane-triethylamine (from 19/80/1 to 29/70/1) there are obtained 5.0 g of (E)-(4-bromo-phenyl)-[4-[4-(cyclopropyl-methyl-amino)-but-2-enyloxy]-phenyl]-methanone which is converted into the hydrochloride, MS: m/e 400 (M+H$^+$, 1Br).

EXAMPLE 13

Analogously to Example 12:

a) from [4-(6-bromo-hexyloxy)-phenyl]-(4-bromo-phenyl)-methanone there is obtained [6-[6-(cyclopropyl-methyl-amino)-hexyloxy]-phenyl]-(4-bromo-phenyl)-methanone which is converted into the hydrochloride, MS: m/e 430, (M+H$^+$, 1Br), b) from (E)4-[4-(4-bromo-but-2-enyloxy)-3-fluoro-benzoyl]-benzonitrile there is obtained (E)-4-[4-[4-(cyclopropyl-methyl-amino)-but-2-enyloxy]-3-fluoro-benzoyl]-benzonitrile which is converted with fumaric acid into the fumarate or with 4M hydrochloric acid in ether into the hydrochloride, MS: m/e 365 (M+H$^+$, 1Br).

EXAMPLE 14

From (4-bromo-phenyl)-[4-[6-[(3-hydroxy-propyl)-amino]-hexyloxy]-phenyl]-methanone (Ex. Ff) and subsequent N-methylation (analogously to Bsp 12c) there is obtained (4-bromo-phenyl)-[4-[6-[(3-hydroxy-propyl)-methyl-amino]-hexyloxy]-phenyl]-methanone which is converted into the fumarate, MS: m/e 448 (M+H$^+$, 1Br).

EXAMPLE 15 a) 10 g of [4-(6-bromo-hexyloxy)-phenyl]-(4-bromo-phenyl)-methanone are dissolved in 200 ml of DMF and, after the addition of 14.7 g of sodium azide, the mixture is stirred at 90° C. for 24 hours, filtered and the filtrates are concentrated under reduced pressure. The residue is taken up in 200 ml of ethyl acetate and washed with 10% aqueous sodium hydrogen carbonate solution. The organic phase is dried and concentrated. There are obtained 9.2 9 of [4-(6-azido-hexyloxy)-phenyl]-(4-bromo-phenyl)-methanone, MS: m/e 401 (M+H⁺, 1Br).

b) 7.1 g of triphenylphosphine are added to a solution of 8.7 g of [4-(6-azido-hexyloxy)-phenyl]-(4-bromo-phenyl)-methanone in 100 ml of tetrahydrofuran-water (4:1) and the mixture is stirred at room temperature for 5 hours and subsequently evaporated. The residue is taken up in methylene chloride and treated with ethereal hydrochloric acid solution. The separated hydrochloride is filtered off and washed with ether. There are obtained 8.0 g of [4-(6-amino-hexyloxy)-phenyl]-(4-bromo-phenyl)-methanone•hydrochloride, MS: m/e 376, (M+H⁺, 1Br).

c) 1.1 g of [4-(6-amino-hexyloxy)-phenyl]-(4-bromo-phenyl)-methanone are suspended in 30 ml of ether and 1.25 ml of trifluoroacetic anhydride are slowly added dropwise at 4° C. Then, the ice bath is removed and the reaction mixture is stirred at room temperature for 24 hours, then poured into 100 ml of water and neutralized with saturated sodium hydrogen carbonate solution. The aqueous phase is separated and extracted with ethyl acetate. The organic phases are washed with saturated sodium chloride solution, dried and evaporated. The residue is taken up in methylene chloride and filtered off. The filtrate is concentrated, dissolved in methylene chloride and treated with hexane. After filtration of the separated crystals there is obtained 0.8 g of N-[6-[4-(4-bromo-benzoyl)-phenoxy)]-hexyl]-2,2,2-trifluoroacetamide, MS: m/e 471 (M+H⁺, 1Br).

d) 0.65 g of N-[6-[4-(4-bromo-benzoyl)-phenoxy)]-hexyl]-2,2,2-trifluoroacetamide is added at −20° C. to a suspension of 0.08 g of 55% sodium hydride in 20 ml of DMF. The mixture is stirred for 30 minutes and the temperature is brought to room temperature. Subsequently, 0.24 g of methyl iodide is added and the mixture is stirred at room temperature for 1 hour. The reaction mixture is treated with saturated ammonium chloride solution, adjusted to pH~4 with 1N hydrochloric acid solution and extracted with methylene chloride. The organic extracts are dried and concentrated. After chromatography of the residue on silica gel with ethyl acetate-hexane (2:8) there is obtained 0.45 g of N-[6-[4-(4-bromo-benzoyl)-phenoxy)]-hexyl]-N-methyl-2,2,2-trifluoroacetamide, MS: m/e 485 (M+H⁺, 1Br).

e) Analogously to Example 12b), from N-[6-[4-(4-bromo-benzoyl)-phenoxy)]-hexyl]-N-methyl-2,2,2-trifluoroacetamide there is obtained (4-bromo-phenyl)-[4-(6-methylamino-hexyloxy)-phenyl]-methanone, MS: m/e 389 (M+H⁺, 1Br).

f) A mixture of 0.1 g of (4-bromo-phenyl)-[4-(6-methylamino-hexyloxy)-phenyl]-methanone, 0.13 ml of diisopropylethylamine and 0.06 ml of bromomethyl-cyclopropane in 20 ml of dimethylacetamide is stirred at 50° C. for 24 hrs., concentrated and the residue is treated with sodium hydrogen carbonate solution and extracted with methylene chloride. The organic phases are washed with saturated sodium chloride solution, dried and evaporated. The residue is purified over silica gel with $CH_2Cl_2$/MeOH/ $NH_4OH$ (9415.410.6 to 85/12.5/2.5). There is obtained 0.68 g of (4-bromo-phenyl)-[4-[6-(cyclopropylmethyl-methyl-amino)-hexyloxy]-phenyl]-methanone which is converted into the fumarate, MS: m/e 443 (M+H⁺, 1Br).

EXAMPLE 16

Starting Material

Analogously to Example 12a, from (E)-[4-(4-bromo-but-2-enyloxy)-phenyl]-(4-bromo-phenyl)-methanone and 2,2,2-trifluoroacetamide there is obtained N-[4-[4-(4-bromo-benzoyl)-phenoxy]-but-2-enyl]-2,2,2-trifluoroacetamide, MS: m/e 441 (M, 1Br).

Product

Analogously to Example 15:

a) from N-[4-[4-(4-bromo-benzoyl)-phenoxy]-but-2-enyl]-2,2,2-trifluoroacetamide via N-[4-[4-(4-bromo-benzoyl)-phenoxy]-but-2-enyl]-N-methyl-2,2,2-trifluoroacetamide and (4-bromo-phenyl)-[4-(4-methylamino-but-2-enyloxy)-phenyl]-methanone there is obtained (E)-(4-bromo-phenyl)-[4-[4-(cyclopropylmethyl-methyl-amino)-but-2-enyloxy]-phenyl]-methanone which is converted into the fumarate, MS: m/e 413 (M+H⁺, 1Br), b) from (4-bromo-phenyl)-[4-(6-methylamino-hexyloxy)-phenyl]-methanone and 1-bromoacetone in dimethylacetamide at room temperature there is obtained 1-[[6-[4-(4-bromo-benzoyl)-phenoxy]-hexyl]-methyl-amino]-propan-2-one which is converted into the fumarate, MS: m/e 446 (M+H⁺, 1Br).

EXAMPLE 17

A suspension of 0.4 g of (E)-[[4-[4-(4-bromo-benzoyl)-phenoxy]-but-2-enyl]-methyl-amino]-acetonitrile (Ex. 2j) and 0.04 g of potassium carbonate in 3 ml of dimethyl sulphoxide is cooled to 0° C. and treated with 1 ml of 30% hydrogen peroxide solution. The reaction mixture is warmed to room temperature and stirred overnight. For the working up, the mixture is treated with 10 ml of water and the separated crystals are filtered off and washed with water. There is obtained 0.38 g of (E)-2-[[4-[4-(4-bromo-benzoyl)-phenoxy]-but-2-enyl]-methyl-amino]-acetamide, MS: m/e 372 (M⁺-$H_2NCO$, 1Br).

EXAMPLE 18

Analogously to Example 17:

from (E)-4-[4-[4-(cyclopropyl-methyl-amino)-but-2-enyloxy]-3-fluoro-benzoyl]-benzonitrile (Ex. 13b) there is obtained (E)-4-[4-[4-(cyclopropyl-methyl-amino)-but-2-enyloxy]-3-fluoro-benzoyl]-benzamide which is converted into the fumarate, MS: m/e 383 (M+H⁺, 1Br).

EXAMPLE 19

A solution of 0.92 ml of hexamethyldisilazane in 2.5 ml of THF is treated dropwise at 0° C. with 2.63 ml of 1.6M butyl-lithium in hexane. After 15 min. the mixture is cooled to −78° C. and 0.6 g (Ex. Fa) of (E)-1-[4-[4-(allyl-methyl-amino)-but-2-enyloxy]-3-fluoro-phenyl]-ethanone (Ha) in 1.9 ml of THF is added dropwise. After 1 hr. at −78° C. 0.5 ml of geranyl bromide in 1 ml of THF is added dropwise. The mixture is left to warm to room temperature, stirred for 1 hr. and poured into saturated sodium bicarbonate solution/ether. The organic phase is washed with 10% sodium chloride solution, dried and evaporated. After silica gel chromatography with (97.5%) methylene chloride/methanol the residue is dissolved in ethanol with 0.87 g of fumaric acid, evaporated and precipitated from ether with pentane. There is obtained 0.24 g of (E)-1-[4-[(E)-4-(allyl-methyl-amino)-but-2-enyloxy]-3-fluoro-phenyl]-2-[(E)-3,7-dimethyl-octa-2,6-dienyl]-5,9-dimethyl-deca-4,8-dien-1-one•fumarate (1:2), MS: m/e 549 (M).

EXAMPLE 20

Analogously to Example 19:

from (E)-1-[4-[4-(allyl-methyl-amino)-but-2-enyloxy]-3-fluoro-phenyl]-ethanone (Ex. Fa) and 3,3-dimethylallyl bromide there is obtained (E)-1-[4-[4-(allyl-methyl-amino)-but-2-enyloxy]-3-fluoro-phenyl]-5-methyl-2-

(3-methyl-but-2-enyl)-hex-4-en-1-one•fumarate (1:1), MS: m/e 413 (M).

EXAMPLE 21

A solution of 0.86 ml of diisopropylamine in 5 ml of THF is treated dropwise at 0° C. with 3.5 ml of 1.6M butyllithium in hexane. After 15 min. the mixture is cooled to −78° C. and 1.1 g of (E)-1-[4-[4-(allyl-methyl-amino)-but-2-enyloxy]-3-fluoro-phenyl]-ethanone (Ex. Fa) in 3.9 ml of THF is added dropwise. After 1 hr. at −78° C. 0.7 ml of 3-methyl-2-butenal in 0.8 ml of THF is added dropwise. After 20 min. at −78° C. 0.86 ml of acetic acid in 4.6 ml of ether is added dropwise and the mixture is poured into saturated sodium bicarbonate solution/methylene chloride. The organic phase is dried and evaporated. After silica gel chromatography with (97.5%) methylene chloride/methanol the residue is dissolved in ethanol with 0.24 g of fumaric acid, evaporated and precipitated from methylene chloride with ethyl acetate/ether. There is obtained 0.64 g of (E)-(RS)-1-[4-[4-(allyl-methyl-amino)-but-2-enyloxy]-3-fluoro-phenyl]-3-hydroxy-5-methyl-hex-4-en-1-one•fumarate (1:1), MS: m/e 362 (M+H$^+$).

EXAMPLE 22

Analogously to Example 21:
a) from (E)-1-[4-[4-(allyl-methyl-amino)-but-2-enyloxy]-2-fluoro-phenyl]-ethanone (Ex. Fb) and 3-methyl-2-butenal there is obtained (E)-(RS)-1-[4-[4-(allyl-methyl-amino)-but-2-enyloxy]-2-fluoro-phenyl]-3-hydroxy-5-methyl-hex-4-en-1-one, MS: m/e 362 (M+H$^+$),
b) from (E)-1-[4-[4-(allyl-methyl-amino)-but-2-enyloxy]-phenyl]-ethanone (Ex. Fc) and 3-methyl-2-butenal there is obtained (E)-(RS)-1-[4-[4-(allyl-methyl-amino)-but-2-enyloxy]-phenyl]-3-hydroxy-5-methyl-hex-4-en-1-one•fumarate (1:1), MS: m/e 344 (M+H$^+$),
c) from (E)-1-[4-[4-(allyl-methyl-amino)-but-2-enyloxy]-3-fluoro-phenyl]-ethanone (Ex. Fa) and (E)-citral there is obtained (E)-(RS)-1-[4-[(E)4-(allyl-methyl-amino)-but-2-enyloxy]-3-fluoro-phenyl]-3-hydroxy-5,9-dimethyl-deca-4,8-dien-1-one•fumarate (1:1), MS: m/e 430 (M+H$^+$).

EXAMPLE 23

From (E)-1-[4-[4-(allyl-methyl-amino)-but-2-enyloxy]-3-fluoro-phenyl]-ethanone (Ex. Fa) and 11-bromo-1-undecanal analogously to Example 21 there is obtained (E)-(RS)-1-[4-[4-(allyl-methyl-amino)-but-2-enyloxy]-3-fluoro-phenyl]-13-bromo-3-hydroxy-tridecan-1-one. 0.53 g of the resulting bromide is dissolved in 3.4 ml of DMA, treated at 0° C. with 0.19 ml of N-allyl-methyl-amine and, after 20 hrs. at room temperature, evaporated. The residue is taken up in methylene chloride/saturated sodium bicarbonate solution, the organic phase is dried and filtered. After evaporation the residue is purified over silica gel with methylene chloride/methanol (95:5 to 6:1). The 0.39 g of (E)-(RS)-13-(allyl-methyl-amino)-1-[4-[4-(allyl-methyl-amino)-but-2-enyloxy]-3-fluoro-phenyl]-3-hydroxy-tridecan-1-one is converted with fumaric acid into (E)-(RS)-13-(allyl-methyl-amino)-1-[4-[4-(allyl-methyl-amino)-but-2-enyloxy]-3-fluoro-phenyl]-3-hydroxy-tridecan-1-ones fumarate (1:2), MS: m/e 517 (M+H$^+$).

EXAMPLE 24

From 1-[6-[6-(allyl-methyl-amino)-hexyloxy]-pyridin-3-yl]-ethanone and 3-methyl-2-butenal analogously to Example 21 there is obtained directly the dehydrated (E)-1-[6-[6-(allyl-methyl-amino)-hexyloxy]-pyridin-3-yl]-5-methyl-hexa-2,4-dien-1-one•fumarate (1:1), MS: m/e 356 (M$^+$).

EXAMPLE 25

A solution of 4.1 g of (E)-(RS)-1-[4-[4-(allyl-methyl-amino)-but-2-enyloxy]-3-fluoro-phenyl]-3-hydroxy-5-methyl-hex-4-en-1-one (Ex. 21) in 280 ml of toluene is added to 2.6 g of p-toluenesulphonic acid and stirred at room temperature for 2.5 hrs. The reaction mixture is concentrated, the residue is dissolved in methylene chloride, extracted with saturated sodium bicarbonate solution, dried and the residue is concentrated and purified over silica gel with 97.5% methylene chloride/methanol. The free amine is dissolved in methylene chloride/methanol with 0.75 g of fumaric acid, evaporated and recrystallized from ethyl acetate/methanol/ether. There are obtained 2.77 g of (E)-1-[4-[(E)-4-(allyl-methyl-amino)-but-2-enyloxy]-3-fluoro-phenyl]-5-methyl-hexa-2,4-dien-1-one•fumarate (1:1), MS: m/e 344 (M+H$^+$).

EXAMPLE 26

Analogously to Example 25:
a) from (E)-(RS)-13-(allyl-methyl-amino)-1-[4-[4-(allyl-methyl-amino)-but-2-enyloxy]-3-fluoro-phenyl]-3-hydroxy-tridecan-1-one (Ex. 23) there is obtained (E)-13-(allyl-methyl-amino)-1-[4-[(E)-4-(allyl-methyl-amino)-but-2-enyloxy]-3-fluoro-phenyl]-tridec-2-en-1-one•fumarate (1:2), MS: m/e 499 (M+H$^+$),
b) from (E)-(RS)-1-[4-[4-(allyl-methyl-amino)-but-2-enyloxy]-2-fluoro-phenyl]-3-hydroxy-5-methyl-hex-4-en-1-one (Ex. 22a) there is obtained (E)-1-[4-[(E)-4-(allyl-methyl-amino)-but-2-enyloxy]-2-fluoro-phenyl]-5-methyl-hexa-2,4-dien-1-one•fumarate (1:1), MS: m/e 344 (M+H$^+$),
c) from (E)-(RS)-1-[4-[4-(allyl-methyl-amino)-but-2-enyloxy]-phenyl]-3-hydroxy-5-methyl-hex-4-en-1-one (Ex. 22b), there is obtained (E)-1-[4-[(E)-4-(allyl-methyl-amino)-but-2-enyloxy]-phenyl]-5-methyl-hexa-2,4-dien-1-one•fumarate (1:1), m.p. 120–123° C.,
d) from (E)-(RS)-1-[4-[(E)-4-(allyl-methyl-amino)-but-2-enyloxy]-3-fluoro-phenyl]-3-hydroxy-5,9-dimethyl-deca-4,8-dien-1-one (Ex. 22c) there is obtained (2E,4E)-1-[4-[(E)4-(allyl-methyl-amino)-but-2-enyloxy]-3-fluoro-phenyl]-5,9-dimethyl-deca-2,4,8-trien-1-one•fumarate (1:1), MS: m/e 412 (M+H$^+$).

EXAMPLE 27

27.1. Starting Material

A solution of 2.4 g of 4-bromo-2-fluoroacetanilide in 30 ml of absolute THF is cooled to −78° C. and treated within 20 min. with 13.8 ml of 1.6M butyllithium in hexane. After 15 min. 2.6 g of 4-bromo-N-methoxy-N-methylbenzamide (prepared from 4-bromo-benzoyl chloride and N,O-dimethylhydoxylamine hydrochloride with N-methylmorpholine) in 5 ml of THF are added dropwise. After stirring at −78° C. for 20 hrs. the reaction solution is poured into cold 10% potassium hydrogen sulphate solution/ether and the organic phase is washed with 10% sodium chloride solution and dried. After crystallization from methylene chloride/ether there are obtained 1.2 g of N-[4-(4-bromo-benzoyl)-(2-fluoro-phenyl)-acetamide, MS: m/e 335 (M, 1Br).

27.2. Product 5.0 g of N-[4-(4-bromo-benzoyl)-(2-fluoro-phenyl)-acetamide (Ex. 27.1) are dissolved in THF with 9.6 g of (E)-1,4-dibromobutene and treated at −22° C. with 1.3 g of 55% sodium hydride. After 30 min. the mixture is left to warm to RT overnight. The reaction is completed by the addition of ethyl acetate and water and the reaction mixture is worked up with 10% potassium hydrogen sulphate solution/ethyl acetate. The organic phase is washed with 10% sodium chloride solution, dried and concentrated. After chromatography over silica gel with methylene chloride/ ethyl acetate (99:1 to 98:2) there are obtained 4.8 g of (E)-N-(4-bromo-but-2-enyl)-N-[4-(4-bromo-benzoyl)-2-fluoro-phenyl]-acetamide which is dissolved in 35 ml of N,N-dimethylacetamide and treated at room temperature with 2.0 ml of N-allyl-methyl-amine. After 3 hrs. the mixture is evaporated, the residue is taken up in methylene chloride and washed with sat. sodium bicarbonate solution/ 10% sodium chloride solution, dried and concentrated. After purification over silica gel with methylene chloride/ methanol (0.2% to 5%) the product in methylene chloride/ ether is treated with 4.8M hydrochloric acid solution in ether and precipitated with ethyl acetate/ether. There are obtained 3.5 g of (E)-N-[4-(allyl-methyl-amino)-but-2-enyl]-N-[4-(4-bromo-benzoyl)-2-fluoro-phenyl]-acetamide•hydrochloride (1:1), MS: m/e 458 (M, 1Br).

EXAMPLE 28

Analogously to Example 27:
from N-[4-(4-bromo-benzoyl)-(2-fluoro-phenyl)-acetamide (Ex. 27.1) with 1,6-dibromohexane there is obtained N-[6-(allyl-methyl-amino)-hexyl]-N-[4-(4-bromo-benzoyl)-2-fluoro-phenyl]-acetamide•hydrobromide (1:1), MS: m/e 488 (M, 1Br).

EXAMPLE 29

2.0 g of (E)-N-[4-(allyl-methyl-amino)-but-2-enyl]-N-[4-(4-bromo-benzoyl)-2-fluoro-phenyl]-acetamide (Ex. 27) are added to a solution of 0.4 g of KOH in ethanol and boiled under reflux for 5 hrs. After evaporation the residue is taken up in a 10% sodium chloride solution in ethyl acetate and the organic phase is dried and concentrated. After purification over silica gel with methylene chloride/methanol (0.5% to 2%) the product is dissolved in methylene chloride and treated at 0° C. with one equivalent of hydrochloric acid in ether. Precipitation with ethyl acetate/ether gives 1.2 g of (E)-[4-[4-(allyl-methyl-amino)-but-2-enylamino]-2-fluoro-phenyl]-(4-bromo-phenyl)-methanone•hydrochloride (1:1), MS: m/e 416 (M, 1Br).

EXAMPLE 30

Analogously to Example 29:
from N-[6-(allyl-methyl-amino)-hexyl]-N-[4-(4-bromo-benzoyl)-2-fluoro-phenyl]-acetamide (Ex. 28) there is obtained [4-[6-(allyl-methyl-amino)-hexylamino]-3-fluoro-phenyl]-(4-bromo-phenyl)-methanone•hydrochloride (1:1), MS: m/e 446 (M, 1Br).

EXAMPLE 31

31.1. Starting Materials
A.a) 13.4 ml of 2M potassium hydroxide in methanol are added dropwise to a solution of 5.0 g of diethyl (1RS,2RS)-1,2-cyclopropanedicarboxylate in 9 ml of methanol. After 2.5 hrs. the mixture is acidified with 8% phosphoric acid and extracted with saturated sodium chloride solution/methylene chloride, dried and concentrated, with 5.1 g of (1RS,2RS)-1,2-cyclopropanedicarboxylic acid monomethyl ester being obtained.
A.b) A solution of 9.3 g of (1RS,2RS)-1,2-cyclopropanedicarboxylic acid monomethyl ester, 4.0 ml of N-cyclopropanamine and 11.6 g of N-(3-dimethylaminopropyl)-N'-ethylcarbodiimide hydrochloride in 210 ml of methylene chloride is treated at 0° C. with 0.7 g of dimethylaminopyridine and subsequently stirred at room temperature for 2 hrs. The reaction solution is worked up with methylene chloride/10% potassium hydrogen sulphate solution. The organic phase is washed with saturated sodium bicarbonate solution, dried and concentrated, with 10.6 g of methyl (1RS,2RS)-2-cyclopropylcarbamoyl-cyclopropanecarboxylate being obtained.
A.c) A solution of 4.9 g of methyl (1RS,2RS)-2-cyclopropylcarbamoyl-cyclopropanecarboxylate and 10.8 ml of methyl iodide in 120 ml of 1,2-dimethoxyethane is treated at 0° C. with 1.2 g of 55% sodium hydride and stirred at 0° C. for 22 hrs. After the addition of water the mixture is evaporated and extracted with 10% potassium hydrogen sulphate solution/ether, washed with saturated sodium chloride solution and the organic phase is dried.
A.d) The crude methyl (1RS,2RS)-2-(cyclopropyl-methyl-carbamoyl)-cyclopropanecarboxylate is dissolved in 9 ml of THF and added dropwise to a boiling suspension of 1.4 g of lithium aluminium hydride in 40 ml of THF. The reaction mixture is boiled for a further 24 hrs., cooled to 0° C. and treated with 9 ml of water, dried, filtered and concentrated. The oil is dissolved in methylene chloride, dried and concentrated, with 4.2 g of (1RS,2RS)-[2-[(cyclopropyl-methyl-amino)-methyl]-cyclopropyl]-methanol being obtained, MS: m/e 156 (M+H⁺).
B) Analogously to Example 3 1.1.A):
B.a) from diethyl (1RS,2RS)-1,2-cyclopropanedicarboxylate via (1RS,2RS)-1,2-cyclopropanedicarboxylic acid monomethyl ester and methyl (1RS,2RS)-2-allyl-methylcarbamoyl-cyclopropanecarboxylate there is obtained (1RS,2RS)-[2-[(allyl-methyl-amino)-methyl]-cyclopropyl]-methanol, MS: m/e 156 (M+H⁺),
B.b) from diethyl (1RS,2RS)-1,2-cyclopropanedicarboxylate via (1RS,2RS)-1,2-cyclopropanedicarboxylic acid monomethyl ester and methyl (1RS,2RS)-2-ethyl-methylcarbamoyl-cyclopropanecarboxylate there is obtained (1RS,2RS)-[2-[(ethyl-methyl-amino)-methyl]-cyclopropyl]-methanol,
B.c) from diethyl (1RS,2RS)-1,2-cyclopropanedicarboxylate via (1RS,2RS)-1,2-cyclopropanedicarboxylate monomethyl ester, methyl (1RS,2RS)-2-cyclopropylmethylcarbamoyl-cyclopropanecarboxylate and methyl (1RS,2RS)-2-(cyclopropylmethyl-methyl-carbamoyl)-cyclopropanecarboxylate there is obtained (1RS,2RS)-[2-[(cyclopropylmethyl-methyl-amino)-methyl]-cyclopropyl]-methanol,
B.d) from diethyl (1RS,2RS)-1,2-cyclopropanedicarboxylate via (1RS,2RS)-1,2-cyclopropanedicarboxylate monomethyl ester, methyl (1RS,2 RS)-2-cyclopropylcarbamoyl-cyclopropanecarboxylate and methyl (1RS,2RS)-2-(allyl-cyclopropyl-carbamoyl)-cyclopropanecarboxylate there is obtained (1RS,2RS)-[2-[(allyl-cyclopropyl-amino)-methyl]-cyclopropyl]-methanol.

31.2 Product
A solution of 6.2 g of triphenylphosphine, 6.5 g of (4-bromo-phenyl)-(4-hydroxy-phenyl)-methanone and 3.64 g of (1RS,2RS)-[2-[(cyclopropyl-methyl-amino)-methyl]-cyclopropyl]-methanol (Ex. 31.1.A.d) in 190 ml of THF is treated at room temperature during 1 hr. with 4.03 ml of diethyl azodicarboxylate in 18 ml of THF. After stirring for 3 hrs. the mixture is concentrated, taken up in ether and washed with saturated sodium bicarbonate solution and 10% sodium chloride solution, dried and concentrated. The residue is dissolved in ether and precipitated with hexane. The mother liquor is concentrated and the crude (1RS,2RS)-(4-bromo-phenyl)-[4-[2-[(cyclopropyl-methyl-amino)-methyl]-cyclopropylmethoxy]-phenyl]-methanone is dissolved in ethanol, treated with 2.7 g of fumaric acid and crystallized out. There are obtained 4.1 g of (1RS,2RS)-(4-bromo-phenyl)-[4-[2-[(cyclopropyl-methyl-amino)-methyl]-cyclopropylmethoxy]-phenyl]-methanone•fumarate (1:1), m.p. 136–137° C.

Crystallization of (1RS,2RS)-(4-bromo-phenyl)-[4-[2-[(cyclopropyl-methyl-amino)-methyl]-cyclopropylmethoxy]-phenyl]-methanone from methylene chloride with 4M hydrochloric acid in ether gives (1RS,2RS)-(4-bromo-phenyl)-[4-[2-[(cyclopropyl-methyl-amino)-methyl]-cyclopropylmethoxy]-phenyl]-methanone•hydrochloride (1:1), m.p. 93–95° C.

EXAMPLE 32

Analogously to Example 31.2:
a) from (1RS,2RS)-[2-[(cylcopropyl-methyl-amino)-methyl]-cyclopropyl]-methanol (Ex. 31.1.A.d) and (4-bromo-phenyl)-(3-fluoro-4-hydroxy-phenyl)-methanone there is obtained (1RS,2RS)-(4-bromo-phenyl)-[4-[2-[(cyclopropyl-methyl-amino)-methyl]-cyclopropylmethoxy]-3-fluoro-phenyl]-methanone•fumarate (1:1), m.p. 152–154° C.,
b) from (1RS,2RS)-[2-[(cylcopropyl-methyl-amino)-methyl]-cyclopropyl]-methanol (Ex. 31.1.A.d) and (3-fluoro-4-hydroxy-benzoyl)-benzonitrile there is obtained (1RS,2RS)-4-[4-[2-[(cyclopropyl-methyl-amino)-methyl]-cyclopropylmethoxy]-3-fluoro-benzoyl]-benzonitrile•fumarate (1:1), m.p. 116–117° C.,
c) from (1RS,2RS)-[2-[(cyclopropylmethyl-methyl-amino)-methyl]-cyclopropyl]-methanol (Ex. 31.1.Bc) and (4-bromo-phenyl)-(4-hydroxy-phenyl)-methanone there is obtained (1RS,2RS)-(4-bromo-phenyl)-[4-[2-[(cyclopropylmethyl-methyl-amino)-methyl]-cyclopropylmethoxy]-phenyl]-methanone•fumarate (1:1), m.p. 128–131° C.,
d) from (1RS,2RS)-[2-[(cylcopropyl-methyl-amino)-methyl]-cyclopropyl]-methanol (Ex. 31.1.A.d) and (4-bromo-phenyl)-(2-fluoro-4-hydroxy-phenyl)-methanone there is obtained (1RS,2RS)-(4-bromo-phenyl)-[4-[2-[(cyclopropyl-methyl-amino)-methyl]-cyclopropylmethoxy]-2-fluoro-phenyl]-methanone•fumarate (1:1), m.p. 133–135° C.,
e) from (1RS,2RS)-[2-[(allyl-cyclopropyl-amino)-methyl]-cyclopropyl]-methanol (Ex. 31.1.Bd) and (4-bromo-phenyl)-(4-hydroxy-phenyl)-methanone there is obtained (1RS,2RS)-[4-[2-[(allyl-cyclopropyl-amino)-methyl]-cyclopropylmethoxy]-phenyl]-(4-bromo-phenyl)-methanone•hydrochloride (1:1), m.p. 120–122° C.,
f) from (1RS,2RS)-[2-[(cylcopropyl-methyl-amino)-methyl]-cyclopropyl]-methanol (Ex. 31.1.A) and 1-(4-hydroxy-phenyl)-5-methyl-hexan-1-one there is obtained (1RS,2RS)-1-[4-[2-[(cyclopropyl-methyl-amino)-methyl]-cyclopropylmethoxy]-phenyl]-5-methyl-hexan-1-one•hydrochloride (1:1), m.p. 110–112° C.,
g) from (1RS,2RS)-[2-[(ethyl-methyl-amino)-methyl]-cyclopropyl]-methanol (Ex. 31.1.Bb) and (4-bromo-phenyl)-(4-hydroxy-phenyl)-methanone there is obtained (1RS,2RS)-(4-bromo-phenyl)-[4-[2-[(ethyl-methyl-amino)-methyl]-cyclopropylmethoxy]-phenyl]-methanone•fumarate (1:1), m.p. 136–138° C.,
h) from (1RS,2RS)-[2-[(allyl-methyl-amino)-methyl]-cyclopropyl]-methanol (Ex. 31.1.Ba) and (4-bromo-phenyl)-(4-hydroxy-phenyl)-methanone there is obtained (1RS,2RS)-[4-[2-[(allyl-methyl-amino)-methyl]-cyclopropylmethoxy]-phenyl]-(4-bromo-phenyl)-methanone which is converted into the hydrochloride, m.p. 112° C. (with decomposition).

EXAMPLE 33

A solution of 2.6 g of [4-[6-(allyl-methyl-amino)-hexyloxy]-2-fluoro-phenyl]-(4-bromo-phenyl)-methanone in 115 ml of dimethylacetamide is boiled at 120° C. for 3 hrs. with 7.2 ml of 8.03M methylamine in ethanol, concentrated and the residue is chromatographed over silica gel with methylene chloride/methanol (2.5%–10%). The resulting oil is dissolved in methylene chloride and stirred with 0.5 g of fumaric acid overnight, with 1.5 g of [4-[6-(allyl-methyl-amino)-hexyloxy]-2-methylamino-phenyl]-(4-bromo-phenyl)-methanone•fumarate, m.p. 72° C., being obtained.

EXAMPLE 34

Analogously to Example 33:
a) from [4-[6-(allyl-methyl-amino)-hexyloxy]-2-fluoro-phenyl]-(4-bromo-phenyl)-methanone with dimethylamine there is obtained [4-[6-(allyl-methyl-amino)-hexyloxy]-2-dimethylamino-phenyl]-(4-bromo-phenyl)-methanone•hydrochloride (1:2), MS: m/e 473 (M+H$^+$, 1Br),
b) from [4-[6-(allyl-methyl-amino)-hexyloxy]-2-fluoro-phenyl]-(4-bromo-phenyl)-methanone with 1,2,4-triazole there is obtained [4-[6-(allyl-methyl-amino)-hexyloxy]-2-1H-[1,2,4]triazol-1-yl-phenyl]-(4-bromo-phenyl)-methanone•hydrochloride (1:1), MS: m/e 496 (M, 1Br),
c) from 1-[4-[6-(allyl-methyl-amino)-hexyloxy]-2-fluoro-phenyl]-5-methyl-hex-5-en-1-one (Ex. F.e) with methylamine in ethanol there is obtained 1-[4-[6-(allyl-methyl-amino)-hexyloxy]-2-methylamino-pheny]-4-methyl-hex-5-en-1-one, MS: m/e 487 (M+H$^+$),
d) from (E)-1-[4-[4-(allyl-methyl-amino)-but-2-enyloxy]-2-fluoro-phenyl]-5-methyl-hex-4-en-1-one (Ex. Fd) with sodium thiomethanolate in THF there is obtained (E)-1-[4-[4-(allyl-methyl-amino)-but-2-enyloxy]-2-methylsulphanyl-phenyl]-5-methyl-hex-4-en-1-one-fumarate (1:1), MS: m/e 374 (M$^+$).

EXAMPLE 35

Analogously to Example 33, 8.97 g of [4-[6-(allyl-methyl-amino)-hexyloxy]-2-fluoro-phenyl]-(4-bromo-phenyl)-methanone in 450 ml of THF are stirred with 37 ml of 5.4M sodium methanolate in methanol at room temperature for 14 hrs. and under reflux for 1 hr. The solution is evaporated and the residue is taken up in methylene chloride/10% sodium chloride solution. The organic phase is dried, dissolved in ether and stirred overnight with 2.08 g of fumaric acid. 8.17 g of [4-[6-(allyl-methyl-amino)-hexyloxy]-2-methoxy-phenyl]-(4-bromo-phenyl)-methanone•fumarate (m.p. 108–113° C.) are obtained.

The fumarate obtained is taken up in methylene chloride/saturated sodium bicarbonate solution and the organic phase is dried and concentrated. 3.09 g of the thus-obtained [4-[6-(allyl-methyl-amino)-hexyloxy]-2-methoxy-phenyl]-(4-bromo-phenyl)-methanone are boiled in 13 ml of acetic acid/7.7 ml of 62% HBr solution at 90° C. for 2 hrs. The reaction mixture is concentrated and the residue is converted into the free base with methylene chloride/saturated sodium bicarbonate solution. The residue is treated with 0.74 g of fumaric acid and processed using ethanol/ether. There are obtained 2.05 g of [4-[6-(allyl-methyl-amino)-hexyloxy]-2- hydroxy-phenyl]-(4-bromo-phenyl)-methanone fumarate, MS: m/e 446 (M+H⁺, 1Br).

EXAMPLE 36

Analogously to Example 33, 17.55 g of [4-[6-(allyl-methyl-amino)-hexyloxy]-2-fluoro-phenyl]-(4-bromo-phenyl)-methanone are boiled under reflux for 23 hrs. with 50.7 ml of 4-methoxybenzylamine and 6.5 g of potassium carbonate in 600 ml of toluene. After filtration, evaporation and purification over silica gel with methylene chloride/methanol (2.5% to 10%) there are obtained 17.43 g of [4-[6-(allyl-methyl-amino)-hexyloxy]-2-(4-methoxy-benzylamino)-phenyl]-(4-bromo-phenyl)-methanone. A solution of this material in 200 ml of trifluoroacetic acid is stirred at room temperature for 45 hrs., evaporated and the residue is converted into the free base with methylene chloride/saturated sodium bicarbonate solution. After purification over silica gel with methylene chloride/methanol (9:1) there are obtained 13.23 g of [2-amino-4-[6-(allyl-methyl-amino)-hexyloxy]-phenyl]-(4-bromo-phenyl)-methanone. 9.1 g of the free base are dissolved in methylene chloride/ether and converted with 2.25 g of fumaric acid and by stirring overnight into 7.28 g of [2-amino-4-[6-(allyl-methyl-amino)-hexyloxy]-phenyl]-(4-bromo-phenyl)-methanone•fumarate (1:1), m.p. 78° C. (with decomposition).

EXAMPLE 37

A solution of 0.9 g of [2-amino-4-[6-(allyl-methyl-amino)-hexyloxy]-phenyl]-(4-bromo-phenyl)-methanone (Ex. 36) is treated in 20 ml of methylene chloride at 0° C. with 0.17 ml of methanesulphonyl chloride in 0.8 ml of methylene chloride and with 24.4 mg of dimethylaminopyridine. The reaction mixture is left to warm to room temperature overnight and concentrated and the residue is taken up in methylene chloride/saturated sodium bicarbonate solution. The organic phase is dried and concentrated. Purification over silica gel with methylene chloride/methanol (95:5) as the eluent gives 0.57 g of N-[5-[6-(allyl-methyl-amino)-hexyloxy]-2-(4-bromo-benzoyl)-phenyl]-methanesulphonamide which is converted into the fumarate, MS: m/e 523 (M+H⁺, 1Br).

EXAMPLE 38

2.8 g of Cer(III) chloride are dried, then taken up in 45 ml of THF and stirred at room temperature for 1 hr. Then, 7.2 ml of 1.6M methyllithium in ether are added at −78° C. and, after a further hr., 4.0 g of [4-[6-(allyl-methyl-amino)-hexyloxy]-2-fluoro-phenyl]-(4-bromo-phenyl)-methanone in 18 ml of THF are added dropwise. After 2.5 hrs. at −78° C. and 1 hr. at 0° C. the mixture is worked up with saturated ammonium chloride solution/methylene chloride. The organic phase is dried and concentrated. The residue is dissolved in ethanol with 0.9 g of fumaric acid, there being obtained after evaporation 5.1 g of (RS)-1-[4-[6-(allyl-methyl-amino)-hexyloxy]-2-fluoro-phenyl]-1-(4-bromo-phenyl)-ethanol•fumarate (1:1), MS: m/e 463 (M, 1Br).

EXAMPLE 39

Analogously to Example 38:
a) from (E)-[4-[4-(allyl-methyl-amino)-but-2-enyloxy]-phenyl]-5-methyl-hex-4-en-1-one there is obtained (E)-(RS)-2-[4-[4-(allyl-methyl-amino)-but-2-enyloxy]-phenyl]-6-methyl-hept-5-en-2-ol•fumarate (1:1), MS: m/e 344 (M+H⁺), b) from (E)-[4-[4-(allyl-methyl-amino)-but-2-enyloxy]-3-fluoro-phenyl]-(4-bromo-phenyl)-methanone and vinyl-magnesium chloride there is obtained (E)-(RS)-1-[4-[4-(allyl-methyl-amino)-but-2-enyloxy]-3-fluoro-phenyl]-(4-bromo-phenyl)-prop-2-en-1-ol•fumarate (1:1), MS: m/e 446 (M+H⁺, 1Br),
c) from [4-[(allyl-methyl-amino)-methyl]-biphenyl-4-yl]-(4-bromo-phenyl)-methanone and methylmagnesium chloride solution there is obtained (RS)-1-[4-[(allyl-methyl-amino)-methyl]-biphenyl-4-yl]-1-(4-bromo-phenyl)-ethanol which is converted into the fumarate, MS: m/e 436 (M+H⁺, 1Br).

EXAMPLE 40

1.0 g of [4-[6-(allyl-methyl-amino)-hexyloxy]-2-hydroxy-phenyl]-(4-bromo-phenyl)-methanone (Ex. 35) in 9 ml of THF/ether (1:1) is added dropwise during 45 min. to 4.8 ml of (1.7M in THF) vinylmagnesium chloride solution at 0° C. The solution is left to warm to room temperature overnight, treated with 3 ml of acetic acid/water (1:1) and worked up with saturated sodium bicarbonate solution/methylene chloride. After drying the organic phase is concentrated and the residue is purified over silica gel with methylene chloride/methanol (95:5). There is obtained 0.64 g of (RS)-5-[6-(allyl-methyl-amino)-hexyloxy]-2-[1-(4-bromo-phenyl)-1-hydroxy-allyl]-phenol, MS: m/e 474 (M+H⁺, 1Br).

EXAMPLE 41

Analogously to Example 40:
from [2-amino-4-[6-(allyl-methyl-amino)-hexyloxy]-phenyl]-(4-bromo-phenyl)-methanone (Ex. 36) there is obtained (RS)-1-[4-[6-(allyl-methyl-amino)-hexyloxy]-2-amino-phenyl]-1-(4-bromo-phenyl)-prop-2-en-1-ol, MS: m/e 473 (M+H⁺, 1Br).

EXAMPLE 42

42.1. Starting Materials
A) 3.58 g of (E)-4-bromo-2-buten-1-ol are dissolved in 100 ml of acetone and treated with 9.84 g of K₂CO₃ and 3.4 ml of N-allyl-methyl-amine. The suspension is stirred at RT for 40 h., filtered and the crude product obtained after concentration is purified on silica gel with methylene chloride:methanol (gradient 9:1–3:1). 1.52 g of (E)-4-(allyl-methyl-amino)-but-2-en-1-ol are obtained as a colourless liquid, MS: m/e 141 (M).
B) 1 ml of 1-bromo-6-hexanol are taken up in DMA, treated with 1.47 ml of N-allyl-methyl-amine and stirred at RT for 16 h. The reaction mixture is concentrated and the residue is lyophilized overnight. There are obtained 1.9 g of 6-(allyl-methyl-amino)-hexan-1-ol•hydrobromide as the crude product, MS: m/e 171 (M).
C) 10 g of 6-chloro-pyridine-2-carboxylic acid are dissolved in 50 ml of thionyl chloride and heated under reflux for 3.5 h. The solution is cooled and freed from excess thionyl chloride under reduced pressure. The crude product is taken up in 60 ml of methylene chloride and treated with 7.22 g of N,O-dimethyl-hydroxylamine•hydrochloride. 25 ml of NEt₃ in 30 ml of CH₂Cl₂ are added while cooling with ice and the solution is stirred at RT for 1.5 h., the suspension is filtered and the filtrate is washed with dilute sodium hydroxide solution and saturated sodium chloride solution and dried. After concentration of the solution 13.12 g of 6-chloro-pyridine-2-carboxylic acid methoxy-methyl-amide are obtained as the crude product. 6.7 g of this amide in 40 ml of THF are added dropwise at −78° C. to a solution of 40 ml of n-BuLi (1.6M in hexane) and 15 g of 1,4-dibromobenzene in 140 ml of THF. The solution is stirred at −78° C. for 2 h. and at 0° C. for 1 h. and then treated with 60 ml of 2M HCl. The phases are separated, the inorganic phase is extracted with 50 ml of ether and the organic phases are washed with sat. NaHCO$_3$ solution and saturated sodium chloride solution and dried. The crude product is purified over silica gel with ethyl acetate:hexane (6:1) and recrystallized from ethyl acetate/hexane. There are obtained 6.75 g of (4-bromo-phenyl)-(6-chloro-pyridin-3-yl)-methanone, m.p 127.4° C., MS: m/e 295 (M, 1Br).

D) Analogously to Ex. 42.1.C):
a) from 6-chloro-pyridine-2-carboxylic acid via 6-chloro-pyridine-2-carboxylic acid methoxy-methyl-amide with methylmagnesium bromide in THF there is obtained 1-(6-chloro-pyridin-3-yl)-ethanone, MS: m/e 155 (M),
b) from 5-chloro-pyridine-2-carboxylic acid via 5-chloro-pyridine-2-carboxylic acid methoxy-methyl-amide with 1,4-dibromobenzene/n-butyllithium there is obtained (4-bromo-phenyl)-(5-chloro-pyridinyl-2-yl)-methanone, m.p. 117.5–119.5° C., MS: m/e 296 (M, 1Br).

42.2. Product 1.11 g of (4-bromo-phenyl)-(6-chloro-pyridin-3-yl)-methanone (Ex. 42.1.C), 696 mg of 6-(allyl-methyl-amino)-hexan-1-ol (Ex. 42.1.B), 880 mg of KOH, 552 mg of K$_2$CO$_3$ and 200 mg of dicyclohexano-[18]crown-6 are dissolved in 50 ml of toluene under argon and heated to 80° C. overnight. The suspension is again treated with 323 mg of 6-(allyl-methyl-amino)-hexan-1-ol and heated for a further 5 h. The reaction mixture is treated with H$_2$O and extracted with CH$_2$Cl$_2$. The organic phases are washed with sat. NaHCO$_3$ solution and sat. sodium chloride solution and dried. The crude product obtained is chromatographed in CH$_2$Cl$_2$:MeOH (95:5). There are obtained 1.02 g of yellow-brown oil, [6-[6-(allyl-methyl-amino)-hexyloxy]-pyridin-3-yl]-(4-bromo-phenyl)-methanone, which is dissolved in 15 ml of ethanol and treated with 261 mg of fumaric acid in 5 ml of ethanol. The solution is stirred at RT for 1 h., concentrated and the oil is evaporated several times and lyophilized. There are obtained 1.2 g of 6-[6-(allyl-methyl-amino)-hexyloxy]-pyridin-3-yl]-(4-bromo-phenyl)-methanone•fumarate (1:1) as a yellow oil, MS: m/e 430 (M).

EXAMPLE 43

Analogously to Example 42.2:
a) from (4-bromo-phenyl)-(6-chloro-pyridin-3-yl)-methanone (Ex. 42.1.C) and (E)-4-(allyl-methyl-amino)-but-2-en-1-ol (Ex. 42.1.A) in the presence of KOH and K$_2$CO$_3$ in toluene there is obtained (E)-[6-[4-(allyl-methyl-amino)-but-2-enyloxy]-pyridin-3-yl]-(4-bromo-phenyl)-methanone•fumarate (1:1), MS: m/e 401 (M$^+$, 1Br),
b) from (4-bromo-phenyl)-(5-chloro-pyridinyl-2-yl)-methanone (Ex. 42.1.Db) and (allyl-methyl-amino)-hexan-1-ol (Ex. 42.1.B) in the presence of KOH, K$_2$CO$_3$ and dicyclohexano-[18]crown-6 in toluene there is obtained [5-[6-(allyl-methyl-amino)-hexyloxy]-pyridin-2-yl]-(4-bromo-phenyl)-methanone•fumarate (1:1), MS: m/e 431 (M+H$^+$, 1Br).

EXAMPLE 44 a) The corresponding Grignard compound is prepared from 22.6 g of 4-bromobiphenyl with 2.36 g of magnesium in 75 ml of THF. A solution of 8.0 g of 5-methoxy-2H-3,4-dihydropyrrole in 25 ml of THF is added dropwise to this solution. The mixture is boiled at reflux for 5 hrs., then poured into a saturated solution of ammonium chloride, extracted with ethyl acetate, dried and concentrated. The residue is recrystallized from isopropanol, with 1.93 g of 5-biphenylyl-2H-3,4-dihydropyrrole being isolated, m.p. 230° C.

b) 1.85 g of 5-biphenylyl-2H-3,4-dihydropyrrole are dissolved in 50 ml of methanol and treated with 0.38 g of sodium borohydride. The mixture is stirred at room temperature for one hour, then concentrated, treated with water, extracted with ethyl acetate, dried and concentrated. 1.48 g of 2-biphenylyl-pyrrolidine, m.p. 50–53° C., are thus isolated.

c) 1.40 g of 2-biphenylyl-pyrrolidine are dissolved in 40 ml of methanol and treated with 1.5 ml of a 36% aqueous formaldehyde solution. The mixture is treated with 0.38 g of sodium borohydride and stirred in an ice bath for 15 min., concentrated, extracted with ethyl acetate, dried and concentrated. The residue is dissolved in a small amount of ether and treated with a sat. solution of HCl gas in ether. The colourless precipitate is filtered off under suction and dried. 1.57 g of N-methyl-2-biphenylyl-pyrrolidine hydrochloride are isolated.

d) 350 mg of N-methyl-2-biphenylyl-pyrrolidine hydrochloride are suspended in 10 ml of carbon disulphide and treated with 341 mg of aluminium chloride. A solution of 842 mg of 4-bromo-benzoyl chloride in 3 ml of carbon disulphide is added dropwise to this viscous mass. The mixture is held at reflux for 2 hours and evaporated. The residue is triturated in toluene and then in ethyl acetate, with 90 mg of (±)(4-bromophenyl)-[4'-(1-methylpyrrolidin-2-yl)-biphenyl-4-yl]-methanone•hydrochloride, m.p. 225° C., being obtained.

EXAMPLE 45 a) The corresponding Grignard compound is prepared from 16 g of 4-bromotoluene and 2.23 g of magnesium in 150 ml of THF. This is added dropwise at room temperature to a solution of 10 g of 2-bromothiophene, 3 g of palladium acetate and 1.27 g of triphenylphosphine in 150 ml of THF. The mixture is boiled at reflux under argon for 3.5 hrs., then poured on to ice-water and extracted with ethyl acetate. Chromatography on silica gel (toluene) gives 9.06 g of 2-p-tolyl-thiophene.

b) 1.02 g of (4-bromophenyl)-(5-p-tolyl-thiophen-2-yl)-methanone, m.p. 172–174° C., are obtained from 1.0 g of 2-p-tolyl-thiophene, 840 mg of aluminium chloride and 1.46 g of 4-bromobenzoyl chloride in 20 ml of carbon disulphide in a Friedel-Crafts reaction after chromatography on silica gel (methylene chloride).

c) 0.5 g of (4-bromophenyl)-(5-p-tolyl-thiophen-2-yl)-methanone and 262 mg of N-bromosuccinimide in 20 ml of carbon tetrachloride are held at reflux for 19 hrs. after the addition of a spatula tip of azaisobutyronitrile, concentrated and the residue is chromatographed on silica gel (methylene chloride/hexane). 517 mg of [5-(4-bromomethyl-phenyl)-thiophen-2-yl]-4-bromophenyl-methanone, m.p. 184° C. (decomposition), are isolated.

d) 435 mg of [5-(4-bromomethyl-phenyl)-thiophen-2-yl]-4-bromophenyl-methanone are dissolved in 25 ml of acetone, 300 mg of potassium carbonate and 0.15 ml of N-allyl-methyl-amine are added and the mixture is held at reflux under argon for 4 hrs., treated with ice-water, extracted with ethyl acetate, dried and chromatographed on silica gel (ethyl acetate/hexane). 219 mg of 5-(4-[(allyl-methylamino)-methyl]-phenyl)-thiophen-2-yl)-(4-bromphenyl)-methanone, m.p. 131–133° C., are isolated.

EXAMPLE 46

Analogously to Example 45:
a) from [5-(4-bromomethyl-phenyl)-thiophen-2-yl]-4-bromo-phenyl-methanone with dimethylamine in ethanol there is obtained 5-(4-[dimethylamino)-methyl]-phenyl)-thiophen-2-yl)-(4-bromo-phenyl)-methanone, m.p. of 149–152°,
b) from 2-p-tolyl-thiophene and 2,4-difluoro-benzoyl chloride via (2,4-difluoro-phenyl)-5-p-tolyl-thiophen-2-yl)-methanone and [5-(4-bromo-methyl-phenyl)-thiophen-2-yl]-4-(2,4-difluoro-phenyl)-methanone with N-allyl-methyl-amine there is obtained 5-(4-[(allyl-methylamino)-methyl]-phenyl)-thiophen-2-yl)-(4-(2,4-difluorophenyl))-methanone, m.p. of 82–84° C.,
c) from 2-p-tolyl-thiophene and 2,4-difluoro-benzoyl chloride via (2,4-difluoro-phenyl)-5-p-tolyl-thiophen-2-yl)-methanone and [5-(4-bromomethyl-phenyl)-thiophen-2-yl]-4-(2,4-difluoro-phenyl)-methanone with potassium carbonate and dimethylamine solution in ethanol there is obtained (2-dimethylamino-4-fluoro-phenyl)-[5-(4-dimethylaminomethyl-phenyl)-thiophen-2-yl]-methanone, MS: m/e 382 (M).

EXAMPLE 47

47.1. Starting Material

Analogously to Example 45, from 4-bromo-toluene and 3-bromo-anisole via 3-methoxy-4'-methyl-biphenyl, (4-bromo-phenyl)-(3-methoxy-4'-methyl-biphenyl-4-yl)-methanone and (4'-bromomethyl-3-methoxy-biphenyl-4-yl)-(4-bromo-phenyl)-methanone with dimethylamine in ethanol there is obtained (4-bromo-phenyl)-(4'-dimethylaminomethyl-3-methoxy-biphenyl-4-yl)-methanone, m.p. of the hydrochloride 252–255° C.

47.2 Product 700 mg of (4-bromo-phenyl)-(4'-dimethylaminomethyl)-3-methoxy-biphenyl-4-yl)-methanone are held at reflux for 18 hrs. in 15 ml of a 62% HBr solution, treated with ice-water, extracted with ethyl acetate and chromatographed on silica gel (methylene chloride/methanol). 205 mg of (4-bromophenyl)-(4'-dimethylaminomethyl-3-hydroxy-biphenyl-4-yl)-methanone, m.p. 85–88° C., are isolated.

EXAMPLE 48

A solution of 211 mg of (RS)-[4'-[allyl-methyl-amino)-methyl]-biphenyl-4-yl]-(4-bromo-phenyl)-methanol is treated in 3 ml of methylene chloride with 0.065 ml of diethylamino-sulphur trifluoride at −78° C. After 3 hrs. at room temperature the mixture is again cooled to −78° C. and 0.065 ml of diethyl amino-sulphur trifluoride is added. After 16 hrs. at room temperature the mixture is poured into ice-cold saturated sodium hydrogen carbonate solution and extracted with methylene chloride. After chromatography over silica gel with methylene chloride/methanol (2%–5%), dissolution of the residue in ethanol and reaction with 108 mg of fumaric acid there is obtained (RS)-allyl-[4'-[(4-bromo-phenyl)-fluoro-methyl]-biphenyl-4-ylmethyl]-methyl-amine•fumarate (1:1), MS: m/e 423 (M, 1Br).

EXAMPLE 49

49.1. Starting Material a) A mixture of 7 g of tert-butyl (4-hydroxy)-piperidine-1-carboxylate and 210 ml of 1,6-dibromohexane is treated firstly with 3.5 g of tetrabutylammonium hydrogen sulphate and then with 210 ml of 50% aqueous sodium hydroxide solution. After stirring at room temperature for 5 days the reaction mixture is diluted with methylene chloride, the organic phase is separated and the aqueous phase is extracted with methylene chloride. The combined organic phases are washed with saturated sodium chloride solution, dried and concentrated. The brown oil is chromatographed on silica gel with ethyl acetate-hexane. 10.9 g of tert-butyl 4-(6-bromo-hexyloxy)-piperidine-1-carboxylate are obtained.

b) The ester obtained is treated with 2.9 ml of N-allyl-methyl-amine, 4.1 g of potassium carbonate and 30 ml of acetone. The mixture is stirred at room temperature for 2 days, filtered and evaporated. Subsequently, the Boc group is cleaved off with 34 ml of trifluoroacetic acid in 100 ml of methylene chloride. After concentration, azeotropic distillation of the trifluoroacetic acid with toluene and drying there are obtained 14 g of allyl-methyl-[6-(piperidin-4-yloxy)-hexyl]-amine, MS: m/e 255 (M+H$^+$).

49.2. Product 3 g of allyl-methyl-[6-(piperidin-4-yloxy)-hexyl]-amine (Ex. 49.1) are dissolved in 50 ml of methylene chloride and treated with 5.3 ml of Hünig Base (di-isopropyl-ethylamine) and 1.9 g of 4-bromo-phenylsulphonyl chloride. The reaction mixture is stirred at room temperature for 3 hours, treated with aqueous sodium hydrogen carbonate solution and extracted with methylene chloride. The organic phases are washed with saturated sodium chloride solution, dried and concentrated. The brown oil is purified on silica gel with ethyl acetate/methanol (9:1). There are obtained 2.6 g of allyl-[6-[1-(4-bromo-phenylsulphonyl)-piperidin-4-yloxy]-hexyl]-methyl-amine which are converted into the fumarate, MS: m/e 473 (M+H$^+$, 1Br).

EXAMPLE 50

Analogously to Example 49.2,
a) from allyl-methyl-[6-(piperidin-4-yloxy)-hexyl]-amine and 4-bromobenzoyl chloride there is obtained [4-[6-(allyl-methyl-amino)-hexyloxy]-piperidin-1-yl]-1-(4-bromo-phenyl) methanone which is converted into the hydrochloride with 4M hydrochloric acid solution in ether, MS: m/e 437 (M+H$^+$, 1Br).
b) from allyl-methyl-[6-(piperidin-4-yloxy)-hexyl]-amine and 4-bromophenacyl bromide there is obtained 2-[4-[6-(allyl-methyl-amino)-hexyloxy]-piperidin-1-yl]-1-(4-bromo-phenyl)-ethanone which is converted with 4M hydrochloric acid solution in ether into 2-[4-[6-(allyl-methyl-amino)-hexyloxy]-piperidin-1-yl]-1-(4-bromo-phenyl)-ethanone•hydrochloride (1:2), MS: m/e 451 (M+H$^+$, 1Br).

EXAMPLE 51

A mixture of 3.0 g of [4-[(E)-4-(allyl-methyl-amino)-but-2-enyloxy]-phenyl]-(4-bromo-phenyl)-methanone•hydrobromide, 0.77 g of O-methylhydroxyl-amine•hydrochloride and 1.07 g of sodium acetate in 100 ml of ethanol is heated under reflux for 3 days. The reaction mixture is concentrated and the residue is treated with 100 ml of saturated aqueous NaHCO$_3$ solution and extracted with ethyl acetate. The organic extracts are washed with saturated sodium chloride solution, dried and evaporated. The residue is purified over silica gel with ethyl acetate-hexane-triethylamine (39:60:1). There are obtained 2.22 g of (E)- and/or (Z)-14-[(E)-4-(allyl-methyl-amino)-but-2-enyloxy]-phenyl]-(4-bromo-phenyl)-methanone O-methyl-oxime which are treated with with 103 ml of 0.05M fumaric acid solution. After stirring the solution is lyophilized. There is obtained (E)- and/or (Z)-[4-[(E)-4-(ally-methyl-amino)-but-2-enyloxy]-phenyl]-(4-bromo-phenyl)-methanone-0-methyl-oxime•fumarate (1:1) as an oil. MS: m/e 429 (M+H$^+$, 1Br).

EXAMPLE 52

Analogously to Example 51:
a) from [4-[(E)-4-(allyl-methyl-amino)-but-2-enyloxy]-phenyl]-(4-bromo-phenyl)-methanone•hydrobromide and hydroxylamine•hydrochloride there is obtained (E)- and/or (Z)-[4-[(E)-4-(allyl-methyl-amino)-but-2-enyloxy]-phenyl]-(4-bromo-phenyl)-methanone oxime, MS: m/e 414 (M$^+$, 1Br),
b) from [4-[(E)-4-(allyl-methyl-amino)-but-2-enyloxy]-phenyl]-(4-bromo-phenyl)-methanone•hydrobromide and O-tert-butylhydroxylamine•hydrochloride there is obtained (E)- and/or (Z)-[4-[(E)-4-allyl-methyl-amino)-but-2-enyloxy]-phenyl-(4-bromo-phenyl)-methanone O-tert-butyl oxime which is converted into the fumarate, MS: m/e 397 [M-OC(CH$_3$)$_3$, 1Br],
c) from [4-[(E)-4-(allyl-methyl-amino)-but-2-enyloxy]-phenyl]-(4-bromo-phenyl)-methanone•hydrobromide and O-allylhydroxylamine•hydrochloride there is obtained (E)- and/or (Z)-[4-[(E)-4-(allyl-methyl-amino)-but-2-enyloxy]-phenyl]-(4-bromo-phenyl)-methanone O-allyl oxime which is converted into the fumarate, MS: m/e 455 (M+H$^+$, 1Br),
d) from [4-[6-(allyl-methyl-amino)-hexyloxy]-2-fluoro-phenyl]-(4-bromo-phenyl)-methanone•hydrobromide and hydroxylamine•hydrochloride there is obtained (E)- and/or (Z)-[4-[6-(allyl-methyl-amino)-hexyloxy]-2-fluoro-phenyl]-(4-bromo-phenyl)-methanone oxime which is converted into the fumarate, MS: m/e 463 (M+H$^+$, 1Br).

EXAMPLE 53 a) A solution of 10.7 g of 1,4-dibromobenzene in 80 ml of absolute THF is cooled to −78° C. and treated within 30 min. with 25.6 ml of 1.6M butyllithium in hexane. After 30 min. 6.08 g of (4E,8E)-(RS)-4,8-dimethyl-10-(tetrahydro-pyran-2-yloxy)-deca4,8-dienal in 20 ml of THF are added dropwise. After 1 hr. at −78° C. the bath is removed until the suspension has dissolved and subsequently 7.2 ml of acetic acid in 10 ml of ether are added dropwise at −78° C. The solution is poured into saturated ammonium chloride solution/ethyl acetate. The organic phase is washed with saturated sodium bicarbonate solution and 10% sodium chloride solution, dried and evaporated. After silica gel chromatography with hexane/ethyl acetate 95:5 there are obtained 4.3 g of (4E,8E)-1-(4-bromo-phenyl)-4,8-dimethyl-10-(tetrahydro-pyran-2-yloxy)-deca-4,8-dien-1-ol.
b) A solution of 3.4 g of (4E,8E)-1-(4-bromo-phenyl)-4,8-dimethyl-10-(tetrahydro-pyran-2-yloxy)-deca-4,8-dien-1-ol in 60 ml of methylene chloride is treated in succession with 0.29 g of sodium carbonate and 7.5 g of manganese(IV) oxide. After stirring for 3 hrs. the mixture is filtered and again treated in methylene chloride with 0.29 g of sodium carbonate and 7.5 g of manganese (IV) oxide. After filtration and silica gel chromatography with hexane/ethyl acetate (9:1) there are obtained 1.98 g of (4E,8E)-(RS)-1-(4-bromo-phenyl)-4,8-dimethyl-10-(tetrahydro-pyran-2-yloxy)-deca-4,8-dien-1-one.
c) A solution of 1.98 g of (4E,8E)-(RS)-1-(4-bromo-phenyl)-4,8-dimethyl-10-(tetrahydro-pyran-2-yloxy)-deca-4,8-dien-1-one in 4 ml of methylene chloride is treated with 2.22 g of triphenylphosphine dibromide under argon at −5° C. After 10 min. the mixture is left to warm to 0° C., then stirred at 0° C. and evaporated. The residue is dissolved in 16 ml of dimethylacetamide and treated dropwise at 0° C. with 0.87 ml of N-allyl-methyl-amine. Then, the solvent is removed, the residue is taken up in methylene chloride/saturated sodium bicarbonate, the organic phase is dried and concentrated and the residue is purified over silica gel with methylene chloride/methanol (2.5% to 5%). Pure (4E,8E)-10-(allyl-methyl-amino)-1-(4-bromo-phenyl)-4,8-dimethyl-deca4,8-dien-1-one is dissolved in ethanol with 0.17 g of fumaric acid, concentrated and the residue is precipitated from ethyl acetate with pentane. There is obtained 0.78 g of (4E,8E)-10-(allyl-methyl-amino)-1-(4-bromo-phenyl)-4,8-dimethyl-deca-4,8-dien-1-one•fumarate (1:1), MS: m/e 404 (M+H$^+$, 1Br).

EXAMPLE 54

Analogously to Example 53:
a) from (4E,8E)-(RS)-4,8-dimethyl-10-(tetrahydro-pyran-2-yloxy)-deca-4,8-dienal via (4E,8E)-1-(4-bromo-phenyl)-4,8-dimethyl-10-(tetrahydro-pyran-2-yloxy]-deca-4,8-dien-1-ol and (4E,8E)-(RS)-1-(4-bromo-phenyl)-4,8-dimethyl-10-(tetrahydro-pyran-2-yloxy]-deca-4,8-dien-1-one with dimethylamine there is obtained (4E,8E)-1-(4-bromo-phenyl)-10-dimethylamino-4,8-dimethyl-deca-4,8-dien-1-one•fumarate (1:1), MS: m/e 377 (M, 1Br).
b) from (4E,8E)-(RS)-4,8-dimethyl-10-(tetrahydro-pyran-2-yloxy)-deca-4,8-dienal with magnesium 4-methyl-pent-3-enyl bromide via (9E,13E)-2,9,13-trimethyl-15-(tetrahydro-pyran-2-yloxy)-pentadeca-2,9,13-trien-6-ol and (9E,13E)-(RS)-2,9,13-trimethyl-15-(tetrahydro-pyran-2-yloxy)-pentadeca-2,9,13-trien-6-one there is obtained (9E,13E)-15-(allyl-methyl-amino)-2,9,13-trimethyl-pentadeca-2,9,13-trien-6-one•fumarate (1:1), MS: m/e 331 (M).
c) from (2E,6E)-(RS)-2,6-dimethyl-8-(tetrahydro-pyran-2-yloxy)-octa-2,6-dienal with magnesium 4-methyl-pent-3-enyl bromide via (7E,11E)-2,7,11-trimethyl-13-(tetrahydro-pyran-2-yloxy)-trideca-2,7,11-trien-6-ol and (7E,11E)-(RS)-2,7,11-trimethyl-13-(tetrahydro-pyran-2-yloxy)-trideca-2,7,11-trien-6-one there is obtained (7E,11E)-13-(allyl-methyl-amino)-2,7,11-trimethyl-trideca-2,7,11-trien-6-one•fumarate (1:1), MS: m/e 303 (M).
d) from (2E,6E)-(RS)-2,6-dimethyl-8-(tetrahydro-pyran-2-yloxy)-octa-2,6-dienal with magnesium 4-methyl-pent-3-enyl bromide via (7E,11E)-2,7,11-trimethyl-13-(tetrahydro-pyran-2-yloxy)-trideca-2,7,11-trien-6-ol and (7E,11E)-(RS)-2,7,11-trimethyl-13-(tetrahydro-pyran-2-yloxy)-trideca-2,7,11-trien-6-one there is obtained (7E,11E)-13-(allyl-methyl-amino)-2,7,11-trimethyl-trideca-2,7,11-trien-6-one from which, after treatment with 4M hydrochloric acid in ether, there is obtained a mixture of (7E,11E)- and (7Z,11E)-13-(allyl-methyl-amino)-2,7,11-trimethyl-trideca-2,7,11-trien-6-one•hydrochloride (1:1), MS: m/e 303 (M).
e) from (2E,6E)-(RS)-2,6-dimethyl-8-(tetrahydro-pyran-2-yloxy)-octa-2,6-dienal via (2E,6E)-(RS)-1-(4-bromo-phenyl)-2,6-dimethyl-8-(tetrahydro-pyran-2-yloxy)-octa-2,6-dien-1-ol and (2E,6E)-(RS)-1-(4-bromo-phenyl)-2,6-dimethyl-8-(tetrahydro-pyran-2-yloxy)-octa-2,6-dien-1-one there is obtained (2E,6E)-8-(allyl-methyl-amino)-1-(4-bromo-phenyl)-2,6-dimethyl-octa-2,6-dien-1-one•fumarate (1:1), MS: m/e 376 (M+H$^+$, 1Br).
f) from (2E,6E)-(RS)-2,6-dimethyl-8-(tetrahydro-pyran-2-yloxy)-octa-2,6-dienal with magnesium pent-4-enyl bromide via (7E,11E)-(RS)-7,11-dimethyl-13-(tetrahydro-pyran-2-yloxy)-trideca-1,7,11-trien-6-ol and (7E,11E)-(RS)-7,11-dimethyl-13-(tetrahydro-pyran-2-yloxy)-trideca-1,7,11-trien-6-one there is obtained (7E,11E)-13-(allyl-methyl-amino)-7,11-dimethyl-trideca-1,7,11-trien-6-one•hydrochloride (1:1), MS: m/e 289 (M).

EXAMPLE 55

From (2E,6E)-(RS)-2,6-dimethyl-8-(tetrahydro-pyran-2-yloxy)-octa-2,6-dienal via (2E,6E)-1-(4-bromo-phenyl)-2,6- dimethyl-8-(tetrahydro-pyran-2-yloxy)-octa-2,6-dien-1-ol (without oxidation) there is obtained (2E,6E)-(RS)-8-(allyl-methyl-amino)-1-(4-bromo-phenyl)-2,6-dimethyl-octa-2,6-dien-1-ol•fumarate (1:1), MS: m/e 376 (M-H, 1Br).

EXAMPLE 56

A solution of 188 mg of (2E,6E)-8-(allyl-methyl-amino)-1-(4-bromo-phenyl)-2,6-dimethyl-octa-2,6-dien-1-one in 4 ml of benzene is treated with a solution of 210 mg of sodium hydrogen carbonate, 61 mg of tricaprylylmethylammonium chloride and 245 mg of sodium dithionite in 4 ml of water and boiled at 80° C. for 20 min. A further 245 mg of sodium dithionite are added and, after a further 20 min. at 80° C., the mixture is worked up with water/ether. The residue is purified over silica gel with methylene chloride/methanol (2%), treated with 22 mg of fumaric acid in ethanol and concentrated. There are obtained 102 mg of (E)-(RS)-8-(allyl-methyl-amino)-1-(4-bromo-phenyl)-2,6-dimethyl-oct-6-en-1-one•fumarate (1:1), MS: m/e 376 (M-H, 1Br).

EXAMPLE 57

57.1. Starting Materials

A.a) A solution of 105 g of 80% sodium chlorite and 100 g of sodium dihydrogen phosphate in 1 l of water is added within 30 min. to 50 g of (4E,8E)-(RS)-4,8-dimethyl-10-(tetrahydro-pyran-2-yloxy)-deca-4,8-dienal in 1.5 l of tert-butanol and 1.5 l of 2-methyl-2-butene. After 2½ hrs. at room temperature the mixture is concentrated and the residue is taken up in methylene chloride, washed with ice-water and 10% potassium hydrogen sulphate solution and dried. 46.5 g of (4E,8E)-(RS)-4,8-dimethyl-10-(tetrahydro-pyran-2-yloxyl)-deca-4,8-dienoic acid are obtained. The acid obtained is dissolved in 590 ml of methylene chloride and treated at 0° C. with 14.9 ml of N-allyl-methyl-amine, 32.0 g of N-(3-dimethylaminopropyl)-N'-ethylcarbodiimide hydrochloride and 1.88 g of dimethylaminopyridine. After 3 hrs. at room temperature and working up with methylene chloride/10% potassium hydrogen sulphate and subsequently saturated sodium hydrogen carbonate solution the organic phase is dried and concentrated. 52.3 g of crude (4E,8E)-(RS)-4,8-dimethyl-10-(tetrahydro-pyran-2-yloxy)-deca-4,8-dienoic acid allyl-methylamide are obtained.

b) The allyl-methylamide is dissolved in 15 ml of methanol and added dropwise to a suspension of 80 g of an acidic ion exchanger in 550 ml of methanol. After stirring for 5 min. the mixture is filtered, concentrated and the residue is purified over silica gel with methylene chloride/methanol (9:1). 29.1 g of (4E,8E)-10-hydroxy-4,8-dimethyl-deca-4,8-dienoic acid allyl-methylamide are obtained. 23.6 g of the crude amide are dissolved in 20 ml of THF and added dropwise to 3.5 g of lithium aluminium hydride in 165 ml of THF in such a manner that the temperature does not rise above 28° C. After 2 hrs. the reaction mixture is treated with 10 ml of water, dried, filtered and concentrated. The oil is taken up in 10% potassium hydrogen sulphate/ether, the aqueous phase is adjusted to pH 10 with saturated sodium carbonate solution and extracted with methylene chloride. After drying and concentration of the organic phase there are obtained 6.9 g of (4E,8E)-10-(allylmethyl-amino)-3,7-dimethyl-deca-2,6-dien-1-ol, MS: m/e 234 (M—OH).

c) The alcohol obtained is dissolved in 130 ml of toluene and treated with 22 g of manganese(IV) oxide. Then, the mixture is filtered and treated a further twice in toluene with manganese(IV) oxide. 5.5 g of (2E,6E)-10-(allylmethyl-amino)-3,7-dimethyl-deca-2,6-dienal are obtained after filtration.

B) Analogously to Example 57.1.A), from (2E,6E)-(RS)-2,6-dimethyl-8-(tetrahydro-pyran-2-yloxy)-octa-2,6-dienal via (2E,6E)-(RS)-2,6-dimethyl-8-(tetrahydro-pyran-2-yloxy)-octa-2,6-dienoic acid allyl-methylamide and (2E,6E)-8-(allyl-methyl-amino)-3,7-dimethyl-octa-2,6-dien-1-ol there is obtained (2E,6E)-8-(allyl-methyl-amino)-3,7-dimethyl-octa-2,6-dienal which is used directly.

57.2. Product

A solution of 6.4 g of 1,4-dibromobenzene in 50 ml of absolute THF is cooled −78° C. and treated within 30 min. with 15.3 ml of 1.6M butyllithium in hexane. After 1 hr. 3.0 g of (2E,6E)-10-(allyl-methyl-amino)-3,7-dimethyl-deca-2,6-dienal (Ex. 57.1.A) in 12 ml of THF are added dropwise. After 1½ hr. at −78° C. the bath is removed until the suspension has dissolved. Subsequently, 4.5 ml of acetic acid in 6 ml of ether are added dropwise at −78° C. Then, the mixture is poured into saturated ammonium chloride solution/ethyl acetate. The organic phase is washed with saturated sodium bicarbonate solution and 10% sodium chloride solution, dried and evaporated. After silica gel chromatography with methylene chloride/methanol (95:5) there are obtained 1.14 g of (2E,6E)-(RS)-10-(allyl-methyl-amino)-1-(4-bromo-phenyl)-3,7-dimethyl-deca-2,6-dien-1-ol. This is dissolved in ethanol with 0.29 g of fumaric acid, evaporated and converted with ethyl acetate/ether into 0.91 g of (2E,6E)-(RS)-10-(allyl-methyl-amino)-1-(4-bromphenyl)-3,7-dimethyl-deca-2,6-dien-1-ol•fumarate (1:1), MS: m/e 406 (M+H$^+$, 1Br).

EXAMPLE 58

Analogously to Example 57.2:

from (2E,6E)-8-(allylmethyl-amino)-3,7-dimethyl-octa-2,6-dienal (Ex. 57.1.B) and butyllithium/1,4-dibromobenzene there is obtained (2E,6E)-(RS)-8-(allyl-methyl-amino)-1-(4-bromo-phenyl)-3,7-dimethyl-octa-2,6-dien-1-ol•fumarate (1:1), MS: m/e 378 (M+H$^+$, 1Br).

EXAMPLE 59

A solution of 162 mg of (2E,6E)-(RS)-10-(allyl-methyl-amino)-1-(4-bromo-phenyl)-3,7-dimethyl-deca-2,6-dien-1-ol (Ex. 57.2) in 6 ml of methylene chloride is treated in succession with 28 mg of sodium carbonate and 730 mg of manganese(IV) oxide. After stirring for 2 hrs. the mixture is filtered, concentrated and the residue is dissolved in ethanol with 28 mg of fumaric acid, evaporated and precipitated with ethyl acetate/ether. There are obtained 87 mg of (2E,6E)-10-(allyl-methyl-amino)-1-(4-bromo-phenyl)-3,7-dimethyl-deca-2,6-dien-1-one•fumarate (1:1), MS: m/e 404 (M+H$^+$, 1Br).

EXAMPLE 60

Analogously to Example 59:

from (2E,6E)-(RS)-8-(allyl-methyl-amino)-1-(4-bromo-phenyl)-3,7-dimethyl-octa-2,6-dien-1-ol (Ex. 58) there is obtained (2E,6E)-8-(allyl-methyl-amino)-1-(4-bromo-phenyl)-3,7-dimethyl-octa-2,6-dien-1-one•fumarate (1:1), MS: m/e 376 (M+H$^+$, 1Br).

EXAMPLE 61

A solution of 230 mg of [2-amino-4-[6-(allyl-methyl-amino)-hexyloxy]-phenyl-3-(4-bromo-phenyl)-methanone (Ex. 36) in 0.5 ml of formic acid and 2 ml of formamide is boiled at 165° C. for 5 min., concentrated at 170° C./0.1 Torr in a bulb-tube and converted into the free amine with methylene chloride/saturated sodium bicarbonate solution. After purification over silica gel with methylene chloride/methanol (2.5%) as the eluent there are obtained 30 mg of N-[5-[6-(allyl-methyl-amino)-hexyloxy]-2-(4-bromo-benzoyl)-phenyl]-formamide, MS: m/e 473 (M+H$^+$, 1Br).

Pharmaceutical dosage forms having the following composition can be produced in a manner known per se:

EXAMPLE A

Tablets containing 5 mg of (E)-(RS)-1-[4-[4-(allyl-methyl-amino)-but-2-enyloxy]-phenyl]-(4-bromo-phenyl)-ethanol as the active ingredient

| Composition: | 1 tablet contains: |
|---|---|
| Active ingredient | 5.0 mg |
| Lactose | 148.0 mg |
| Potato starch | 65.0 mg |
| Magnesium stearate | 2.0 mg |
| | 220.0 mg |

EXAMPLE B

Dragées Containing 5 mg of (E)-(RS)-1-[4-[4-(Allyl-methyl-amino)-but-2-enyloxy]-phenyl]-(4-bromo-phenyl)-ethanol The tablets from Ex. A are covered according to a known procedure with a coating which consists essentially of sugar and talc. The finished dragées are polished using beeswax.

Dragée weight: 300 mg

EXAMPLE C

Suppositories containing 5 mg of (E)-(RS)-1-[4-[4-(allyl-methyl-amino)-but-2-enyloxy]-phenyl]-(4-bromo-phenyl)-ethanol as the active ingredient

| Composition: | 1 suppository contains: |
|---|---|
| Active ingredient | 5.0 mg |
| Suppository mass (e.g. Witepsol W 45 ®) | 1695.0 mg |
| | 1700.0 mg |

EXAMPLE D

Capsules containing 5 mg of (E)-(RS)-1-[4-[4-(allyl-methyl-amino)-but-2-enyloxy]-phenyl]-(4-bromo-phenyl)-ethanol as the active ingredient

| Composition: | 1 capsule contains: |
|---|---|
| Active ingredient | 5.0 mg |
| Lactose | 82.0 mg |
| Starch | 82.0 mg |
| Magnesium stearate | 1.0 mg |
| | 170.0 mg |

What is claimed is:
1. A compound of the formula:

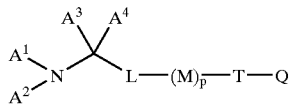

I wherein
$A^1$ is $C_1$–$C_{20}$ alkyl,
$A^2$ is OH, $C_3$–$C_6$ cycloalkyl, $C_3$–$C_6$ cycloalkyl-$C_1$–$C_{20}$-alkyl, unsubstituted $C_1$–$C_{20}$ alkyl, unsubstituted $C_3$–$C_{20}$ alkenyl, $C_1$–$C_{20}$ alkyl substituted by $R^1$, $CONH_2$ or CN, or $C_3$–$C_{20}$ alkenyl substituted by $R^1$, $CONH_2$ or CN, and
$A^3$ and $A^4$ are each independently hydrogen or $C_1$–$C_{20}$ alkyl; or
$A^1$ is $C_3$–$C_{20}$ alkenyl,
$A^2$ is $C_3$–$C_6$ cycloalkyl, $C_3$–$C_6$ cycloalkyl-$C_1$–$C_{20}$-alkyl, unsubstituted $C_1$–$C_{20}$ alkyl, unsubstituted $C_3$–$C_{20}$ alkenyl, $C_1$–$C_{20}$ alkyl substituted by $R^1$, $CONH_2$ or CN, or $C_3$–$C_{20}$ alkenyl substituted by $R^1$, $CONH_2$ or CN, and when $A^1$ is $C_1$–$C_{20}$ alkyl, and
$A^3$ and $A^4$ are each independently hydrogen or $C_1$–$C_{20}$ alkyl; or
$A^1$ and $A^2$ together form a $C_2$–$C_8$ alkylene, $C_4$–$C_8$ alkenylene, $C_6$–$C_8$ alkadienylene, $R^1$ substituted $C_2$–$C_8$ alkylene, $R^1$ substituted $C_4$–$C_8$ alkenylene, or $R^1$ substituted $C_6$–$C_8$ alkadienylene group $A^1$-$A^2$, or
$A^1$ and $A^2$ together form a $C_2$–$C_8$ alkylene, $C_4$–$C_8$ alkenylene, $C_6$–$C_8$ alkadienylene, $R^1$ substituted $C_2$–$C_8$ alkylene, $R^1$ substituted $C_4$–$C_8$ alkenylene, or $R^1$ substituted $C_6$–$C_8$ alkadienylene group $A^1$-$A^2$, wherein one or two C atoms are replaced by one or two groups selected from the group consisting of N atoms and $N(C_1$–$C_{20}$ alkyl), or
$A^1$ and $A^3$ together form a $C_2$–$C_8$ alkylene, $C_4$–$C_8$ alkenylene, $C_6$–$C_8$ alkadienylene, $R^1$ substituted $C_2$–$C_8$ alkylene, $R^1$ substituted $C_4$–$C_8$ alkenylene, or $R^1$ substituted $C_6$–$C_8$ alkadienylene group $A^1$-$A^3$, or
$A^1$ and $A^3$ together form a $C_2$–$C_8$ alkylene, $C_4$–$C_8$ alkenylene, $C_6$–$C_8$ alkadienylene, $R^1$ substituted $C_2$–$C_8$ alkylene, $R^1$ substituted $C_4$–$C_8$ alkenylene, or $R^1$ substituted $C_6$–$C_8$ alkadienylene group $A^1$-$A^3$, wherein one or two C atoms are replaced by one or two groups selected from the group consisting of N atoms and $N(C_1$–$C_{20}$ alkyl);
$R^1$ is OH, oxo, $C_1$–$C_{20}$ alkyl(O), $C_1$–$C_{20}$ alkyl(S) or di($C_1$–$C_{20}$ alkyl)amino bonded to a saturated C atom of $A^2$, $A^1$-$A^2$ or $A^1$-$A^3$, provided that a C atom substituted by $R^1$ or an unsaturated C atom present in $A^1$, $A^2$, $A^1$-$A^2$ or $A^1$-$A^3$ must be bonded in a position other than the α-position to $N(A^1A^2)$;
p=1 and L is phenylene, $C_4$–$C_{11}$ alkylene which has at least 4 C atoms between the two free valencies or $C_3$–$C^{11}$ alkenylene which has at least 3 C atoms between the two free valencies, and which is bonded to M directly or via O, NH or $N(C_1$–$C_{20}$ alkyl) or $N(C_1$–$C_{20}$ alkanoyl), or L is $C_3$–$C_6$ cycloalkylene-$C_1$–$C_{20}$-alkylene, or
p=0 and L is $C_6$–$C_{11}$-alkenylene or $C_6$–$C_{11}$-alkadienylene, bonded to T;
M is thienylene, pyridylene, 1,4-phenylene, 1,4-phenylene substituted by at least one substituent selected from the group consisting of $C_1$–$C_{20}$ alkyl, halogen, $N(R^2,R^{21})$, $CONH_2$, CN, $NO_2$, $CF_3$, OH, $C_1$–$C_{20}$ alkyl(O), $C_1$–$C_{20}$ alkyl(S), 1,2,4-triazol-1-yl and tetrazol-1-yl, or a group of the formula:

($M^1$)

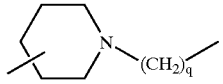

q is 1 or 0;

$R^2$ and $R^{21}$ are independently H, $C_1$–$C_{20}$ alkyl, $C_2$–$C_{20}$ alkenyl, $C_1$–$C_{20}$ alkanoyl or $SO_2$—($C_1$–$C_{20}$ alkyl);

T is CO, $CH(R^3)$, $C(R^4,R^5)$ or $C=NOR^6$ and, when M is a group $M^1$ and q=0, T can also be $SO_2$;

$R^3$ is OH, F, $C_1$–$C_{20}$ alkoxy or $C_1$–$C_{20}$ alkanoyloxy;

$R^4$ is OH and $R^5$ is $C_1$–$C_{20}$ alkyl, $C_2$–$C_{20}$ alkenyl, $C_2$–$C_{20}$ alkinyl, cycloalkyl or $CF_3$, or $R^4$ and $R^5$ together are the group $CH_2$, $CH_2O$ or $CH_2CH_2$;

$R^6$ is H, $C_1$–$C_{20}$ alkyl or $C_2$–$C_{20}$ alkenyl;

Q is $C_3$–$C_6$ cycloalkyl, $C(R^7,R^8)$, phenyl substituted by at least one substituent selected from the group consisting of $C_1$–$C_{20}$ alkyl, halogen, $N(R^9,R^{10})$, $CONH_2$, CN, $NO_2$, $CF_3$, 1,2,4-triazol-1-yl and tetrazol-1-yl, or a straight-chain $C_6$–$C_{13}$ alkyl, $C_6$–$C_{13}$ alkenyl, $C_6$–$C_{13}$ alkadienyl or $C_6$–$C_{13}$ alkatrienyl group Q' with 0 to 3 methyl substituents, and a group Q' can be substituted by at least one substituent selected from the group consisting of OH and $N(R^9,R^{10})$, $R^7$ and $R^8$ are $C_5$–$C_{11}$-alkyl, $C_5$–$C_{11}$-alkenyl or $C_5$–$C_{11}$-alkadienyl, and $R^9$ and $R^{10}$ are H, $C_1$–$C_{20}$ alkyl, $C_2$–$C_{20}$ alkenyl or $C_1$–$C_{20}$ alkanoyl, provided that (a) $A^2$ must not be $C_1$–$C_{20}$ alkyl or $C_3$–$C_{20}$ alkenyl, or $A^1$ and $A^2$ together must not be $C_2$–$C_8$ alkylene in a compound of formula I in which T is a group CO or CHOH, L is phenylene or an $C_4$–$C_{11}$ alkylene or $C_3$–$C_{11}$ alkenylene group bonded to M directly or via 0 or $N(C_1$–$C_{20}$ alkyl), M is 1,4-phenylene or 1,4-phenylene monosubstituted by $C_1$–$C_{20}$ alkyl, $C_1$–$C_{20}$ alkyl(O), halogen, CN, $NO_2$ or $CF_3$, and Q is substituted phenyl, $C_6$–$C_{13}$ alkenyl, $C_6$–$C_{13}$ alkyl or $C_6$–$C_{13}$ alkyl substituted by OH, (b) M must not be pyridylene in a compound of formula I in which $A^1$ and $A^2$ together are $C_2$–$C_8$ alkylene or $C_2$–$C_8$ alkylene substituted by $R^1$, $A^2$ is $C_1$–$C_{20}$ hydroxyalkyl or $A^1$ and $A^2$ are each $C_1$–$C_{20}$ alkyl, and (c) in a compound of formula I in which T is a group $C(OH, R^{51})$, wherein $R^{51}$ is $C_1$–$C_{20}$ alkyl, $C_2$–$C_{20}$ alkenyl, $C_2$–$C_{20}$ alkynyl or $C_3$–$C_6$ cycloalkyl, M is 1,4-phenylene or substituted 1,4-phenylene and L is an alkylene group bonded to M via a O atom, the alkylene must be a $C_5$–$C_{11}$ alkylene containing at least 5 C atoms between the 2 free valencies, or a pharmaceutically usable acid addition salt thereof.

2. The compound according to claim 1, wherein $A^2$ is $C_3$–$C_6$ cycloalkyl or $C_3$–$C_6$ cycloalkyl-$C_1$–$C_{20}$-alkyl and T is CO.

3. The compound according to claim 1 of the formula:

Ia

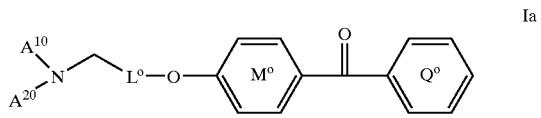

wherein $A^{10}$ is $C_1$–$C_{13}$ alkyl, $A^{20}$ is $C_3$–$C_6$ cycloalkyl or $C_3$–$C_6$ cycloalkyl-$C_1$–$C_{13}$-alkyl, $L^0$ is $C_4$–$C_{11}$ alkylene containing at least 4 C atoms between the two free valencies, $C_3$–$C_{11}$ alkenylene containing at least 3 C atoms between the two free valencies, or $C_3$–$C_6$ cycloalkylene-$C_1$–$C_{13}$-alkylene, $M^0$ is 1,4-phenylene or halogenated 1,4-phenylene, and $Q^0$ is phenyl substituted by halogen or CN.

4. The compound of claim 3, wherein $A^{10}$ is methyl, $A^{20}$ is cyclopropyl or cyclopropylmethyl, $L^0$ is n-pentylene, n-propenylene or cyclopropylenemethylene, $M^0$ is unsubstituted 1,4-phenylene or fluorinated 1,4-phenylene, and $Q^0$ is phenyl substituted by Br or CN.

5. The compound according to claim 4 selected from the group consisting of:

(4-bromo-phenyl)-[4-[6-(cyclopropyl-methyl-amino)-hexyloxy]-2-fluoro-phenyl]-methanone, (E)-(4-bromo-phenyl)-[4-[4-(cyclopropyl-methyl-amino)-but-2-enyloxy]-phenyl]-methanone,

[6-[6-(cyclopropyl-methyl-amino)-hexyloxy]-phenyl]-(4-brom-phenyl)-methanone, (E)-4-[4-[4-(cyclopropyl-methyl-amino)-but-2-enyloxy]-3-fluoro-benzoyl]-benzonitrile, (4-bromo-phenyl)-[4-[6-(cyclopropylmethyl-methyl-amino)-hexyloxy]-phenyl]-methanone, (1RS,2RS)-(4-bromo-phenyl)-[4-[2-[(cyclopropyl-methyl-amino)-methyl]-cyclopropylmethoxy]-phenyl]-methanone, and (1RS,2RS)-(4-bromo-phenyl)-[4-[2-[(cyclopropyl-methyl-amino)-methyl]-cyclopropylmethoxy]-3-fluoro-phenyl]-methanone.

6. The compound according to claim 2 selected from the group consisting of:

1-[4-[6-(Cyclopropylmethyl-methyl-amino)-hexyloxy]-2-fluoro-phenyl]-5-methyl-hex-4-en-1-one, 1-[4-[6-(cyclopropyl-methyl-amino)-hexyloxy]-2-fluoro-phenyl]-5-methyl-hex-4-en-1-one, (E)-(4-bromo-phenyl)-[4-[4-(cyclopropylmethyl-methyl-amino)-but-2-enyloxy]-phenyl]-methanone, (E)-4-[4-[4-(cyclopropyl-methyl-amino)-but-2-enyloxy]-3-fluoro-benzoyl]-benzamide, (1RS,2RS)-4-[4-[2-[(cyclopropyl-methyl-amino)-methyl]-cyclopropyl-methoxy]-3-fluoro-benzoyl]-benzonitrile, (1RS,2RS)-(4-bromo-phenyl)-[4-[2-[(cyclopropylmethyl-methyl-amino)-methyl]-cyclopropylmethoxy]-phenyl]-methanone, (1RS,2RS)-(4-bromo-phenyl)-[4-[2-[(cyclopropyl-methyl-amino)-methyl]-cyclopropylmethoxy]-2-fluoro-phenyl]-methanone, (1RS,2RS)-[4-[2-[(allyl-cyclopropyl-amino)-methyl]-cyclopropylmethoxy]-phenyl]-(4-bromo-phenyl)-methanone, and (1RS,2RS)-1-[4-[2-[(cyclopropyl-methyl-amino)-methyl]-cyclopropyl-methoxy]-phenyl]-5-methyl-hexan-1-one.

7. The compound according to claim 1, wherein T is a group CHOH, CHF, C(R⁴,R⁵) or C=NOR⁶.

8. The compound of claim 7, wherein T is a group C(OH, $C_1$–$C_{13}$ alkyl), C(OH, $C_2$–$C_{13}$ alkenyl), C=CH$_2$ or C=NO ($C_1$–$C_{13}$ alkyl).

9. The compound according to claim 1 of the formula:

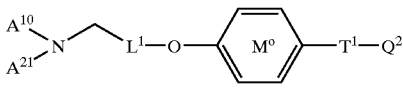

Ib wherein $A^{10}$ is $C_1$–$C_{13}$ alkyl, $A^{21}$ is $C_3$–$C_{13}$ alkenyl, $L^1$ is $C_4$–$C_{11}$ alkylene containing at least 4 C atoms between the two free valencies or $C_3$–$C_{11}$ alkenylene containing at least 3 C atoms between the two free valencies, $M^0$ is 1,4-phenylene or halogenated 1,4-phenylene, $T^1$ is a group,

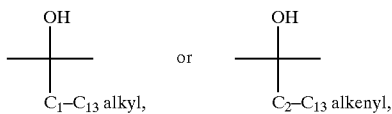

C=CH$_2$ or C=NO—$C_1$–$C_{13}$ alkyl and $Q^2$ is halophenyl or $C_6$–$C_{13}$ alkenyl containing 0 to 3 methyl substituents.

10. The compound according to claim 9, wherein $A^{10}$ is methyl, $A^{21}$ is allyl, $L^1$ is n-pentylene or n-propenylene, $M^0$ is 1,4-phenylene or fluorinated 1,4-phenylene, and $Q^2$ is bromophenyl or 4-methylpent-3-enyl.

11. The compound according to claim 9, selected from the group consisting of:
- (E)-(RS)-1-[4-[4-(allyl-methyl-amino)-but-2-enyloxy]-phenyl]-(4-bromo-phenyl)-ethanol,
- (E)-(RS)-1-[4-[4-(allyl-methyl-amino)-but-2-enyloxy]-phenyl]-1-(4-bromo-phenyl)-prop-2-en-1-ol,
- (E)-allyl-[4-[4-[1-(4-bromo-phenyl)-vinyl]-phenoxy]-but-2-enyl]-methyl-amine,
- (RS)-1-[4-[6-(allyl-methyl-amino)-hexyloxy]-2-fluoro-phenyl]-1-(4-bromo-phenyl)-ethanol, and
- (E)-(RS)-2-[4-[4-(allyl-methyl-amino)-but-2-enyloxy]-phenyl]-6-methyl-hept-5-en-2-ol.

12. The compound according to claim 8 selected from the group consisting of:
- (E)-(RS)-[4-[4-(Allyl-methyl-amino)-but-2-enyloxy]-phenyl]-(4-bromo-phenyl)-cyclopropyl-methanol,
- (E)-(RS)-1-[4-[4-(allyl-methyl-amino)-but-2-enyloxy]-phenyl]-1-(4-bromo-phenyl)-2,2,2-trifluoro-ethanol,
- (RS)-1-[4-[6-(allyl-methyl-amino)-hexyloxy]-phenyl]-1-(4-bromo-phenyl)-2,2,2-trifluoro-ethanol,
- (E)-allyl-[4-[4-[1-(4-bromo-phenyl)-cyclopropyl]-phenoxy]-but-2-enyl]-methyl-amine,
- (E)-(R or S)-1-[4-[4-(allyl-methyl-amino)-but-2-enyloxy]-phenyl]-(4-bromo-phenyl)-ethanol,
- (E)-(S or R)-1-[4-[4-(allyl-methyl-amino)-but-2-enyloxy]-phenyl]-(4-bromo-phenyl)-ethanol,
- allyl-[6-[4-[1-(4-bromo-phenyl)-vinyl]-3-fluoro-phenoxy]-hexyl]-methyl-amine,
- (E)-(RS)-1-[4-[4-(allyl-methyl-amino)-but-2-enyloxy]-3-fluoro-phenyl]-(4-bromo-phenyl)-prop-2-en-1-ol,
- (RS)-1-[4-[(allyl-methyl-amino)-methyl]-biphenyl-4-yl]-1-(4-bromo-phenyl)-ethanol,
- (RS)-5-[6-(allyl-methyl-amino)-hexyloxy]-2-[1-(4-bromo-phenyl)-1-hydroxy-allyl]-phenol,
- (RS)-1-[4-[6-(allyl-methyl-amino)-hexyloxy]-2-amino-phenyl]-1-(4-bromo-phenyl)-prop-2-en-1-ol,
- (RS)-allyl-[4'-[(4-bromo-phenyl)-fluoro-methyl]-biphenyl-4-ylmethyl]-methyl-amine,
- (E)- and/or (Z)-[4-[(E)-4-(allyl-methyl-amino)-but-2-enyloxy]-phenyl]-(4-bromo-phenyl)-methanone O-methyl oxime,
- (E)- and/or (Z)-[4-[(E)-4-(allyl-methyl-amino)-but-2-enyloxy]-phenyl]-(4-bromo-phenyl)-methanone oxime,
- (E)- and/or (Z)-[4-[(E)-4-allyl-methyl-amino)-but-2-enyloxy]-phenyl-(4-bromo-phenyl)-methanone O-tert-butyl oxime,
- (E)- and/or (Z)-[4-[(E)-4-(allyl-methyl-amino)-but-2-enyloxy]-phenyl]-(4-bromo-phenyl)-methanone O-allyl oxime, and
- (E)- and/or (Z)-[4-[6-(allyl-methyl-amino)-hexyloxy]-2-fluoro-phenyl]-(4-bromo-phenyl)-methanone oxime.

13. The compound according to claim 1, wherein M is 1,4-phenylene or 1,4-phenylene substituted by at least one substituent group consisting of $C_1$–$C_{13}$ alkyl, halogen, NH$_2$, $C_1$–$C_{13}$ mono-alkylated amino, $C_2$–$C_6$ di-alkylated amino, $C_1$–$C_{13}$ alkanoylamino, $C_1$–$C_{13}$ alkylsulphonylamino, OH, $C_1$–$C_{13}$ alkyl(O), $C_1$–$C_{13}$ alkyl(S), and 1,2,4-triazol-1-yl.

14. The compound according to claim 13, wherein M is 1,4-phenylene substituted by NH$_2$, mono- or di-alkylated amino, OH, S-alkyl or two halogen atoms.

15. The compound according to claim 13 of the formula:

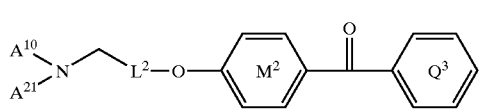

Ic wherein $A^{10}$ is $C_1$–$C_{13}$ alkyl, $A^{21}$ is $C_3$–$C_{13}$ alkenyl, $L^2$ is $C_4$–$C_{11}$ alkylene containing at least 4 C atoms between the two free valencies, $M^2$ is 1,4-phenylene substituted by NH$_2$, mono- or dialkylated amino, OH, S($C_1$–$C_{13}$-alkyl) or two halogen atoms and $Q^3$ is halogenated phenyl.

16. The compound according to claim 15, wherein $A^{10}$ is methyl, $A^{21}$ is allyl, $L^2$ is n-pentylene, $M^2$ is 1,4-phenylene substituted by NH$_2$, NHCH$_3$, N(CH$_3$)$_2$, OH, SCH$_3$ or by two F atoms and $Q^3$ is bromophenyl.

17. The compound according to claim 16, selected from the group consisting of:
- (E)-[4-[4-(allyl-methyl-amino)-but-2-enyloxy]-2,5-difluoro-phenyl]-(4-bromo-phenyl)-methanone,
- [4-[6-(allyl-methyl-amino)-hexyloxy]-2-methylsulphanyl-phenyl]-(4-bromo-phenyl)-methanone,
- [4-[6-(allyl-methyl-amino)-hexyloxy]-2-methylamino-phenyl]-(4-bromo-phenyl)-methanone,
- [4-[6-(allyl-methyl-amino)-hexyloxy]-2-dimethylamino-phenyl]-(4-bromo-phenyl)-methanone,
- [4-[6-(allyl-methyl-amino)-hexyloxy]-2-hydroxy-phenyl]-(4-bromo-phenyl)-methanone, and
- [2-amino-4-[6-(allyl-methyl-amino)-hexyloxy]-phenyl]-(4-bromo-phenyl)-methanone.

18. The compound according to claim 13 selected from the group consisting of:
- (E)-(4-Bromo-phenyl)-[2,5-difluoro-4-(4-dimethylamino-but-2-enyloxy]-methanone,

[4-[6-(allyl-methyl-amino)-hexyloxy]-2,5-difluoro-phenyl]-(4-bromo-phenyl)-methanone, (E)-[4-[4-(allyl-methyl-amino)-but-2-enyloxy]-2,5-difluoro-phenyl]-(2,4-difluoro-phenyl)-methanone, (E)-[2,5-difluoro-4-(4-dimethylamino-but-2-enyloxy)-phenyl]-(2,4-difluoro-phenyl)-methanone,

[4-[6-(allyl-methyl-amino)-hexyloxy]-2,5-difluoro-phenyl]-(2,4-difluoro-phenyl)-methanone, (2,4-difluoro-phenyl)-[4-(6-dimethylamino-hexyloxy)-2,5-difluoro-phenyl]methanone, (E)-[4-[4-(allyl-methyl-amino)-but-2-enyloxy]-2,3,5,6-tetrafluoro-phenyl]-(4-bromo-phenyl)-methanone, (E)-[4-[4-(allyl-methyl-amino)-but-2-enyloxy]-3-fluoro-2-methyl-phenyl]-(4-bromo-phenyl)-methanone, (E)-[4-[4-(allyl-methyl-amino)-but-2-enyloxy]-2-methylsulphanyl-phenyl]-(4-bromo-phenyl)-methanone, (E)-N-[11-[4-[4-(allyl-methyl-amino)-but-2-enyloxy]-3-fluoro-phenyl]-11-oxo-undecyl]-acetamide, (E)-[4-(4-allyl-methyl-amino-but-2-enyloxy)-2-hydroxy-phenyl]-(4-bromo-phenyl)-methanone, (E)-1-[4-[4-(allyl-methyl-amino)-but-2-enyloxy]-3-fluoro-phenyl]-11-amino-undecan-1-one, (E)-1-[4-[(E)-4-(allyl-methyl-amino)-but-2-enyloxy]-3-fluoro-phenyl]-2-[(E)-3,7-dimethyl-octa-2,6-dienyl]-5,9-dimethyl-deca-4,8-dien-1-one, (E)-1-[4-[4-(allyl-methyl-amino)-but-2-enyloxy]-3-fluoro-phenyl]-5-methyl-2-(3-methyl-but-2-enyl)-hex-4-en-1-one, (E)-(RS)-1-[4-[4-(allyl-methyl-amino)-but-2-enyloxy]-3-fluoro-phenyl]-3-hydroxy-5-methyl-hex-4-en-1-one, (E)-(RS)-1-[4-[4-(allyl-methyl-amino)-but-2-enyloxy]-2-fluoro-phenyl]-3-hydroxy-5-methyl-hex-4-en-1-one, (E)-(RS)-1-[4-[4-(allyl-methyl-amino)-but-2-enyloxy]-phenyl]-3-hydroxy-5-methyl-hex-4-en-1-one, (E)-(RS)-1-[4-[(E)-4-(allyl-methyl-amino)-but-2-enyloxy]-3-fluoro-phenyl]-3-hydroxy-5,9-dimethyl-deca-4,8-dien-1-one, (E)-(RS)-13-(allyl-methyl-amino)-1-[4-[4-(allyl-methyl-amino)-but-2-enyloxy]-3-fluoro-phenyl]-3-hydroxy-tridecan-1-one, (E)-1-[4-[(E)-4-(allyl-methyl-amino)-but-2-enyloxy]-3-fluoro-phenyl]-5-methyl-hexa-2,4-dien-1-one, (E)-13-(allyl-methyl-amino)-1-[4-[(E)-4-(allyl-methyl-amino)-but-2-enyloxy]-3-fluoro-phenyl]-tridec-2-en-1-one, (E)-1-[4-[(E)-4-(allyl-methyl-amino)-but-2-enyloxy]-2-fluoro-phenyl]-5-methyl-hexa-2,4-dien-1-one, (E)-1-[4-[(E)-4-(allyl-methyl-amino)-but-2-enyloxy]-phenyl]-5-methyl-hexa-2,4-dien-1-one, (2E,4E)-1-[4-[(E)-4-(allyl-methyl-amino)-but-2-enyloxy]-3-fluoro-phenyl]-5,9-dimethyl-deca-2,4,8-trien-1-one,

[4-[6-(allyl-methyl-amino)-hexyloxy]-2-1H-[1,2,4]triazol-1-yl-phenyl]-(4-bromo-phenyl)-methanone, 1-[4-[6-(allyl-methyl-amino)-hexyloxy]-2-methylamino-pheny]4-methyl-hex-5-en-1-one, (E)-1-[4-[4-(allyl-methyl-amino)-but-2-enyloxy]-2-methylsulphanyl-phenyl]-5-methyl-hex-4-en-1-one, N-[5-[6-(allyl-methyl-amino)-hexyloxy]-2-(4-bromo-benzoyl)-phenyl]-methanesulphonamide, (4-bromo-phenyl)-(4'-dimethylaminomethyl-3-hydroxy-biphenyl-4-yl)-methanone, N-[5-[6-(allyl-methyl-amino)-hexyloxy]-2-(4-bromo-benzoyl)-phenyl]-formamide.

19. The compound according to claim 1, wherein L is (a) a $C_4$–$C_{11}$ alkylene which has at least 4 C atoms between the two valencies and which is bonded to M via NH or N-alkanoyl or (b) a $C_3$–$C_{11}$ alkenylene group which has at least 3 C atoms between the two free valencies which is bonded to M via NH or N-alkanoyl.

20. The compound according to claim 19 of the formula:

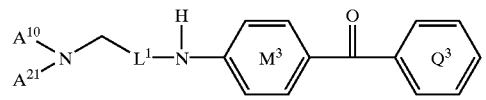

wherein $A^{10}$ is $C_1$–$C_{13}$ alkyl, $A^{21}$ is $C_2$–$C_{13}$ alkenyl, $L^1$ is $C_4$–$C_{11}$ alkylene containing at least 4 C atoms between the two free valencies or $C_4$–$C_{11}$ alkenylene containing at least 3 C atoms between the two free valencies, $M^3$ is halogenated 1,4-phenylene, and $Q^3$ is halogenated phenyl.

21. The compound according to claim 20, wherein $A^{10}$ is methyl, $A^{21}$ is allyl, $L^1$ is n-pentylene or n-propenylene, $M^3$ is fluorophenylene, and $Q^3$ is bromophenyl.

22. The compound according to claim 21 selected from the group consisting of:

(E)-[4-[4-(allyl-methyl-amino)-but-2-enylamino]-3-fluoro-phenyl]-(4-bromo-phenyl)-methanone, and

[4-[6-(allyl-methyl-amino)-hexylamino]-3-fluoro-phenyl]-(4-bromo-phenyl)-methanone.

23. The compound according to claim 20 selected from the group consisting of:

(E)-N-[4-(Allyl-methyl-amino)-but-2-enyl]-N-[4-(4-bromo-benzoyl)-2-fluoro-phenyl]-acetamide, and N-[6-(allyl-methyl-amino)-hexyl]-N-[4-(4-bromobenzoyl)-2-fluoro-phenyl]-acetamide.

24. The compound according to claim 1, wherein M is a group of the formula:

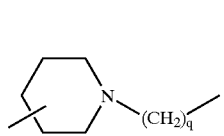

and q is 1 or 0.

25. The compound of claim 24 wherein M and T together form the piperidin-1-yl-sulphonyl group.

26. The compound according to claim 25 of the formula

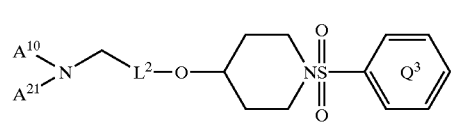

wherein $A^{10}$ is $C_1$–$C_{13}$ alkyl, $A^{21}$ is $C_3$–$C_{13}$ alkenyl, $L^2$ is $C_4$–$C_{11}$ alkylene containing at least 4 C atoms between the two free valencies, and $Q^3$ is halogenated phenyl.

27. The compound of claim 26, wherein $A^{10}$ is methyl, $A^{21}$ is allyl, $L^2$ is n-pentylene, and $Q^3$ is bromophenyl.

28. The compound of claim 27 which is allyl-[6-[1-(4-bromo-phenylsulphonyl)-piperidin4-yloxy]-hexyl]-methyl-amine.

29. The compound according to claim 24 selected from the group consisting of:

[4-[6-(allyl-methyl-amino)-hexyloxy]-piperidin-1-yl]-1-(4-bromo-phenyl)methanone, and 2-[4-[6-(allyl-methyl-amino)-hexyloxy]-piperidin-1-yl]-1-(4-bromo-phenyl)-ethanone.

30. The compound according to claim 1, wherein $A^1$ is alkyl and $A^2$ is OH, alkyl, or alkyl substituted by a group $R^1$, $CONH_2$ or CN; or $A^1$ and $A^2$ together form a $C_2$–$C_5$ alkylene, $C_2$–$C_5$ alkylene substituted with $R^1$, $C_4$–$C_5$ alkenylene, $C_4$–$C_5$ alkenylene substituted with $R^1$; or $A^1$ and $A^2$ together form a $C_2$–$C_5$ alkylene, $C_2$–$C_5$ alkylene substituted with $R^1$, $C_4$–$C_5$ alkenylene, $C_4$–$C_5$ alkenylene substituted with $R^1$, wherein a C atom is replaced by a N atom; or $A^1$ and $A^3$ together form a $C_2$–$C_5$ alkylene, $C_2$–$C_5$ alkylene substituted with $R^1$, $C_4$–$C_5$ alkenylene, $C_4$–$C_5$ alkenylene substituted with $R^1$; or $A^1$ and $A^3$ together form a $C_2$–$C_5$ alkylene, $C_2$–$C_5$ alkylene substituted with $R^1$, $C_4$–$C_5$ alkenylene, $C_4$–$C_5$ alkenylene substituted with $R^1$, wherein a C atom is replaced by a N atom; and $R^1$ is OH, oxo, alkyl-O, alkyl-S or dialkylamino bonded to a saturated C atom of $A^2$, $A^1$-$A^2$ or $A^1$-$A^3$, provided that a C atom substituted by $R^1$ or an unsaturated C atom present in $A^2$, $A^1$-$A^2$ or $A^1$-$A^3$ must be bonded in a position other than the α-position to $N(A^1A^2)$.

31. The compound according to claim 30, wherein $A^1$ and $A^2$ together are OH-substituted $C_3$–$C_5$ alkylene.

32. The compound according to claim 31 of the formula:

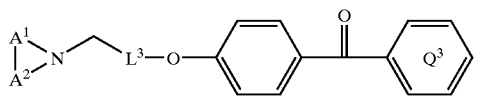

If wherein $A^1$ and $A^2$ together are a $C_3$–$C_5$ alkylene group which is substituted by OH, $L^3$ is a $C_3$–$C_1$, alkenylene with at least 3 C atoms between the two free valencies, and $Q^3$ is halogenated phenyl.

33. The compound of claim 32, wherein $A^1$ and $A^2$ together are 4-hydroxy-piperidin-1-yl, $L^3$ is n-propenylene and $Q^3$ is bromophenyl.

34. The compound of claim 33 which is (E)-(4-bromo-phenyl)-[4-[4-(4-hydroxy-piperidin-1-yl)-but-2-enyloxy]-phenyl]-methanone.

35. The compound according to claim 30 selected from the group consisting of:

Cyclohexyl p-[[(E)-4-(dimethylamino)-2-butenyl]oxy] phenyl ketone, (E)-[[4-[4-(4-bromo-benzoyl)-phenoxy]-but-2-enyl]-methyl-amino]-acetonitrile, (E)-3-[[4-[4-(4-bromo-benzoyl)-phenoxy]-but-2-enyl]-methyl-amino]-propionitrile, (E)-(4-bromo-phenyl)-[4-[4-(4-dimethylamino-piperidin-1-yl)-but-2-enyloxy]-phenyl]-methanone, (4-bromo-phenyl)-[4-[6-(hydroxy-methyl-amino)-hexyloxy]-phenyl]-methanone, (E)-(4-bromo-phenyl)-[4-[4-(hydroxy-methyl-amino)-but-2-enyloxy]-phenyl]-methanone, (E)-(4-bromo-phenyl)-[4-[4-[(2-methoxy-ethyl)-methyl-amino]-but-2-enyloxy]-phenyl]-methanone, (E)-(4-bromo-phenyl)-[4-[4-[methyl-(2-methylsulphanyl-ethyl)-amino]-but-2-enyloxy]-phenyl]-methanone, (E)-(4-bromo-phenyl)-[4-(4-imidazol-1-yl-but-2-enyloxy)-phenyl]-methanone, (4-bromo-phenyl)-[4-(6-imidazol-1-yl-hexyloxy)-phenyl]-methanone, (4-bromo-phenyl)-[4-[6-[( 3-hydroxy-propyl)-methyl-amino]-hexyloxy]-phenyl]-methanone, 1-[[6-[4-(4-bromo-benzoyl)-phenoxy]-hexyl]-methyl-amino]-propan-2-one, (E)-2-[[4-[4-(4-bromo-benzoyl)-phenoxy]-but-2-enyl]-methyl-amino]-acetamide, and (±)(4-bromo-phenyl)-[4'-(1-methylpyrrolidin-2-yl)-biphenyl-4-yl]-methanone.

36. The compound according to claim 1, wherein p=0 and L is $C_6$–$C_{11}$-alkenylene or $C_6$–$C_{11}$-alkadienylene bonded to T.

37. The compound according to claim 36 of the formula:

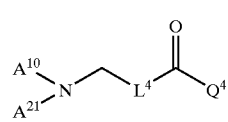

Ig wherein $A^{10}$ is $C_1$–$C_{13}$ alkyl, $A^{21}$ is $C_3$–$C_{13}$ alkenyl, $L^4$ is $C_6$–$C_{11}$ alkadienylene, and $Q^4$ is $C_6$–$C_{13}$ alkenyl with 0 to 3 methyl substituents.

38. The compound of claim 37, wherein $A^{10}$ is methyl, $A^{21}$ is allyl, $L^4$ is dimethyloctadienylene, and $Q^4$ is 4-methyl-3-pentenyl.

39. The compound of claim 38 which is (9E,13E)-15-(allyl-methyl-amino)-2,9,13-trimethyl-pentadeca-2,9,13-trien-6-one.

40. The compound according to claim 36 selected from the group consisting of:

(4E,8E)-10-(Allyl-methyl-amino)-1-(4-bromo-phenyl)-4,8-dimethyl-deca-4,8-dien-1-one, (4E,8E)-1-(4-bromo-phenyl)-10-dimethylamino-4,8-dimethyl-deca-4,8-dien-1-one, (7E,11E)-13-(allyl-methyl-amino)-2,7,11-trimethyl-trideca-2,7,11-trien-6-one, (7E,11E)- and (7Z,11E)-13-(allyl-methyl-amino)- 2,7,11-trimethyl-trideca-2,7,11-trien-6-one, (2E,6E)-8-(allyl-methyl-amino)-1-(4-bromo-phenyl)-2,6-dimethyl-octa-2,6-dien-1-one, (7E,11E)-13-(allyl-methyl-amino)-7,11-dimethyl-trideca-1,7,11-trien-6-one, (2E,6E)-(RS)-8-(allyl-methyl-amino)-1-(4-bromo-phenyl)-2,6-dimethyl-octa-2,6-dien-1-ol, (E)-(RS)-8-(allyl-methyl-amino)-1-(4-bromo-phenyl)-2,6-dimethyl-oct-6-en-1-one, (2E,6E)-(RS)-10-(allyl-methyl-amino)-1-(4-bromo-phenyl)-3,7-dimethyl-deca-2,6-dien-1-ol, (2E,6E)-(RS)-8-(allyl-methyl-amino)-1-(4-bromo-phenyl)-3,7-dimethyl-octa-2,6-dien-1-ol, (2E,6E)-10-(allyl-methyl-amino)-1-(4-bromo-phenyl)-3,7-dimethyl-deca-2,6-dien-1-one, and (2E,6E)-8-(allyl-methyl-amino)-1-(4-bromo-phenyl)-3,7-dimethyl-octa-2,6-dien-1-one.

41. The compound according to claim 1, wherein M is thienylene or pyridylene.

42. The compound of claim 41 selected from the group consisting of:

(E)-1-[6-[6-(Allyl-methyl-amino)-hexyloxy]-pyridin-3-yl]-5-methyl-hexa-2,4-dien-1-one, 6-[6-(allyl-methyl-amino)-hexyloxy]-pyridin-3-yl]-(4-bromo-phenyl)-methanone, (E)-[6-[4-(allyl-methyl-amino)-but-2-enyloxy]-pyridin-3-yl]-(4-bromo-phenyl)-methanone,

[5-16-(allyl-methyl-amino)-hexyloxy]-pyridin-2-yl]-(4-bromo-phenyl)-methanone, 5-(4-[(allyl-methylamino)-methyl]-phenyl)-thiophen-2-yl)-(4-bromophenyl)-methanone, 5-(4-[dimethylamino)-methyl]-phenyl)-thiophen-2-yl)-(4-bromophenyl)-methanone, 5-(4-[(allyl-methylamino)-methyl]-phenyl)-thiophen-2-yl)-(4-(2,4-difluorophenyl))-methanone, (2-dimethylamino-4-fluoro-phenyl)-[5-(4-dimethylaminomethyl-phenyl)-thiophen-2-yl]-methanone.

43. The compound according to claim 1, wherein L is cycloalkylene-alkylene bonded to M via an O atom.

44. The compound of claim 43 selected from the group consisting of:

(1RS,2RS)-(4-bromo-phenyl)-[4-[2-[(ethyl-methyl-amino)-methyl]-cyclopropylmethoxy]-phenyl]-methanone, and (1RS,2RS)-[4-[2-[(allyl-methyl-amino)-methyl]-cyclopropylmethoxy]-phenyl]-(4-bromo-phenyl)-methanone.

45. A compound of the formula:

$$\begin{array}{c}A^{100}\\ \phantom{A}\diagdown\\ \phantom{AAA}N{-}L^{100}{-}(R^{100})_a{-}M^{100}{-}T^{100}{-}Q^{100}\\ \phantom{A}\diagup\\ A^{200}\end{array}$$

wherein $A^{100}$ is $C_1$–$C_6$ alkyl;

$A^{200}$ is $C_3$–$C_6$ cycloalkyl, $C_3$–$C_6$ alkenyl, $C_1$–$C_6$ alkyl, $C_3$–$C_6$ cycloalkyl-$C_1$–$C_{13}$ alkyl;

$L^{100}$ is $C_4$–$C_6$ alkylene, $C_3$–$C_6$ alkenylene, or $C_3$–$C_6$ cycloalkylene-$C_1$–$C_{13}$-alkylene;

a is 1;

$R^{100}$ is O;

$M^{100}$ is 1,4-phenylene, 1,4-phenylene substituted with at least one substituent selected from the group consisting of halogens, $T^{100}$ is C=O, C=N—O—($C_1$–$C_6$ alkyl), C=CH$_2$, $$\underset{C_{1-6}\text{-alkyl;}}{\overset{OH}{\underset{|}{-\!\!\!\!-\!\!\!\!\!\overset{|}{\mathrm{C}}\!\!\!\!-\!\!\!\!-}}}$$

and $Q^{100}$ is phenyl substituted with at least one substituent selected from the group consisting of halogens, or a pharmaceutically usable acid addition salt thereof.

46. The compound of claim 45, wherein $A^{100}$ is $C_1$–$C_3$ alkyl;

$A^{200}$ is $C_3$–$C_6$ cycloalkyl, $C_3$–$C_6$ alkenyl;

$L^{100}$ is $C_3$–$C_5$ alkenylene or $C_3$–$C_6$ cycloalkylene-$C_1$–$C_3$-alkylene;

a is 1;

$R^{100}$ is O;

$M^{100}$ is 1,4, phenylene, 1,4 phenylene substituted with at least one fluorine;

$T^{100}$ is C=O, C=N—O—($C_1$–$C_3$ alkyl), C=CH$_2$, $$\underset{C_{1-3}\text{-alkyl;}}{\overset{OH}{\underset{|}{-\!\!\!\!-\!\!\!\!\!\overset{|}{\mathrm{C}}\!\!\!\!-\!\!\!\!-}}}$$

and $Q^{100}$ is phenyl substituted with at least one halogen atom, or a pharmaceutically usable acid addition salt thereof.

47. The compound of claim 46, wherein $A^{100}$ is methyl;

$A^{200}$ is cyclopropyl or allyl;

$L^{100}$ is cyclopropylene-methylene or propenylene;

$R^{100}$ is O;

$M^{100}$ is 1,4-phenylene or 3 fluoro-1,4-phenylene;

$T^{100}$ is C=O or C(CH$_3$)OH; and $Q^{100}$ is bromophenyl, or a pharmaceutically usable acid addition salt thereof.

48. The compound of claim 47 having the structure:

or a pharmaceutically usable acid addition salt thereof.

* * * * *